United States Patent
Ito et al.

(10) Patent No.: US 10,894,810 B2
(45) Date of Patent: Jan. 19, 2021

(54) PROTEIN SECRETORY PRODUCTION METHOD

(71) Applicant: AJINOMOTO CO., INC., Tokyo (JP)

(72) Inventors: Yumi Ito, Kanagawa (JP); Yoshihiko Matsuda, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/389,480

(22) Filed: Apr. 19, 2019

(65) Prior Publication Data

US 2019/0241622 A1 Aug. 8, 2019

Related U.S. Application Data

(63) Continuation of application No. PCT/JP2017/037956, filed on Oct. 20, 2017.

(30) Foreign Application Priority Data

Oct. 21, 2016 (JP) .................. 2016-206728

(51) Int. Cl.

| A61K 35/74 | (2015.01) |
|---|---|
| C07K 14/195 | (2006.01) |
| C07K 14/435 | (2006.01) |
| C07K 14/47 | (2006.01) |
| C07K 1/12 | (2006.01) |
| C12N 15/09 | (2006.01) |
| C07K 14/34 | (2006.01) |
| C07K 19/00 | (2006.01) |
| C12P 21/02 | (2006.01) |
| C12R 1/15 | (2006.01) |

(52) U.S. Cl.
CPC .............. *C07K 14/195* (2013.01); *C07K 1/12* (2013.01); *C07K 14/34* (2013.01); *C07K 14/43595* (2013.01); *C07K 14/47* (2013.01); *C07K 19/00* (2013.01); *C12N 15/09* (2013.01); *C12P 21/02* (2013.01); *C12R 1/15* (2013.01)

(58) Field of Classification Search
None
See application file for complete search history.

(56) References Cited

U.S. PATENT DOCUMENTS

| 4,965,197 A | 10/1990 | Liebl et al. |
|---|---|---|
| 6,027,920 A | 2/2000 | Joliff et al. |
| 2003/0082746 A1 | 5/2003 | Kikuchi et al. |
| 2004/0126847 A1 | 7/2004 | Kikuchi et al. |
| 2007/0184525 A1 | 8/2007 | Date et al. |
| 2014/0220637 A1 | 8/2014 | Tsurui et al. |
| 2014/0234901 A1 | 8/2014 | Matsuda et al. |
| 2014/0255996 A1 | 9/2014 | Matsuda et al. |
| 2018/0037918 A1 | 2/2018 | Matsuda et al. |

FOREIGN PATENT DOCUMENTS

| JP | 6-502548 A | 3/1994 |
|---|---|---|
| JP | 11-169182 A | 6/1999 |
| JP | 4320769 B2 | 6/2009 |
| JP | 4362651 B2 | 8/2009 |
| JP | 4730302 B2 | 4/2011 |
| JP | 2014-532424 A | 12/2014 |
| WO | WO2013/062029 A1 | 5/2013 |
| WO | WO2013/065772 A1 | 5/2013 |
| WO | WO2013/065869 A1 | 5/2013 |
| WO | WO2013/118544 A1 | 8/2013 |
| WO | WO2016/171224 A1 | 10/2016 |

OTHER PUBLICATIONS

International Search Report for PCT Patent App. No. PCT/JP2017/037956 (dated Jan. 23, 2018).

Bott, M., et al., "Two-component signal transduction in Corynebacterium glutamicum and other corynebacterium: on the way towards stimuli and targets," Appl. Microbiol. Biotechnol. 2012;94:1131-1150.

Simonen, M., et al., "Protein Secretion in Bacillus Species," Microbiol. Rev. 1993;57(1):109-137.

Cregg, J. M., et al., "Recent Advances in the Expression of Foreign Genes in Pichia pastoris," Biotechnol. 1993;11:905-910.

Christensen, T., et al., "High Level Expression of Recombinant Genes in Aspergillus oryzae," Biotechnol. 1988;6:1419-1422.

Dunn-Coleman, N. S., et al., "Commercial Levels of Chymosin Production by Aspergillus," Biotechnol. 1991;9:976-981.

Liebl, W., et al., "Expression, Secretion, and Processing of Staphylococcal Nuclease by Corynebacterium glutamicum," J. Bacteriol. 1992;174(6):1854-1861.

Billman-Jacobe, H., et al., "Expression and Secretion of Heterologous Proteases by Corynebacterium glutamicum," Appl. Environmen. Microbiol. 1995;61(4):1610-1613.

Salim, K, et al., "Heterologous Expression of the Mycobacterium tuberculosis Gene Encoding Antigen 85A in Corynebacterium glutamicum," Appl. Environmen. Microbiol. 1997;63(11):4392-4400.

(Continued)

*Primary Examiner* — Hope A Robinson

(74) *Attorney, Agent, or Firm* — Cermak Nakajima & McGowan LLP; Shelley Guest Cermak

(57) ABSTRACT

A novel technique for improving secretory production of a heterologous protein by coryneform bacteria is described, and thereby a method for secretory production of a heterologous protein is provided. A coryneform bacterium able to secrete a heterologous protein and modified so that the activity of HrrSA system is reduced is cultured to produce the heterologous protein by secretory production.

17 Claims, 3 Drawing Sheets

Specification includes a Sequence Listing.

(56) References Cited

OTHER PUBLICATIONS

Chaddock, A. M., et al., "A new type of signal peptide: central role of a twin-arginine motif in transfer signals for the delta pH-dependent thylakoidal protein translocase," The EMBO Journal 1995;14(12):2715-2722.

Hynds, P. J., et al., "The Sec-independent Twin-arginine Translocation System Can Transport Both Tightly Folded and Malfolded Proteins across the Thylakoid Membrane," J. Biol. Chem. 1998;273(52):34868-34874.

Kocan, M., et al., "Two-Component Systems of Corynebacterium glutamicum: Deletion Analysis and Involvement of the PhoS-PhoR System in the Phosphate Starvation Response," J. Bacteriol. 2006;188(2):724-732.

Hentschel, E., et al., "Phosphatase activity of the histidine kinases ensures pathway specificity of the ChrSA and HrrSA two-component systems in Corynebacterium glutamicum," Mol. Microbiol. 2014;92(6):1326-1342.

Frunzke, J., et al., "Control of Heme Homeostasis in Corynebacterium glutamicum by the Two-Component System HrrSA," J. Bacteriol. 2011;193(5):1212-1221.

Matsuda, Y., et al., Abstracts of the Lectures in Annual Meeting of the Japan Society for Bioscience, Biotechnology, and Agrochemistry, 2012, with its English translation.

Matsuda, Y., et al., Abstracts of the Lectures in Annual Meeting of the Japan Society for Bioscience, Biotechnology, and Agrochemistry, 2013, with its English translation.

International Preliminary Report on Patentability for PCT Patent App. No. PCT/JP2017/037956 (dated May 2, 2019).

PROTEIN SECRETORY PRODUCTION METHOD

This application is a Continuation of, and claims priority under 35 U.S.C. § 120 to, International Application No. PCT/JP2017/037956, filed Oct. 20, 2017, and claims priority therethrough under 35 U.S.C. § 119 to Japanese Patent Application No. 2016-206728, filed Oct. 21, 2016, the entireties of which are incorporated by reference herein. Also, the Sequence Listing filed electronically herewith is hereby incorporated by reference (File name: 2019-04-19T US-594 Seq List; File size: 77 KB; Date recorded: Apr. 19, 2019).

BACKGROUND

Described herein is a method for secretory production of a heterologous protein.

As secretory production of heterologous proteins by microorganisms, methods of secretory production of heterologous proteins have been reported, such as production by a *Bacillus* bacterium (Microbiol. Rev., 57, 109-137 (1993)), methanol-assimilating yeast, *Pichia pastoris* (Biotechnol., 11, 905-910 (1993)), filamentous fungi of the genus *Aspergillus* (Biotechnol., 6, 1419-1422 (1988) and Biotechnol., 9, 976-981 (1991)), and so forth.

Secretory production of heterologous proteins has also been attempted using coryneform bacteria. Secretory production of heterologous proteins by coryneform bacteria has been reported for secretion of a nuclease and a lipase by *Corynebacterium glutamicum* (henceforth also abbreviated as *C. glutamicum*) (U.S. Pat. No. 4,965,197, J. Bacteriol., 174, 1854-1861 (1992)), secretion of a protease such as subtilisin (Appl. Environ. Microbiol., 61, 1610-1613 (1995)), secretion of a protein using signal peptides of cell surface layer proteins PS1 and PS2 (also referred to as CspB) of coryneform bacteria (Japanese Patent Laid-open (Kohyo) No. 6-502548), secretion of a fibronectin-binding protein using the signal peptide of PS2 (CspB) (Appl. Environ. Microbiol., 63, 4392-4400 (1997)), secretion of protransglutaminase using signal peptides of PS2 (CspB) and SlpA (also referred to as CspA) (Japanese Patent No. 4320769), secretion of a protein using a variant type secretion system (Japanese Patent Laid-open (Kokai) No. 11-169182), secretion of a protransglutaminase by a variant strain (Japanese Patent No. 4362651), and so forth. In addition, as techniques for improving secretory production amounts of heterologous proteins by coryneform bacteria, there are known reducing the activity of a cell surface layer protein (WO2013/065869 and WO2013/065772), reducing the activity of a penicillin-binding protein (WO2013/065869), enhancing the expression of a gene encoding a metallopeptidase (WO2013/065772), introducing a mutation into a ribosomal protein S1 gene (WO2013/118544), expressing a heterologous protein with an amino acid sequence comprising Gln-Glu-Thr inserted between a signal peptide and the heterologous protein (WO2013/062029), and so forth.

A general protein secretion pathway is called "Sec system", which is widely present in prokaryotes and eukaryotes; however, a completely different protein secretion pathway has recently been found in thylakoid membranes of chloroplasts of plant cells (EMBO J., 14, 2715-2722 (1995)). This novel secretory pathway has been named the "Tat system" (Twin-Arginine Translocation system) because an arginine-arginine sequence is commonly present in the signal sequence of a protein secreted thereby (EMBO J., 14, 2715-2722 (1995)). It has been reported that proteins are secreted by the Sec system before forming a higher-order structure, while proteins are secreted by the Tat system through a cell membrane after forming a higher-order structure in the cell (J. Biol. Chem., 25; 273(52), 34868-74 (1998)). Also, for coryneform bacteria, secretory production of proteins utilizing a Tat-dependent signal peptide has been reported (WO2013/118544 and Japanese Patent No. 4730302).

As a system by which bacteria respond to various environmental changes inside and outside the cell, a signaling pathway called "two-component regulatory system" is known. The two-component regulatory system consists of two components: a sensor kinase that is responsible for sensing a stimulus of an environmental change, and a response regulator that is responsible for receiving a signal from the sensor kinase and regulating the expression of downstream genes. Specifically, when the sensor kinase senses a stimulus, a specific histidine residue thereof is autophosphorylated, a signal is transduced via transfer of the phosphate group to a specific aspartic acid residue of the response regulator, and the response regulator activated by phosphorylation regulates the expression of downstream genes as a transcription factor.

Knowledge concerning the two-component regulatory system of *C. glutamicum* is detailed in Appl. Microbiol. Biotechnol., 94, 1131-1150 (2012) etc. For *C. glutamicum*, at least 13 types of systems have been known as the two-component regulatory system. Specific examples of the two-component regulatory system include the PhoRS system and the HrrSA system.

The PhoRS system consists of a sensor kinase PhoS protein and a response regulator PhoR protein. Analysis of a PhoRS-deficient strain revealed that the PhoRS system is a regulatory system that senses phosphate depletion in the environment and performs signal transduction (J. Bacteriol., 188, 724-732 (2006)).

The HrrSA system consists of a sensor kinase HrrS protein and a response regulator HrrA protein. Analysis of a HrrSA-deficient strain revealed that the HrrSA system, in the presence of haem, induces the expression of genes involved in degradation of haem and genes encoding haem-containing proteins in the respiratory chain, and represses the expression of genes involved in biosynthesis of haem, and hence, it is considered that the HrrSA system is involved in homeostasis of haem (J. Bacteriol., 193, 1212-1221 (2011)).

However, the relationship between the HrrSA system and secretory production of heterologous proteins has not been previously reported.

SUMMARY

One aspect is to develop a novel technique for improving secretory production of a heterologous protein by a coryneform bacterium, and thereby to provide a method for secretory production of a heterologous protein using a coryneform bacterium.

It has been found that an ability of a coryneform bacterium to produce a heterologous protein by secretory production can be improved by modifying the coryneform bacterium so that the activity of HrrSA system is reduced.

Disclosed herein is a method for producing a heterologous protein comprising: culturing a coryneform bacterium having a genetic construct for secretory expression of the heterologous protein; and collecting the heterologous protein produced by secretory production, wherein the coryneform bacterium has been modified so that the number of molecules of a HrrSA system per cell is reduced as compared with a non-modified strain, wherein the genetic construct comprises, in the direction from 5' to 3', a promoter sequence that functions in the coryneform bacterium, a nucleic acid sequence encoding a signal peptide that functions in the coryneform bacterium, and a nucleic acid sequence encoding the heterologous protein, and wherein the heterologous protein is expressed as a fusion protein with the signal peptide.

Disclosed herein is a method as described above, wherein the number of molecules of the HrrSA system per cell is reduced by reducing the number of molecules of either one or both of a HrrS protein and a HrrA protein per cell.

Disclosed herein is a method as described above, wherein at least the number of molecules of the HrrA protein per cell is reduced.

Disclosed herein is a method as described above, wherein the HrrS protein is selected from the group consisting of: (a) a protein comprising the amino acid sequence of SEQ ID NO: 63; (b) a protein comprising the amino acid sequence of SEQ ID NO: 63, but which includes substitution, deletion, insertion, and/or addition of 1 to 10 amino acid residues, wherein said protein has a function as a sensor kinase of a HrrSA system; and (c) a protein comprising an amino acid sequence showing an identity of 90% or higher to the amino acid sequence of SEQ ID NO: 63, wherein said protein has a function as a sensor kinase of a HrrSA system.

Disclosed herein is a method as described above, wherein the HrrA protein is selected from the group consisting of: (a) a protein comprising the amino acid sequence of SEQ ID NO: 65; (b) a protein comprising the amino acid sequence of SEQ ID NO: 65, but which includes substitution, deletion, insertion, and/or addition of 1 to 10 amino acid residues, wherein said protein has a function as a response regulator of a HrrSA system; and (c) a protein comprising an amino acid sequence showing an identity of 90% or higher to the amino acid sequence of SEQ ID NO: 65, wherein said protein has a function as a response regulator of a HrrSA system.

Disclosed herein is a method as described above, wherein the number of molecules of the HrrS protein and/or the HrrA protein per cell is reduced by reducing the expression of a hrrS gene and/or a hrrA gene, or by disrupting a hrrS gene and/or a hrrA gene.

Disclosed herein is a method as described above, wherein the number of molecules of the HrrS protein and/or the HrrA protein per cell is reduced by deleting a hrrS gene and/or a hrrA gene.

Disclosed herein is a method as described above, wherein the coryneform bacterium has been further modified so as to harbor a phoS gene encoding a mutant PhoS protein, Disclosed herein is a method as described above, wherein the mutation is replacement of an amino acid residue corresponding to the tryptophan residue at position 302 with an amino acid residue other than aromatic amino acid and histidine residues in a wild-type PhoS protein.

Disclosed herein is a method as described above, wherein the amino acid residue other than an aromatic amino acid and a histidine residue is a lysine residue, alanine residue, valine residue, serine residue, cysteine residue, methionine residue, aspartic acid residue, or asparagine residue.

Disclosed herein is a method as described above, wherein the wild-type PhoS protein is selected from the group consisting of: (a) a protein comprising the amino acid sequence of SEQ ID NO: 4, 26, 27, 28, 29, or 30; (b) a protein comprising the amino acid sequence of SEQ ID NO: 4, 26, 27, 28, 29, or 30, but which includes substitution, deletion, insertion, or addition of 1 to 10 amino acid residues, wherein said protein has a function as a sensor kinase of a PhoRS system; (c) a protein comprising an amino acid sequence showing an identity of 90% or higher to the amino acid sequence of SEQ ID NO: 4, 26, 27, 28, 29, or 30, wherein said protein has a function as a sensor kinase of a PhoRS system.

Disclosed herein is a method as described above, wherein the signal peptide is a Tat-dependent signal peptide.

Disclosed herein is a method as described above, wherein the Tat-dependent signal peptide is a signal peptide selected from the group consisting of a TorA signal peptide, SufI signal peptide, PhoD signal peptide, LipA signal peptide, and IMD signal peptide.

Disclosed herein is a method as described above, wherein the coryneform bacterium has been further modified so that the expression of one or more genes encoding a Tat secretion system is increased as compared with a non-modified strain.

Disclosed herein is a method as described above, wherein the one or more genes encoding a Tat secretion system are selected from the group consisting of a tatA gene, tatB gene, tatC gene, tatE gene, and combinations thereof.

Disclosed herein is a method as described above, wherein the signal peptide is a Sec-dependent signal peptide.

Disclosed herein is a method as described above, wherein the Sec-dependent signal peptide is selected from the group consisting of a PS1 signal peptide, PS2 signal peptide, and SlpA signal peptide.

Disclosed herein is a method as described above, wherein the genetic construct further comprises a nucleic acid sequence encoding an amino acid sequence comprising Gln-Glu-Thr between the nucleic acid sequence encoding the signal peptide that functions in the coryneform bacterium and the nucleic acid sequence encoding the heterologous protein.

Disclosed herein is a method as described above, wherein the genetic construct further comprises a nucleic acid sequence encoding an amino acid sequence used for enzymatic digestion between the nucleic acid sequence encoding the amino acid sequence comprising Gln-Glu-Thr and the nucleic acid sequence encoding the heterologous protein.

Disclosed herein is a method as described above, wherein the coryneform bacterium is a bacterium belonging to the genus *Corynebacterium*.

Disclosed herein is a method as described above, wherein the coryneform bacterium is *Corynebacterium glutamicum*.

Disclosed herein is a method as described above, wherein the coryneform bacterium is a modified strain derived from *Corynebacterium glutamicum* AJ12036 (FERM BP-734) or a modified strain derived from *Corynebacterium glutamicum* ATCC 13869.

Disclosed herein is a method as described above, wherein the coryneform bacterium is a coryneform bacterium in which the number of molecules of a cell surface layer protein per cell is reduced.

DETAILED DESCRIPTION

Figure 1:
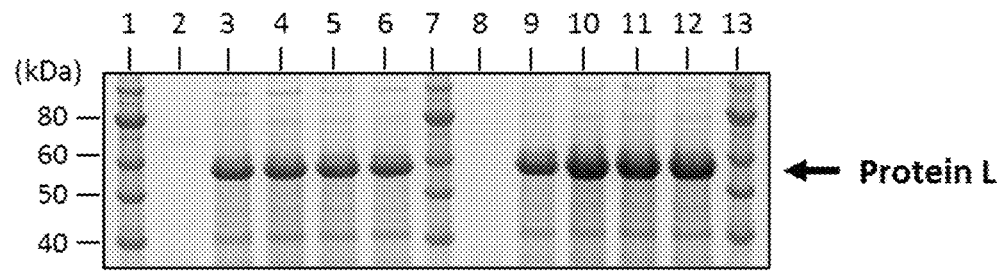
FIG. 1 is a photograph showing the results of SDS-PAGE observed upon expressing Protein L (antibody-binding domain of Protein L fused with CspA signal sequence) in the *C. glutamicum* YDK010 strain and hrrA-gene-deficient strain thereof.

The method as described herein is a method for producing a heterologous protein, the method comprising culturing a coryneform bacterium having a genetic construct for secretory expression of the heterologous protein, and collecting the heterologous protein produced by secretory production, wherein the coryneform bacterium has been modified so that the activity of HrrSA system is reduced.

<1> Coryneform bacterium used for the method as described herein

The chosen coryneform bacterium used for the method can be a coryneform bacterium having a genetic construct for secretory expression of a heterologous protein, which has been modified so that the activity of HrrSA system is reduced. The coryneform bacterium used for the method is also referred to as "bacterium" or "coryneform bacterium". Furthermore, the genetic construct for secretory expression of a heterologous protein harbored by the bacterium is also referred to as "genetic construct".

<1-1> Coryneform bacterium having ability of secretory production of heterologous protein The chosen coryneform bacterium can have the genetic construct for secretory expression of a heterologous protein (genetic construct used for the method as described herein), and therefore has an ability of secretory production of the heterologous protein.

The expression that a protein is "secreted" means that the protein is transported out of a bacterial cell (extracellularly transported). Examples of a position outside of a bacterial cell (outside of a cell) include a medium and a cell surface layer. That is, molecules of the secreted protein may be present, for example, in the medium, in the cell surface layer, or in both of the medium and the cell surface layer. That is, the expression that a protein is "secreted" is not limited to cases where all the molecules of the protein eventually exist in the medium in completely free forms, and also include, for example, cases where all the molecules of the protein are present in the cell surface layer, and cases where a part of the molecules of the protein are present in the medium and the remaining part of the molecules of the protein are present in the cell surface layer.

That is, the term "ability to produce a heterologous protein by secretory production" refers to an ability of the bacterium to secrete the heterologous protein into a medium and/or a cell surface layer, and accumulate it there to such an extent that the heterologous protein can be collected from the medium and/or the cell surface layer, when the bacterium is cultured in the medium. The accumulation amount may be, for example, in terms of the accumulation amount in the medium, 10 µg/L or more, 1 mg/L or more, 100 mg/L or more, or 1 g/L or more. Also, the accumulation amount may be, for example, in terms of the accumulation amount in the cell surface layer, such an amount that if the heterologous protein in the cell surface layer is collected and suspended in a liquid of the same volume as the medium, the concentration of the heterologous protein in the suspension is 10 µg/L or more, 1 mg/L or more, or 100 mg/L or more. In addition, the term "protein" to be produced by secretory production refers to a concept also including those called peptide, such as oligopeptides and polypeptides.

The term "heterologous protein" refers to an exogenous protein relative to a coryneform bacterium that expresses and secretes that protein. The heterologous protein may be, for example, a protein derived from or native to a microorganism, a protein derived from or native to a plant, a protein derived from or native to an animal, a protein derived from or native to a virus, or even a protein of which the amino acid sequence is artificially designed. The heterologous protein may particularly be a derived from or native to a human. The heterologous protein may be a monomeric protein or a multimeric protein. The term "multimeric protein" refers to a protein that may exist as a multimer consisting of two or more subunits. In the multimer, the subunits may be linked by covalent bonds such as disulfide bonds, linked by non-covalent bonds such as hydrogen bonds and hydrophobic interaction, or linked by a combination thereof. The multimer includes one or more intermolecular disulfide bonds. The multimer may be a homo-multimer having a single kind of subunit, or may be a hetero-multimer having two or more kinds of subunits. In the case where the multimeric protein is a hetero-multimer, it is sufficient that at least one subunit selected from the subunits constituting the hetero-multimer is a heterologous protein. That is, all the subunits may be heterologous, or only some of subunits may be heterologous. Although the heterologous protein may be a secretory protein in nature, or may be a non-secretory protein in nature, an example is that it is a secretory protein in nature. Furthermore, the heterologous protein may be a Tat-dependent secretory protein in nature, or may be a Sec-dependent secretory protein in nature. Specific examples of the "heterologous protein" are described herein.

The heterologous protein to be produced may consist of a single kind of protein, or two or more kinds of proteins. Moreover, when the heterologous protein is a hetero-multimer, only one kind of subunit may be produced, or two or more kinds of subunits may be produced. That is, the term "secretory production of a heterologous protein" includes secretory production of all the subunits constituting an objective heterologous protein, as well as secretory production of only a part of the subunits constituting an objective heterologous protein.

Coryneform bacteria are aerobic gram-positive bacilli. Examples of the coryneform bacteria include *Corynebacterium* bacteria, *Brevibacterium* bacteria, *Microbacterium* bacteria, and so forth. Advantages of use of the coryneform bacteria include that they inherently secrete an extremely small amount of proteins out of cells compared with fungi, yeasts, *Bacillus* bacteria, etc., which are conventionally used for secretory production of proteins, and therefore the purification process of a heterologous protein produced by secretory production is expected to be simplified or eliminated, that they can grow well in a simple medium containing a saccharide, ammonia, mineral salts, etc., and therefore they are excellent in view of cost of medium, culture method, and culture productivity, and so forth.

Specific examples of coryneform bacteria include the following species:

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*

*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of coryneform bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium thermoaminogenes* (*Corynebacterium efficiens*) AJ12340 (FERM BP-1539)
*Corynebacterium herculls* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria include bacteria that had previously been classified into the genus *Brevibacterium*, but are presently united into the genus *Corynebacterium* (Int. J. Syst. Bacteriol., 41, 255 (1991)). Moreover, *Corynebacterium stationis* includes bacteria that had previously been classified as *Corynebacterium ammoniagenes*, but are presently re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are assigned to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

In particular, the *Corynebacterium glutamicum* (*C. glutamicum*) AJ12036 strain (FERM BP-734), which was isolated as a streptomycin (Sm) resistant mutant strain from a wild-type strain *C. glutamicum* ATCC 13869 is predicted to have a mutation in a gene responsible for a function involved in secretion of proteins, and shows an extremely high secretory production ability for proteins as high as about 2 to 3 times in terms of accumulation amount of proteins under optimum culture conditions, compared with the parent strain or a wild-type strain, and therefore it is preferred as a host bacterium (WO02/081694). The AJ12036 strain was originally deposited at the Fermentation Research Institute, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Mar. 26, 1984 as an international deposit, and assigned an accession number of FERM BP-734.

*Corynebacterium thermoaminogenes* AJ12340 (FERM BP-1539) was originally deposited at the Fermentation Research Institute, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Mar. 13, 1987 as an international deposit, and assigned an accession number of FERM BP-1539. *Brevibacterium flavum* AJ12418 (FERM BP-2205) was originally deposited at the Fermentation Research Institute, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 24, 1988 as an international deposit, and assigned an accession number of FERM BP-2205.

Moreover, a strain having an enhanced ability to produce a protein by secretory production may be such a coryneform bacterium as described above as a parent strain by using a mutagenesis method or a genetic recombination method, and used as a host. For example, after a parent strain is treated with ultraviolet irradiation or a chemical mutation agent such as N-methyl-N'-nitrosoguanidine, a strain having an enhanced ability to produce a protein by secretory production can be selected.

Furthermore, if a strain obtained by modifying such a strain as described above so that it does not produce a cell surface layer protein is used as a host, purification of the heterologous protein secreted in the medium or on the cell surface layer becomes easy, and therefore it is particularly preferred. Such modification can be carried out by introducing a mutation into the coding region of the cell surface layer protein or an expression control region thereof, on the chromosome by mutagenesis or genetic recombination. Examples of coryneform bacterium modified so that it does not produce a cell surface layer protein include the *C. glutamicum* YDK010 strain (WO2004/029254), which is a cell surface layer protein PS2 deficient strain of the *C. glutamicum* AJ12036 strain (FERM BP-734).

A coryneform bacterium having an ability of secretory production of a heterologous protein can be obtained by introducing the genetic construct into such a coryneform bacterium as described above so as to make the bacterium harbor the genetic construct. That is, the bacterium may be, for example, a modified strain derived from such a coryneform bacterium as described above. The bacterium may be, specifically, for example, a modified strain derived from *C.*

*glutamicum* AJ12036 (FERM BP-734) or a modified strain derived from *C. glutamicum* ATCC 13869. A modified strain derived from *C. glutamicum* AJ12036 (FERM BP-734) falls also within a modified strain derived from *C. glutamicum* ATCC 13869. The genetic construct used for the method as described herein and methods for introduction of the same will be described later.

<1-2> Decrease in the Activity of HrrSA System

The bacterium has been modified so that the activity of HrrSA system is reduced. Specifically, the bacterium has been modified so that the activity of HrrSA system is reduced as compared with a mon-modified strain. By modifying a coryneform bacterium so that the activity of HrrSA system is reduced, an ability of the bacterium to produce a heterologous protein by secretory production can be improved, that is, secretory production of a heterologous protein by the bacterium can be increased.

The bacterium can be obtained by modifying a coryneform bacterium having an ability of secretory production of a heterologous protein so that the activity of HrrSA system is reduced. The bacterium can also be obtained by modifying a coryneform bacterium so that the activity of HrrSA system is reduced, and then imparting an ability of secretory production of a heterologous protein thereto. Modifications for constructing the bacterium can be performed in any order. A strain to be used for constructing the bacterium and before being modified so that the activity of HrrSA system is reduced may or may not be able to produce a heterologous protein, on the assumption that the strain has the genetic construct for secretory expression of the heterologous protein. That is, the bacterium may also be, for example, a bacterium that has acquired an ability of secretory production of a heterologous protein due to being modified so that the activity of HrrSA system is reduced. Specifically, for example, the bacterium may also be a bacterium obtained from a strain that is not able to produce a heterologous protein by secretory production even when it has the genetic construct for secretory expression of the heterologous protein before it is modified so that the activity of HrrSA system is reduced, which came to be able to produce the heterologous protein by secretory production due to being modified so that the activity of HrrSA system is reduced.

Hereinafter, the HrrSA system and genes encoding it will be explained. The HrrSA system is one of two-component regulatory systems, and induces a response against an environmental stimulus such as presence of haem. The HrrSA system consists of a sensor kinase HrrS encoded by a hrrS gene and a response regulator HrrA encoded by a hrrA gene. The hrrS gene and the hrrA gene are also collectively referred to as "hrrSA genes". The HrrS (HrrS protein) and the HrrA (HrrA protein) are also collectively referred to as "HrrSA proteins".

The nucleotide sequences of hrrSA genes possessed by coryneform bacteria and the amino acid sequences of HrrSA proteins encoded by them can be obtained from, for example, public databases such as NCBI (National Center for Biotechnology Information). The nucleotide sequence of the hrrS gene of *C. glutamicum* ATCC 13869 is shown as SEQ ID NO: 62, and the amino acid sequence of the HrrS protein encoded by this gene is shown as SEQ ID NO: 63. The nucleotide sequence of the hrrA gene of *C. glutamicum* ATCC 13869 is shown as SEQ ID NO: 64, and the amino acid sequence of the HrrA protein encoded by this gene is shown as SEQ ID NO: 65. That is, the hrrSA gene may be, for example, genes having the nucleotide sequences shown as SEQ ID NOS: 62 and 64, respectively. Also, the HrrSA protein may be, for example, proteins having the amino acid sequences shown as SEQ ID NOS: 63 and 65, respectively. The expression "a gene or protein has a nucleotide or amino acid sequence" means that a gene or protein includes the nucleotide or amino acid sequence unless otherwise stated, and also includes cases where a gene or protein consists of the nucleotide or amino acid sequence.

The hrrSA genes each may be a variant of any of the hrrSA genes exemplified above (such as a gene having the nucleotide sequence shown as SEQ ID NO: 62 or 64), so long as the original function thereof is maintained. Similarly, the HrrSA proteins each may be a variant of any of the HrrSA proteins exemplified above (such as a protein having the amino acid sequence shown as SEQ ID NO: 63 or 65), so long as the original function thereof is maintained. Such a variant is also referred to as "conservative variant". The term "hrrSA genes" includes not only the hrrSA genes exemplified above, but also includes conservative variants thereof. Similarly, the term "HrrSA proteins" includes not only the HrrSA proteins exemplified above, but also includes conservative variants thereof. Examples of the conservative variants include, for example, homologues and artificially modified versions of the hrrSA genes and HrrSA proteins exemplified above.

The expression "the original function is maintained" means that a variant of a gene or protein has a function (such as activity or property) corresponding to the function (such as activity or property) of the original gene or protein. That is, the expression "the original function is maintained" used for each of the hrrSA genes may mean that a variant of the gene encodes a protein that maintains the original function (i.e. each of HrrSA proteins). Furthermore, the expression "the original function is maintained" used for each of the HrrSA proteins may mean that a variant of the protein has a function as each of HrrSA proteins (such as a function of a protein having the amino acid sequence shown as SEQ ID NO: 63 or 65). Furthermore, the expression "the original function is maintained" used for the HrrS protein may also mean that a variant of the protein has a function as a sensor kinase of the HrrSA system. Furthermore, the expression "the original function is maintained" used for the HrrA protein may also mean that a variant of the protein has a function as a response regulator of the HrrSA system. That is, the term "function as HrrSA proteins" may specifically refer to a function as a sensor kinase of the HrrSA system and a function as a response regulator of the HrrSA system, respectively. The term "function as a sensor kinase of the HrrSA system" may specifically refer to a function of inducing a response against an environmental stimulus in combination with a response regulator HrrA protein. The term "function as a sensor kinase of the HrrSA system" may more specifically refer to a function of sensing an environmental stimulus to be autophosphorylated, and activating the HrrA protein via transfer of phosphate group. The term "function as a response regulator of the HrrSA system" may specifically refer to a function of inducing a response against an environmental stimulus in combination with a sensor kinase HrrS protein. The term "function as a response regulator of the HrrSA system" may more specifically refer to a function of being activated via transfer of phosphate group from the HrrS protein that sensed an environmental stimulus to be autophosphorylated, and regulating (e.g. inducing or repressing) the expression of genes. Examples of the genes of which the expression is induced by the HrrSA system include genes involved in degradation of haem (such as hmuO gene) and genes encoding haem-containing proteins in the respiratory chain (such as ctaE-qcrCAB operon genes and ctaD gene). Examples of the genes of which the expression is repressed by the HrrSA system include genes involved in biosynthesis of haem (such as hemE-hemY-hemL-cg0519-ccsX-ccdA-resB-resC operon genes, hemA-hemC operon genes, and hemH gene).

Whether or not a variant of the HrrSA proteins has a function as a sensor kinase or a response regulator of the HrrSA system can be confirmed by, for example, reducing the activity of the variant in a coryneform bacterium, and confirming whether or not the expression of genes of which the expression is induced or repressed by the HrrSA system is reduced or increased in the presence of haem. Whether or not a variant of the HrrS protein has a function as a sensor kinase of the HrrSA system can also be confirmed by, for example, introducing a gene encoding the variant into a hrrS-gene-deletion strain of a coryneform bacterium, and confirming whether or not the expression of genes of which the expression is induced or repressed by the HrrSA system is increased or reduced in the presence of haem. Whether or not a variant of the HrrA protein has a function as a response regulator of the HrrSA system can also be confirmed by, for example, introducing a gene encoding the variant into a hrrA-gene-deletion strain of a coryneform bacterium, and confirming whether or not the expression of genes of which the expression is induced or repressed by the HrrSA system is increased or reduced in the presence of haem. As the hrrS-gene- or hrrA-gene-deletion strain of a coryneform bacterium, for example, a hrrS-gene- or hrrA-gene-deletion strain of *C. glutamicum* YDK010 or a hrrS-gene- or hrrA-gene-deletion strain of *C. glutamicum* ATCC 13032 can be used.

Hereinafter, examples of the conservative variants will be explained.

Homologues of the hrrSA genes and homologues of the HrrSA proteins can be easily obtained from public databases by, for example, BLAST search or FASTA search using any of the nucleotide sequences of the hrrSA genes exemplified above or any of the amino acid sequences of the HrrSA proteins exemplified above as a query sequence. Furthermore, homologues of the hrrSA genes can be obtained by, for example, PCR using a chromosome of coryneform bacteria as the template, and oligonucleotides prepared on the basis of any of the nucleotide sequences of these known hrrSA genes as primers.

The hrrSA genes each may be a gene encoding a protein having any of the amino acid sequences of the HrrSA proteins exemplified above (such as the amino acid sequence shown as SEQ ID NOS: 63 or 65), but which includes substitution, deletion, insertion, and/or addition of one or several amino acid residues at one or several positions, so long as the original function thereof is maintained. Although the number meant by the term "one or several" mentioned above may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above includes a naturally occurring mutation due to an individual difference, or a difference of species of the bacterium from which the gene is derived (mutant or variant).

The hrrSA genes each may also be a gene encoding a protein having an amino acid sequence showing a homology of, for example, 80% or more, 90% or more, 95% or more, 97% or more, or 99% or more, to the total amino acid sequence of any of the amino acid sequences of the HrrSA proteins exemplified above (such as the amino acid sequence shown as SEQ ID NO: 63 or 65), so long as the original function thereof is maintained. In this description, "homology" means "identity".

The hrrSA genes each may also be DNA that is able to hybridize under stringent conditions with a complementary sequence of any of the nucleotide sequences of the hrrSA genes exemplified above (such as the nucleotide sequence shown as SEQ ID NO: 62 or 64), or with a probe that can be prepared from the complementary sequence, so long as the original function thereof is maintained. The term "stringent conditions" refers to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe may be, for example, a part of a sequence that is complementary to the gene as described above. Such a probe can be prepared by PCR using oligonucleotides prepared on the basis of the nucleotide sequences of known genes as primers and a DNA fragment containing any of these nucleotide sequences as a template. As the probe, for example, a DNA fragment having a length of about 300 bp can be used. In such a case, the washing conditions of the hybridization may be, for example, 50° C., 2×SSC and 0.1% SDS.

Furthermore, the hrrSA genes each may be a gene having a nucleotide sequence corresponding to any of the nucleotide sequences of the hrrSA genes exemplified above or conservative variants thereof in which any codon(s) is/are replaced with respective equivalent codon(s).

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The aforementioned descriptions concerning variants of the genes and proteins can also be applied similarly to any proteins such as PhoRS proteins, cell surface layer protein, Tat secretion system, and heterologous proteins to be produced by secretory production and genes encoding them.

The phrase "the activity of HrrSA system is reduced" may mean that the degree of a response against an environmental stimulus induced via the HrrSA system is reduced. The activity of HrrSA system can be reduced by, for example, reducing the activity of HrrS protein and/or HrrA protein (i.e. either one or both of HrrS protein and HrrA protein). That is, the phrase "the activity of HrrSA system is reduced" may also mean that the activity of the HrrS protein and/or the HrrA protein is reduced. For example, at least the activity of the HrrA protein may be reduced. The phrase "the activity of HrrS protein is reduced" may mean that the function of the sensor kinase of the HrrSA system is reduced. The phrase "the activity of HrrA protein is reduced" may mean that the function of the response regulator of the HrrSA system is reduced. Hence, a reduction in the activity of HrrSA system, HrrS protein, or HrrA protein can be measured by, specifically, for example, using a reduction or increase in the expression of genes of which the expression is induced or repressed by the HrrSA system in the presence of haem as an index. Also, the phrase "the activity of HrrSA system is reduced" may particularly mean that the number of molecules of the HrrSA system per cell is reduced. Similarly, the phrase "the activity of HrrS protein and/or HrrA protein is reduced" may particularly mean that the number of molecules of the HrrS protein and/or HrrA protein per cell is reduced. Methods for reducing the activity of a protein such as the HrrSA proteins will be explained later. The activity of HrrSA proteins can be reduced by, for example, reducing the expression of genes encoding the proteins (hrrSA genes), or by disrupting the hrrSA genes. Furthermore, in a two-component regulatory system, when a sensor kinase senses a stimulus, a specific histidine residue thereof is autophosphorylated, and a signal is transduced via transfer of the phosphate group to a specific aspartic acid residue of a response regulator. Hence, the activity of HrrSA system, specifically the activity of HrrS protein, can also be reduced by, for example, replacing or deleting the histidine residue to be autophosphorylated of the HrrS protein. Furthermore, the activity of HrrSA system, the activity of HrrA protein, can also be reduced by, for example, replacing or deleting the aspartic acid residue of the HrrA protein, to which the phosphate group is transferred from the autophosphorylated histidine residue of the HrrS protein. This histidine residue is the histidine residue at position 217 (H217) of the HrrS protein. The term "H217 of the HrrS protein" specifically means the histidine residue corresponding to H217 of SEQ ID NO: 63. This aspartic acid residue is the aspartic acid residue at position 54 (D54) of the HrrA protein. The term "D54 of the HrrA protein" specifically means the aspartic acid residue corresponding to D54 of SEQ ID NO: 65. The descriptions concerning the position of the "amino acid residue at position X of the wild-type PhoS protein" described herein can be applied similarly to the position of the "H217 of the HrrS protein" or "D54 of the HrrA protein" in any chosen HrrSA proteins. This histidine or aspartic acid residue may be replaced or deleted solely or in combination with a surrounding region. That is, for example, only this histidine or aspartic acid residue may be replaced or deleted, or a region including this histidine or aspartic acid residue may be replaced or deleted.

<1-3> Other Characteristics

The bacterium may have desired characteristics, so long as it can produce a heterologous protein by secretory production. For example, the activity of a cell surface layer protein may have been reduced in the bacterium (WO2013/065869, WO2013/065772, WO2013/118544, and WO2013/062029). For example, the bacterium may have been modified so that the activity of a penicillin-binding protein is reduced (WO2013/065869). For example, the bacterium may have been modified so that the expression of a gene encoding a metallopeptidase is increased (WO2013/065772). For example, the bacterium may have been modified so as to have a mutant ribosomal protein Si gene (mutant rpsA gene) (WO2013/118544). For example, the bacterium may have been modified so as to have a mutant phoS gene (WO2016/171224). For example, the Tat secretion system may be enhanced in the bacterium. These characteristics or modifications can be used solely or in any appropriate combination.

<1-3-1> Introduction of Mutant phoS Gene

The bacterium may have been modified so as to harbor a mutant phoS gene. The expression "to harbor a mutantphoS gene" is also referred to as "to have a mutantphoS gene" or "to have a mutation in a phoS gene". In addition, the expression "to harbor a mutant phoS gene" is also referred to as "to have a mutant PhoS protein" or "to have a mutation in a PhoS protein".

Hereinafter, the phoS gene and the PhoS protein will be explained. The phoS gene is a gene encoding a PhoS protein, which is a sensor kinase of the PhoRS system. The PhoRS system is one of two-component regulatory systems, and induces a response against phosphate depletion. The PhoRS system consists of a sensor kinase PhoS encoded by a phoS gene and a response regulator PhoR encoded by a phoR gene.

A PhoS protein having the "specific mutation" is also referred to as "mutant PhoS protein", and a gene encoding it is also referred to as "mutant phoS gene". The mutant phoS gene is, in other words, a phoS gene having the "specific mutation". Furthermore, a PhoS protein not having the "specific mutation" is also referred to as "wild-type PhoS protein", and a gene encoding it is also referred to as "wild-type phoS gene". The wild-type phoS gene is, in other words, a phoS gene not having the "specific mutation". The term "wild-type" referred to herein is used for convenience to distinguish "wild-type" ones from "mutant" ones, and "wild-type" ones are not limited to those obtained as natural substances, so long as those do not have the "specific mutation". The "specific mutation" will be described later.

Examples of the wild-type phoS gene include, for example, phoS genes of coryneform bacteria. Specific examples of the phoS genes of coryneform bacteria include, for example, the phoS genes of *C. glutamicum* YDK010, *C. glutamicum* ATCC 13032, *C. glutamicum* ATCC 14067, *C. callunae*, *C. crenatum*, and *C. efficiens*. The nucleotide sequence of the phoS gene of *C. glutamicum* YDK010 is shown as SEQ ID NO: 3. The amino acid sequences of the wild-type PhoS proteins encoded by these phoS genes are shown as SEQ ID NOS: 4, 26, 27, 28, 29, and 30, respectively.

The wild-type phoS gene may be a variant of any of the wild-type phoS genes exemplified above, so long as it does not have the "specific mutation" and the original function thereof is maintained. Similarly, the wild-type PhoS protein may be a variant of any of the wild-type PhoS proteins exemplified above, so long as it does not have the "specific mutation" and the original function thereof is maintained. That is, the term "wild-type phoS gene" includes not only the wild-type phoS genes exemplified above, but also includes conservative variants thereof that do not have the "specific mutation". Similarly, the term "wild-type PhoS protein" includes not only the wild-type PhoS proteins exemplified above, but also includes conservative variants thereof that do not have the "specific mutation". The aforementioned descriptions concerning conservative variants of the HrrSA proteins and the hrrSA genes can be applied similarly to variants of the wild-type PhoS protein and the wild-type phoS gene. For example, the wild-type phoS gene may also be a gene encoding a protein having any of the aforementioned amino acid sequences, but which includes substitution, deletion, insertion, and/or addition of one or several amino acid residues at one or several positions, so long as it does not have the "specific mutation" and the original function thereof is maintained.

Incidentally, the expression "the original function is maintained" used for the wild-type PhoS may mean that a variant of the protein has a function as a PhoS protein (such as a function of a protein consisting of the amino acid sequence shown as SEQ ID NO: 4, 26, 27, 28, 29, or 30). Furthermore, the expression "the original function is maintained" used for the wild-type PhoS protein may also mean that a variant of the protein has a function as a sensor kinase of the PhoRS system. That is, the term "function as a PhoS protein" may specifically refer to a function as a sensor kinase of the PhoRS system. The term "function as a sensor kinase of the PhoRS system" may specifically refer to a function of inducing a response against phosphate depletion in the environment in combination with a response regulator PhoR protein. The term "function as a sensor kinase of the PhoRS system" may more specifically refer to a function of sensing phosphate depletion in the environment to be autophosphorylated, and activating the PhoR protein via transfer of phosphate group.

Whether or not a variant of the PhoS protein has a function as a sensor kinase of the PhoRS system can be confirmed by, for example, introducing a gene encoding the variant into aphoS-gene-deletion strain of a coryneform bacterium, and confirming whether or not responsiveness against phosphate depletion is complemented. Complementation of responsiveness against phosphate depletion can be detected, for example, as improvement of growth under phosphate depletion conditions, or as induction of the expression of genes of which the expression is known to be induced under phosphate depletion conditions (J. Bacteriol., 188, 724-732 (2006)). As the phoS-gene-deletion strain of a coryneform bacterium, for example, a phoS-gene-deletion strain of *C. glutamicum* YDK010 or aphoS-gene-deletion strain of *C. glutamicum* ATCC 13032 can be used.

A histidine residue that is autophosphorylated can be conserved. That is, a conservative mutation can occur at an amino acid residue other than the histidine residue that is autophosphorylated. The term "histidine residue that is autophosphorylated" refers to a histidine residue at position 276 of the wild-type PhoS protein. Furthermore, for example, the wild-type PhoS protein has a conservative sequence of the wild-type PhoS proteins exemplified above. That is, a conservative mutation occurs at, for example, an amino acid residue not conserved in the wild-type PhoS proteins exemplified above.

The mutant PhoS protein has the "specific mutation" in the amino acid sequence of such a wild-type PhoS protein as described above.

That is, in other words, the mutant PhoS protein may be identical to any of the wild-type PhoS proteins exemplified above or conservative variants thereof except that the mutant PhoS protein has the "specific mutation". Specifically, the mutant PhoS protein may be, for example, a protein having the amino acid sequence shown in SEQ ID NO: 4, 26, 27, 28, 29, or 30 except that the mutant PhoS protein has the "specific mutation". Specifically, the mutant PhoS protein may also be, for example, a protein having the amino acid sequence shown in SEQ ID NO: 4, 26, 27, 28, 29, or 30 but including substitution, deletion, insertion, and/or addition of one or several amino acid residues, except that the mutant PhoS protein has the "specific mutation". Specifically, the mutant PhoS protein may also be, for example, a protein showing a homology of 80% or more, 90% or more, 95% or more, 97% or more, or 99% or more, to the amino acid sequence shown in SEQ ID NO: 4, 26, 27, 28, 29, or 30 except that the mutant PhoS protein has the "specific mutation".

Furthermore, in other words, the mutant PhoS protein may be a variant of any of the wild-type PhoS proteins exemplified above having the "specific mutation", and further including a conservative mutation at a site other than that of the "specific mutation". Specifically, the mutant PhoS protein may be, for example, a protein having the amino acid sequence shown in SEQ ID NO: 4, 26, 27, 28, 29, or 30 but having the "specific mutation", and further including substitution, deletion, insertion, and/or addition of one or several amino acid residues at a site other than that of the "specific mutation".

The mutant phoS gene is not particularly limited so long as it encodes such a mutant PhoS protein as described above.

Hereinafter, the "specific mutation" of the mutant PhoS protein will be explained.

The "specific mutation" is not particularly limited, so long as it is a mutation that changes the amino acid sequence of such a wild-type PhoS protein described above, and that is effective for secretory production a heterologous protein.

The "specific mutation" can be a mutation that improves the secretory production amount of a heterologous protein. The expression "to improve the secretory production amount of a heterologous protein" means that a coryneform bacterium modified so as to have a mutant phoS gene (modified strain) is able to produce the heterologous protein by secretory production in an amount larger than that obtainable with a non-modified strain. The "non-modified strain" refers to a control strain not having the "specific mutation" in the phoS gene, i.e. a control strain not having any mutant phoS gene, and it may be, for example, a wild-type strain or a parent strain. Although the degree of increase meant by the expression "to produce a heterologous protein by secretory production in an amount larger than that obtainable with a non-modified strain" is not particularly limited so long as the secretory production amount of the heterologous protein is increased compared with that obtainable with a non-modified strain, the expression may mean that the heterologous protein is produced by secretory production in an amount of, for example, 1.1 times or more, 1.2 times or more, 1.3 times or more, 2 times or more, or 5 times or more, of that obtainable with a non-modified strain, in terms of the accumulation amount in the medium and/or on the cell surface layer. In addition, the expression "to produce a heterologous protein by secretory production in an amount larger than that obtainable with a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB. Incidentally, the expression "to improve the secretory production amount of a heterologous protein" does not necessarily mean that the secretory production amount of every heterologous protein is improved, and it is sufficient that the secretory production amount of a heterologous protein chosen as the target of secretory production is improved. The expression "to improve the secretory production amount of a heterologous protein" may specifically mean, for example, that the secretory production amount of a heterologous protein described in the Example section is improved.

Whether a certain mutation is a mutation that improves the secretory production amount of a heterologous protein can be confirmed by, for example, preparing a strain modified so as to have a gene encoding the PhoS protein having the certain mutation from a strain belonging to a coryneform bacterium, quantifying the amount of the heterologous protein produced by secretory production when the strain is cultured in a medium, and comparing it with the amount of the heterologous protein produced by secretory production when the strain before the modification (non-modified strain) is cultured in the medium.

Examples of the change of the amino acid sequence include substitution of an amino acid residue. That is, the "specific mutation" can be a mutation of replacing an amino acid residue with another amino acid residue. The amino acid residue substituted by the "specific mutation" may be one residue, or may be a combination of two or more residues. The amino acid residue substituted by the "specific mutation" may be an amino acid residue other than the histidine residue that is autophosphorylated. The amino acid residue substituted by the "specific mutation" may be an amino acid residue in the HisKA domain other than the histidine residue that is autophosphorylated. The term "histidine residue that is autophosphorylated" refers to a histidine residue at position 276 of the wild-type PhoS protein. The term "HisKA domain" refers to a region consisting of amino acid residues at positions 266-330 of the wild-type PhoS protein. The amino acid residue substituted by the "specific mutation" may be a tryptophan residue at position 302 of the wild-type PhoS protein (W302).

In the aforementioned mutation, examples of the amino acid residue after substitution include K(Lys), R(Arg), H(His), A(Ala), V(Val), L(Leu), I(Ile), G(Gly), S(Ser), T(Thr), P(Pro), F(Phe), W(Trp), Y(Tyr), C(Cys), M(Met), D(Asp), E(Glu), N(Asn), and Q(Gln), provided that the amino acid residue after substitution is other than the original one. As the amino acid residue after substitution, for example, one resulting in improvement in the secretory production amount of a heterologous protein can be chosen.

When substitution occurs at W302, examples of the amino acid residue after substitution include amino acid residues other than aromatic amino acid and histidine residues. Specific examples of the "amino acid residues other than aromatic amino acid and histidine residues" include K(Lys), R(Arg), A(Ala), V(Val), L(Leu), I(Ile), G(Gly), S(Ser), T(Thr), P(Pro), C(Cys), M(Met), D(Asp), E(Glu), N(Asn), and Q(Gln). More specific examples of the "amino acid residues other than aromatic amino acid and histidine residues" include K(Lys), A(Ala), V(Val), S(Ser), C(Cys), M(Met), D(Asp), and N(Asn).

Incidentally, the term "specific mutation" used for the phoS gene refers to a mutation on the nucleotide sequence thereof that results in such a "specific mutation" as described above into the encoded PhoS protein.

The "amino acid residue at position X of the wild-type PhoS protein" refers to an amino acid residue corresponding to the amino acid residue at position X in SEQ ID NO: 4. For example, "W302" refers to an amino acid residue corresponding to the tryptophan residue at position 302 in SEQ ID NO: 4. The aforementioned positions of amino acid residues indicate relative positions, and the absolute positions thereof may shift due to deletion, insertion, addition, or the like of an amino acid residue or residues. For example, if one amino acid residue is deleted or inserted at a position on the N-terminal side of position X in the amino acid sequence shown as SEQ ID NO: 4, the amino acid residue originally at position X is relocated at position X-1 or X+1 counted from the N-terminus, however, it is still regarded as the "amino acid residue at position X of the wild-type PhoS protein". Specifically, for example, "W302" refers to the tryptophan residue at positions 302, 302, 302, 321, 275, and 286, respectively, in the amino acid sequences of wild-type PhoS proteins shown in SEQ ID NOS: 4, 26, 27, 28, 29, and 30. Furthermore, the "histidine residue at position 276 of the wild-type PhoS protein (histidine residue that is autophosphorylated)" refers to the histidine residue at positions 276, 276, 276, 295, 249, and 260, respectively, in the amino acid sequences of wild-type PhoS proteins shown in SEQ ID NOS: 4, 26, 27, 28, 29, and 30. Furthermore, the "region consisting of amino acid residues at positions 266-330 of the wild-type PhoS protein (HisKA domain)" refers to the region consisting of amino acid residues at positions 266-330, 266-330, 266-330, 285-349, 239-303, and 250-314, respectively, in the amino acid sequences of wild-type PhoS proteins shown in SEQ ID NOS: 4, 26, 27, 28, 29, and 30.

Incidentally, while "W302" referred to herein is typically a tryptophan residue, it may also be other than a tryptophan residue. That is, when the wild-type PhoS protein has an amino acid sequence other than the amino acid sequences shown in SEQ ID NOS: 4, 26, 27, 28, 29, and 30, "W302" can be other than a tryptophan residue. Hence, for example, the "mutation replacing W302 with a cysteine residue" includes not only a mutation, when "W302" is a tryptophan residue, for replacing this tryptophan residue with a cysteine residue, but also includes a mutation, when "W302" is K(Lys), R(Arg), H(His), A(Ala), V(Val), L(Leu), I(Ile), G(Gly), S(Ser), T(Thr), P(Pro), F(Phe), Y(Tyr), M(Met), D(Asp), E(Glu), N(Asn), or Q(Gln), for replacing this residue with a cysteine residue. The same can be applied similarly to the other mutations.

Which amino acid residue is the "amino acid residue corresponding to the amino acid residue at position X in SEQ ID NO: 4" in the amino acid sequence of an arbitrary PhoS protein can be determined by alignment between the amino acid sequence of the arbitrary PhoS protein and the amino acid sequence of SEQ ID NO: 4. The alignment can be performed by, for example, using known gene analysis software. Specific examples of such software include DNA-SIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

The mutant phoS gene can be obtained by, for example, modifying a wild-type phoS gene so that the encoded PhoS protein has the aforementioned "specific mutation". The wild-type phoS gene to be modified can be obtained by, for example, cloning from an organism having the wild-type phoS gene, or chemical synthesis. Furthermore, the mutant phoS gene can also be obtained without using a wild-type phoS gene. For example, the mutant phoS gene may be directly obtained by chemical synthesis. The obtained mutant phoS gene may be further modified before use.

Genes can be modified by known methods. For example, an objective mutation can be introduced into a target site of DNA by the site-specific mutagenesis method. Examples of the site-specific mutagenesis method include a method of using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. In Enzymol., 154, 350 (1987); Kunkel, T. A. et al., Meth. in Enzymol., 154, 367 (1987)).

Hereinafter, methods for modifying a coryneform bacterium so as to have a mutant phoS gene will be explained.

A coryneform bacterium can be modified so as to have a mutant phoS gene by introducing the mutant phoS gene into the coryneform bacterium. A coryneform bacterium can be modified so as to have a mutant phoS gene also by introducing a mutation into the phoS gene on the chromosome of the coryneform bacterium. A mutation can be introduced into a gene on a chromosome by natural mutation, mutagenesis treatment, or genetic engineering means.

Methods for introducing a mutant phoS gene into a coryneform bacterium are not particularly limited. It is sufficient that the mutant phoS gene is harbored by the bacterium so that it can be expressed under control of a promoter that functions in a coryneform bacterium. The promoter may be a promoter derived from the host, or a heterogenous promoter. The promoter may be the native promoter of the phoS gene, or a promoter of another gene. In the bacterium, the mutant phoS gene may be present on a vector that autonomously replicates out of the chromosome, such as plasmid, or may be incorporated into the chromosome. The bacterium may have only one copy of the mutant phoS gene, or two or more copies of the mutant phoS gene. The bacterium may have only one kind of mutant phoS gene, or two or more kinds of mutant phoS genes. The mutant phoS gene can be introduced, for example, in the same manner as that for introduction of a gene in methods for increasing the expression of a gene described below, or for introduction of the genetic construct described below.

The bacterium may or may not have the wild-type phoS gene. One example is that the bacterium does not have the wild-type phoS gene.

A coryneform bacterium not having the wild-type phoS gene can be obtained by disrupting the wild-type phoS gene on the chromosome. The wild-type phoS gene can be disrupted by known methods. Specifically, the wild-type phoS gene can be disrupted by, for example, deleting a part or the whole of the promoter region and/or the coding region of the wild-type phoS gene.

Furthermore, by replacing the wild-type phoS gene on the chromosome with a mutant phoS gene, a coryneform bacterium modified so that it does not have the wild-type phoS gene and has the mutant phoS gene can be obtained. Examples of methods for performing such gene substitution include, for example, a method of using a linear DNA such as a method called "Red driven integration" (Datsenko, K. A, and Wanner, B. L., Proc. Natl. Acad. Sci. USA, 97:6640-6645 (2000)), a method of utilizing the Red driven integration in combination with an excision system derived from X. phage (Cho, E. H., Gumport, R. I., Gardner, J. F., J. Bacteriol., 184:5200-5203 (2002)) (refer to WO2005/010175), a method of using a plasmid including a temperature sensitive replication origin, a method of using a plasmid capable of conjugative transfer, a method of utilizing a suicide vector not including a replication origin that functions in a host (U.S. Pat. No. 6,303,383, Japanese Patent Laid-open (Kokai) No. 05-007491), and so forth.

The PhoS protein functions, i.e. induces a response against phosphate depletion in the environment, in combination with a response regulator PhoR protein. Hence, the bacterium has a phoR gene so that the mutant PhoS protein functions. The phoR gene is a gene encoding a PhoR protein, which is a response regulator of the PhoRS system. The expression "to have a phoR gene" is also referred to as "to have a PhoR protein". Typically, it is sufficient that the PhoR protein inherently possessed by the bacterium functions in combination with the mutant PhoS protein. Alternatively, the bacterium may be introduced with an appropriate phoR gene, in addition to or instead of the phoR gene inherently possessed by the bacterium. The phoR gene to be introduced is not particularly limited, as long as it encodes a PhoR protein that functions in combination with the mutant PhoS protein.

Examples of the phoR gene include, for example, phoR genes of coryneform bacteria. Specific examples of the phoR genes of coryneform bacteria include, for example, the phoR genes of *C. glutamicum* YDK010, *C. glutamicum* ATCC 13032, *C. glutamicum* ATCC 14067, *C. callunae*, *C. crenatum*, and *C. efficiens*. The nucleotide sequence of the phoR gene of *C. glutamicum* ATCC 13032 and the amino acid sequence of the PhoR protein of the same are shown as SEQ ID NO: 31 and 32, respectively.

The phoR gene may be a variant of any of the phoR genes exemplified above, so long as the original function thereof is maintained. Similarly, the PhoR protein may be a variant of any of the PhoR proteins exemplified above, so long as the original function thereof is maintained. That is, the term "phoR gene" includes not only the phoR genes exemplified above, but also includes conservative variants thereof. Similarly, the term "PhoR protein" includes not only the PhoR proteins exemplified above, but also includes conservative variants thereof. The aforementioned descriptions concerning conservative variants of the HrrSA proteins and the hrrSA genes can be applied similarly to variants of the phoR gene and PhoR protein. For example, the phoR gene may be a gene encoding a protein having the aforementioned amino acid sequence, but including substitution, deletion, insertion, and/or addition of one or several amino acid residues at one or several positions, so long as the original function is maintained. Incidentally, the expression "the original function is maintained" used for the PhoR protein may mean that a variant of the protein has a function as a PhoR protein (such as a function of a protein consisting of the amino acid sequence shown as SEQ ID NO: 32). Furthermore, the expression "the original function is maintained" used for the PhoR protein may also mean that a variant of the protein has a function as a response regulator of the PhoRS system. That is, the term "function as a PhoR protein" may specifically refer to a function as a response regulator of the PhoRS system. The term "function as a response regulator of the PhoRS system" may specifically refer to a function of inducing a response against phosphate depletion in the environment in combination with a sensor kinase PhoS protein. The term "function as a response regulator of the PhoRS system" may more specifically refer to a function of being activated via transfer of phosphate group from the PhoS protein that sensed phosphate depletion in the environment to be autophosphorylated, and regulating the expression of genes that respond to phosphate depletion in the environment.

Whether or not a variant of the PhoR protein has a function as a response regulator of the PhoRS system can be confirmed by, for example, introducing a gene encoding the variant into aphoR-gene-deletion strain of a coryneform bacterium, and confirming whether or not responsiveness against phosphate depletion is complemented. Complementation of responsiveness against phosphate depletion can be detected, for example, as improvement of growth under phosphate depletion conditions, or as induction of the expression of genes of which the expression is known to be induced under phosphate depletion conditions (J. Bacteriol., 188, 724-732 (2006)). As the phoR-gene-deletion strain of a coryneform bacterium, for example, a phoR-gene-deletion strain of *C. glutamicum* YDK010 or aphoR-gene-deletion strain of *C. glutamicum* ATCC 13032 can be used.

<1-3-2> Reduction in Activity of Cell Surface Layer Protein

The bacterium may be a bacterium of which the activity(s) of cell surface layer protein(s) is/are reduced. Specifically, the bacterium may be a bacterium of which the activity(s) of cell surface layer protein(s) is/are reduced as compared with a non-modified strain. The phrase "the activity of a cell surface layer protein is reduced" may particularly mean that the number of molecules of the cell surface layer protein per cell is reduced. Hereinafter, the cell surface layer proteins and genes encoding them will be explained.

The cell surface layer protein is a protein constituting the surface layer (S layer) of bacteria or archaea. Examples of cell surface layer proteins of coryneform bacteria include PS1 and PS2 (CspB) of *C. glutamicum* (Japanese Patent Laid-open (Kohyo) No. 6-502548), and SlpA (CspA) of *C. stationis* (Japanese Patent Laid-open (Kokai) No. 10-108675). It is preferable to reduce the activity of the PS2 protein among these.

The nucleotide sequence of the cspB gene of *C. glutamicum* ATCC 13869 and the amino acid sequence of the PS2 protein (CspB protein) encoded by the gene are shown in SEQ ID NOS: 33 and 34, respectively.

Furthermore, for example, amino acid sequences of CspB homologues were reported for 28 strains of *C. glutamicum* (J. Biotechnol., 112, 177-193 (2004)). These 28 strains of *C. glutamicum* and the GenBank accession numbers of the cspB gene homologues in NCBI database are exemplified below (the GenBank accession numbers are shown in the parentheses).

*C. glutamicum* ATCC 13058 (AY524990)
*C. glutamicum* ATCC 13744 (AY524991)
*C. glutamicum* ATCC 13745 (AY524992)
*C. glutamicum* ATCC 14017 (AY524993)
*C. glutamicum* ATCC 14020 (AY525009)
*C. glutamicum* ATCC 14067 (AY524994)
*C. glutamicum* ATCC 14068 (AY525010)
*C. glutamicum* ATCC 14747 (AY525011)
*C. glutamicum* ATCC 14751 (AY524995)
*C. glutamicum* ATCC 14752 (AY524996)
*C. glutamicum* ATCC 14915 (AY524997)
*C. glutamicum* ATCC 15243 (AY524998)
*C. glutamicum* ATCC 15354 (AY524999)
*C. glutamicum* ATCC 17965 (AY525000)
*C. glutamicum* ATCC 17966 (AY525001)
*C. glutamicum* ATCC 19223 (AY525002)
*C. glutamicum* ATCC 19240 (AY525012)
*C. glutamicum* ATCC 21341 (AY525003)
*C. glutamicum* ATCC 21645 (AY525004)
*C. glutamicum* ATCC 31808 (AY525013)
*C. glutamicum* ATCC 31830 (AY525007)
*C. glutamicum* ATCC 31832 (AY525008)
*C. glutamicum* LP-6 (AY525014)
*C. glutamicum* DSM20137 (AY525015)
*C. glutamicum* DSM20598 (AY525016)
*C. glutamicum* DSM46307 (AY525017)
*C. glutamicum* 22220 (AY525005)
*C. glutamicum* 22243 (AY525006)

Since the nucleotide sequence of a gene encoding a cell surface layer protein may differ depending on species or strain to which the coryneform bacterium belongs, the gene encoding a cell surface layer protein may be a variant of any of genes encoding the cell surface layer proteins exemplified above, so long as the original function thereof is maintained. Similarly, the cell surface layer protein may be a variant of any of the cell surface layer proteins exemplified above, so long as the original function thereof is maintained. That is, the term "cspB gene" includes not only the cspB genes exemplified above, but also includes conservative variants thereof. Similarly, the term "CspB protein" includes not only the CspB proteins exemplified above, but also includes conservative variants thereof. The aforementioned descriptions concerning conservative variants of the HrrSA proteins and the hrrSA genes can be applied similarly to variants of the cell surface layer protein and the gene encoding it. For example, the gene encoding the cell surface layer protein may be a gene encoding a protein having the aforementioned amino acid sequence, but including substitution, deletion, insertion, and/or addition of one or several amino acid residues at one or several positions, so long as the original function is maintained. Incidentally, the expression "original function is maintained" used for the cell surface layer protein may mean that the protein has a property that if the activity of the protein is reduced in a coryneform bacterium, the secretory production amount of a heterologous protein is increased compared with that obtainable with a non-modified strain.

The "property that if the activity of the protein is reduced in a coryneform bacterium, the secretory production amount of a heterologous protein is increased compared with that obtainable with a non-modified strain" refers to a property imparting an ability to produce a heterologous protein by secretory production in an amount larger than that obtainable with a non-modified strain to a coryneform bacterium when the activity thereof is reduced in the coryneform bacterium. The "non-modified strain" refers to a control strain of which the activity(s) of cell surface layer protein(s) is/are not reduced, and it may be, for example, a wild-type strain or a parent strain. Although the degree of increase meant by the expression "to produce a heterologous protein by secretory production in an amount larger than that obtainable with a non-modified strain" is not particularly limited so long as the secretory production amount of the heterologous protein is increased compared with that obtainable with a non-modified strain, the expression may mean that the heterologous protein is produced by secretory production in an amount of, for example, 1.1 times or more, 1.2 times or more, 1.3 times or more, or 2 times or more, of that obtainable with a non-modified strain, in terms of the accumulation amount in the medium and/or on the cell surface layer. In addition, the expression "to produce a heterologous protein by secretory production in an amount larger than that obtainable with a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB.

Whether a protein has a property that if the activity of the protein is reduced in a coryneform bacterium, the secretory production amount of a heterologous protein is increased compared with that obtainable with a non-modified strain can be confirmed by preparing a strain modified so that the activity of the protein is reduced from a strain belonging to the coryneform bacteria, quantifying the secretory production amount of the heterologous protein observed when the modified strain is cultured in a medium, and comparing the quantified amount with the secretory production amount of the heterologous protein observed when the strain before being modified (un-modified strain) is cultured in the medium.

The expression "activity of a cell surface layer protein is reduced" includes a case where a coryneform bacterium has been modified so that the activity of a cell surface layer protein is reduced and a case where the activity of a cell surface layer protein is inherently reduced in a coryneform bacterium. The "case where activity of a cell surface layer protein is inherently reduced in a coryneform bacterium" includes a case where a coryneform bacterium is inherently deficient in a cell surface layer protein. That is, examples of a coryneform bacterium in which the activity of a cell surface layer protein is reduced include a coryneform bacterium that is inherently deficient in a cell surface layer protein. Examples of the "case where a coryneform bacterium is inherently deficient in a cell surface layer protein" include a case where a coryneform bacterium is inherently deficient in the gene encoding a cell surface layer protein. The expression "a coryneform bacterium is inherently deficient in a cell surface layer protein" may mean that a coryneform bacterium is inherently deficient in one or more proteins selected from cell surface layer protein(s) found in other strain(s) of the species to which the coryneform bacterium belongs. For example, "C. glutamicum is inherently deficient in a cell surface layer protein" may mean that a C. glutamicum strain is inherently deficient in one or more proteins selected from cell surface layer protein(s) found in other C. glutamicum strain(s), i.e. for example, deficient in PS1 and/or PS2 (CspB). Examples of the coryneform bacterium that is inherently deficient in a cell surface layer protein include C. glutamicum ATCC 13032, which is inherently deficient in the cspB gene.

<1-3-3> Protein Secretion System

The bacterium as described herein has a protein secretion system. The protein secretion system is not particularly limited, so long as it can secrete an objective heterologous protein. Examples of the protein secretion system include Sec system (Sec secretion system) and Tat system (Tat secretion system). The bacterium may have been modified so that the protein secretion system is enhanced. For example, the bacterium may have been modified so that the expression of one or more genes selected from genes encoding the Tat secretion system is increased. such a modification is also referred to as "enhancement of the Tat secretion system". Enhancement of the Tat secretion system is a particular example for cases of producing a heterologous protein by secretory production using a Tat-dependent signal peptide. Methods for increasing the expression of genes encoding the Tat secretion system are described in Japanese Patent No. 4730302.

Examples of the genes encoding the Tat secretion system include tatA, tatB, tatC, and tatE genes.

Specific examples of the genes encoding the Tat secretion system include tatA, tatB, and tatC genes of C. glutamicum. The tatA, tatB, and tatC genes of C. glutamicum ATCC 13032 correspond to the complementary sequence of positions 1571065-1571382, the sequence of positions 1167110-1167580, and the complementary sequence of positions 1569929-1570873 in the genome sequence registered as GenBank accession NC_003450 (VERSION NC 003450.3 GI:58036263) in NCBI database, respectively. The TatA, TatB, and TatC proteins of C. glutamicum ATCC 13032 have been registered as GenBank accession NP_600707 (version NP_600707.1 GI:19552705, locus tag="NCgl1434"), GenBank accession NP_600350 (version NP_600350.1 GI:19552348, locus tag="NCgl1077"), and GenBank accession NP_600706 (version NP_600706.1 GI:19552704, locus tag="NCgl1433"), respectively. The nucleotide sequences of the tatA, tatB, and tatC genes of C. glutamicum ATCC 13032 and the amino acid sequences of the TatA, TatB, and TatC proteins of the same are shown as SEQ ID NOS: 35-40.

Specific examples of the genes encoding the Tat secretion system also include tatA, tatB, tatC, and tatE genes of *E. coli*. The tatA, tatB, tatC, and tatE genes of *E. coli* K-12 MG1655 correspond to the sequence of positions 4019968-4020237, the sequence of positions 4020241-4020756, the sequence of positions 4020759-4021535, and the sequence of positions 658170-658373 in the genome sequence registered as GenBank accession NC_000913(VERSION NC_000913.2 GI:49175990) in NCBI database, respectively. The TatA, TatB, TatC, and TatE proteins of *E. coli* K-12 MG1655 have been registered as GenBank accession NP_418280 (version NP_418280.4 GI:90111653, locus tag="b3836"), GenBank accession YP_026270 (version YP_026270.1 GI:49176428, locus tag="b3838"), GenBank accession NP_418282 (version NP_418282.1 GI:16131687, locus tag="b3839"), and GenBank accession NP_415160 (version NP_415160.1 GI:16128610, locus tag="b0627"), respectively.

The gene encoding the Tat secretion system may be a variant of any of the genes encoding the Tat-secretion-system exemplified above, so long as the original function thereof is maintained. Similarly, the Tat-secretion-system may be a variant of any of the Tat-secretion-systems exemplified above, so long as the original function thereof is maintained. That is, the terms "tatA gene", "tatB gene", "tatC gene", and "tatE gene" include not only the tatA, tatB, tatC, and tatE genes exemplified above, respectively, but also includes conservative variants thereof. Similarly, the terms "TatA protein", "TatB protein", "TatC protein", and "TatE protein" include not only the TatA, TatB, TatC, and TatE proteins exemplified above, respectively, but also includes conservative variants thereof. The aforementioned descriptions concerning conservative variants of the HrrSA proteins and the hrrSA genes can be applied similarly to variants of the Tat-secretion-system and the gene encoding it. For example, the gene encoding the Tat-secretion-system may be a gene encoding a protein having any of the aforementioned amino acid sequences, but including substitution, deletion, insertion, and/or addition of one or several amino acid residues at one or several positions, so long as the original function is maintained. Incidentally, the expression "original function is maintained" used for the Tat-secretion-system may mean that the system has a function of secreting a protein fused with a Tat-dependent signal peptide at the N-terminus out of the cell.

<1-4> Method for Reducing Activity of Protein

Hereinafter, methods for reducing the activity of a protein such as the HrrSA proteins will be explained. The methods for reducing the activity of a protein described below can also be utilized for disruption of the wild-type PhoS protein.

The expression "the activity of a protein is reduced" means that the activity of the protein is reduced as compared with a non-modified strain. Specifically, the expression "the activity of a protein is reduced" means that the activity of the protein per cell is reduced as compared with that of a non-modified strain. The term "non-modified strain" used herein refers to a control strain that has not been modified so that the activity of an objective protein is reduced. Examples of the non-modified strain include a wild-type strain and parent strain. Specific examples of the non-modified strain include the respective type strains of the species of bacteria. Specific examples of the non-modified strain also include strains exemplified above in relation to the description of coryneform bacteria. That is, in an embodiment, the activity of a protein may be reduced as compared with a type strain, i.e. the type strain of the species to which the bacterium belongs. In another embodiment, the activity of a protein may also be reduced as compared with *C. glutamicum* ATCC 13032. In another embodiment, the activity of a protein may also be reduced as compared with *C. glutamicum* ATCC 13869. In another embodiment, the activity of a protein may also be reduced as compared with *C. glutamicum* AJ12036 (FERM BP-734). In another embodiment, the activity of a protein may also be reduced as compared with *C. glutamicum* YDK010. The state that "the activity of a protein is reduced" also includes a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the gene (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" means that the expression of the gene is reduced as compared with a non-modified strain. Specifically, the expression "the expression of a gene is reduced" means that the expression of the gene per cell is reduced as compared with that of a non-modified strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence are modified. The transcription efficiency of a gene can be reduced by, for example, replacing the promoter of the gene on a chromosome with a weaker promoter. The term "weaker promoter" means a promoter providing an attenuated transcription of a gene compared with an inherently existing wild-type promoter of the gene. Examples of weaker promoters include, for example, inducible promoters. That is, an inducible promoter may function as a weaker promoter under a non-induced condition, such as in the absence of the corresponding inducer. Furthermore, a partial region or the whole region of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" refers to deletion of a partial or entire region of the coding region of the gene. Furthermore, the whole of a gene including sequences upstream and downstream from the coding region of the gene on a chromosome may be deleted. The sequences upstream and downstream from the coding region of the gene may include, for example, an expression control sequence of the gene. The region to be deleted may be any region such as an N-terminal region (region encoding an N-terminal region of a protein), an internal region, or a C-terminal region (region encoding a C-terminal region of a protein), so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, the reading frames of the sequences upstream and downstream from the region to be deleted do not have to be the same. Inconsistency of reading frames may cause a frameshift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. Reading frames of the sequences upstream and downstream from the insertion site do not have to be the same. Inconsistency of reading frames may cause a frameshift downstream of the region to be deleted. The other nucleotide sequence is not particularly limited so long as a sequence that reduces or eliminates the activity of the encoded protein is chosen, and examples thereof include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The term "deletion of the amino acid sequence of a protein" refers to deletion of a partial or entire region of the amino acid sequence of the protein. In addition, the term "deletion of the amino acid sequence of a protein" means that the original amino acid sequence disappears in the protein, and also includes cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied similarly to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene include a gene of which a partial or entire region of the coding region is deleted, gene including a missense mutation, gene including a nonsense mutation, gene including a frame shift mutation, and gene inserted with an insertion sequence such as a transposon or marker gene. The structure of the recombinant DNA to be used for homologous recombination is not particularly limited as long as it causes homologous recombination in a desired manner. For example, a host can be transformed with a linear DNA containing the disruption-type gene and further containing upstream and downstream sequences of the wild-type gene on the chromosome at the respective ends, so that homologous recombination occurs at each of upstream and downstream sides of the wild-type gene, to thereby replace the wild-type gene with the disruption-type gene in one step. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from X. phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in an arbitrary combination.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA may be reduced to, for example, 50% or less, 20% or less, 10% or less, 5% or less, or 0% of that of a non-modified strain.

A reduction in the amount of a protein can be confirmed by performing SDS-PAGE and confirming the intensity of the separated protein band. A reduction in the amount of a protein can be confirmed by Western blotting using antibodies (Molecular Cloning, Cold Spring Harbor Laboratory Press, Cold Spring Harbor (USA) 2001). The amount of the protein (such as the number of molecules of the protein per cell) may be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

<1-5> Method for Increasing Expression of Gene

Hereinafter, methods for increasing the expression of a gene such as genes encoding the Tat secretion system will be explained.

The expression "the expression of a gene is increased" means that the expression of the gene is increased as compared with that of a non-modified strain. Specifically, the expression "the expression of a gene is increased" means that the expression amount of the gene per cell is increased as compared with that of a non-modified strain. The term "non-modified strain" used herein refers to a control strain that has not been modified so that the expression of an objective gene is increased. Examples of the non-modified strain include a wild-type strain and parent strain. Specific examples of the non-modified strain include the respective type strains of the species of bacteria. Specific examples of the non-modified strain also include strains exemplified above in relation to the description of coryneform bacteria. That is, in an embodiment, the expression of a gene may be increased as compared with a type strain, i.e. the type strain of the species to which the bacterium belongs. In another embodiment, the expression of a gene may also be increased as compared with *C. glutamicum* ATCC 13032. In another embodiment, the expression of a gene may also be increased as compared with *C. glutamicum* ATCC 13869. In another embodiment, the expression of a gene may also be increased as compared with *C. glutamicum* AJ12036 (FERM BP-734). In another embodiment, the expression of a gene may also be increased as compared with *C. glutamicum* YDK010. The expression "the expression of a gene is increased" may more specifically mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The degree of the increase in the expression of a gene is not particularly limited, so long as the expression of the gene is increased as compared with that of a non-modified strain. The expression of a gene may be increased to 1.5 times or more, 2 times or more, or 3 times or more, of that of a non-modified strain. Furthermore, the state that "the expression of a gene is increased" includes not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" also includes, for example, a state that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, or a transduction method using a phage. The structure of the recombinant DNA to be used for homologous recombination is not particularly limited as long as it causes homologous recombination in a desired manner. For example, a host can be transformed with a linear DNA containing an objective gene and further containing upstream and downstream sequences of the homologous recombination target region on the chromosome at the respective ends, so that homologous recombination occurs at each of upstream and downstream sides of the target region, to thereby replace the target region with the arbitrary sequence. The recombinant DNA to be used for homologous recombination may contain a marker gene for selection of transformants. Only one copy of, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). As the transposon, an artificial transposon may also be used (Japanese Patent Laid-open (Kokai) No. 9-70291).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in coryneform bacteria include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 (Japanese Patent Laid-open (Kokai) No. 3-210184); plasmids pCRY21, pCRY2KE, pCRY2KX, pCRY31, pCRY3KE, and pCRY3KX (Japanese Patent Laid-open (Kokai) No. 2-72876 and U.S. Pat. No. 5,185,262); plasmids pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pVK7 (Japanese Patent Laid-open (Kokai) No. 10-215883); pVK9 (US2006-0141588); pVC7 (Japanese Patent Laid-open (Kokai) No. 9-070291); pVS7 (WO2013/069634).

When a gene is introduced, it is sufficient that the gene is expressibly harbored by a host. Specifically, it is sufficient that the gene is harbored by the host so that it is expressed under control by a promoter that functions in the host. The promoter is not particularly limited so long as it functions in the host. The term "promoter that functions in a host" refers to a promoter that shows a promoter activity in the host. The promoter may be a promoter derived from the host, or a heterogenous promoter. The promoter may be the native promoter of the gene to be introduced, or a promoter of another gene. As the promoter, such a promoter as mentioned later which functions in a coryneform bacterium can be used.

A terminator for terminating the gene transcription can be provided downstream of the gene. The terminator is not particularly limited so long as it functions in the host. The terminator may be a terminator derived from the host, or may be a heterogenous terminator. The terminator may be the native terminator of the gene to be introduced, or may be a terminator of another gene.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by the bacterium as described herein. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced.

The gene to be introduced is not particularly limited so long as it codes for a protein that functions in a host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as the template. The gene to be introduced may also be totally synthesized, for example, on the basis of the nucleotide sequence of the gene (Gene, 60(1), 115-127 (1987)). The obtained gene can be used as it is, or after being modified as required. A gene can be modified by a known technique. For example, an objective mutation can be introduced into an objective site of DNA by the site-specific mutation method. That is, the coding region of a gene can be modified by the site-specific mutation method so that a specific site of the encoded protein include substitution, deletion, insertion, and/or addition of amino acid residue(s).

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene. Examples of the expression control sequence include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, homologous recombination. Examples of methods for modification using homologous recombination include a method of using a temperature sensitive vector, or the Red driven integration method (WO2005/010175).

The transcription efficiency of a gene can be improved by, for example, replacing the promoter of the gene on a chromosome with a stronger promoter. The "stronger promoter" means a promoter providing an improved transcription of a gene compared with an inherently existing wild-type promoter of the gene. Examples of stronger promoters usable in coryneform bacteria include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are strong promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherently existing wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of a gene can be improved by replacing a rare codon present in the gene with a synonymous codon more frequently used. That is, the gene to be introduced may be modified, for example, so as to contain optimal codons according to the frequencies of codons observed in a host to be used. Codons can be replaced by, for example, the site-specific mutation method. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Transformation of coryneform bacteria can be carried out by, specifically, for example, the protoplast method (Gene, 39, 281-286 (1985)), the electroporation method (Bio/Technology, 7, 1067-1070 (1989)), the electric pulse method (Japanese Patent Laid-open (Kokai) No. 2-207791), or the like.

An increase in the expression of a gene can be confirmed by, for example, confirming an increase in the activity of the protein expressed from the gene. An increase in the activity of a protein can be confirmed by measuring the activity of the protein. For example, an increase in the activity of the Tat secretion system can be confirmed by confirming an increase in the secretory production amount of a protein fused with a Tat-dependent signal peptide at the N-terminus. In such a case, it is preferred that the secretory production amount of the protein fused with a Tat-dependent signal peptide at the N-terminus is increased to 1.5 times or more, 2 times or more, or 3 times or more, of that of a non-modified strain.

An increase in the expression of a gene can also be confirmed by, for example, confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may be increased to, for example, 1.5 times or more, 2 times or more, or 3 times or more, of that of a non-modified strain.

An increase in the amount of a protein can be confirmed by performing SDS-PAGE and confirming the intensity of the separated protein band. An increase in the amount of a protein can be confirmed by Western blotting using antibodies (Molecular Cloning, Cold Spring Harbor Laboratory Press, Cold Spring Harbor (USA), 2001). The amount of the protein (such as the number of molecules of the protein per cell) may be increased to, for example, 1.5 times or more, 2 times or more, or 3 times or more, of that of a non-modified strain.

<1-6> Genetic construct for secretory expression of heterologous protein and introduction of the same It is known that a secretory protein is generally translated as a preprotein (also referred to as prepeptide) or a preproprotein (also referred to as prepropeptide), and then becomes a mature protein through processing. Specifically, a secretory protein is generally translated as a preprotein or preproprotein, then a signal peptide as the pre-moiety is cleaved with a protease (generally called signal peptidase), and the secretory protein is thereby converted into a mature protein or proprotein. As for the proprotein, the pro-moiety thereof is further cleaved by a protease, and the proprotein thereby becomes a mature protein. Therefore, a signal peptide is used for the secretory production of a heterologous protein in the method. a preprotein and a preproprotein of a secretory protein may be collectively referred to as "secretory protein precursor". the "signal peptide" (also referred to as "signal sequence") refers to an amino acid sequence present at the N-terminus of a secretory protein precursor, and not usually present in the natural mature protein.

The genetic construct can include, in the direction from 5' to 3', a promoter sequence that functions in a coryneform bacterium, a nucleic acid sequence encoding a signal peptide that functions in a coryneform bacterium, and a nucleic acid sequence encoding a heterologous protein. The nucleic acid sequence encoding the signal peptide may be ligated downstream from the promoter sequence so that the signal peptide is expressed under the control of the promoter. The nucleic acid sequence encoding the heterologous protein may be ligated downstream from the nucleic acid sequence encoding the signal peptide so that the heterologous protein is expressed as a fusion protein with the signal peptide. This fusion protein is also referred to as "fusion protein as described herein". In the fusion protein, the signal peptide and the heterologous protein may be or may not be adjacent to each other. That is, the expression "a heterologous protein is expressed as a fusion protein with a signal peptide" includes not only cases where a heterologous protein is expressed as a fusion protein with a signal peptide in which the signal peptide and the heterologous protein are adjacent to each other, but also include cases where a heterologous protein is expressed as a fusion protein in which the signal peptide and the heterologous protein are fused with each other via another amino acid sequence. For example, as described later, the fusion protein can contain an insertion sequence, such as an amino acid sequence comprising Gln-Glu-Thr and an amino acid sequence used for enzymatic digestion, between the signal peptide and the heterologous protein. As described later, it is acceptable that the eventually-obtained heterologous protein does not possess the signal peptide. That is, the expression "a heterologous protein is expressed as a fusion protein with a signal peptide" means that it is sufficient that the heterologous protein constitutes a fusion protein with a signal peptide at the time of expression, and it does not necessarily mean that the eventually-obtained heterologous protein constitutes a fusion protein with a signal peptide. A nucleic acid sequence may also be read as "gene". For example, a nucleic acid sequence encoding a heterologous protein is also referred to as "gene encoding a heterologous protein" or "heterologous protein gene". Examples of the nucleic acid sequence include DNA. The genetic construct may also include a control sequence (operator, SD sequence, terminator, etc.) effective for expression of the fusion protein in a coryneform bacterium at such an appropriate position that it can function.

The promoter is not particularly limited so long as a promoter that functions in a coryneform bacterium is chosen. The promoter may be a promoter derived from a coryneform bacterium, such as one derived from the host, or it may be a heterologous promoter. The promoter may be the native promoter of the heterologous protein, or a promoter of another gene. The "promoter that functions in a coryneform bacterium" refers to a promoter that possesses promoter activity in a coryneform bacterium.

Specific examples of the heterologous promoter include, for example, promoters derived from *E. coli* such as tac promoter, lac promoter, trp promoter, and araBAD promoter. Among these, strong promoters such as tac promoter and inducible promoters such as araBAD promoter are preferred.

Examples of the promoter derived from a coryneform bacterium include, for example, promoters of the genes of the cell surface layer proteins PS1, PS2 (also referred to as CspB), and SlpA (also referred to as CspA), and promoters of various amino acid biosynthesis system genes. Specific examples of the promoters of various amino acid biosynthesis system genes include, for example, promoters of the glutamate dehydrogenase gene of the glutamic acid biosynthesis system, the glutamine synthetase gene of the glutamine synthesis system, the aspartokinase gene of the lysine biosynthesis system, the homoserine dehydrogenase gene of the threonine biosynthesis system, the acetohydroxy acid synthetase gene of the isoleucine and valine biosynthesis system, 2-isopropylmalate synthetase gene of the leucine biosynthesis system, the glutamate kinase gene of the proline and arginine biosynthesis system, the phosphoribosyl-ATP pyrophosphorylase gene of the histidine biosynthesis system, the deoxyarabinoheptulonate phosphate (DAHP) synthetase gene of the aromatic amino acid biosynthesis systems such as those for tryptophan, tyrosine, and phenylalanine, the phosphoribosyl pyrophosphate (PRPP) amidotransferase gene of the nucleic acid biosynthesis systems such as those for inosinic acid and guanylic acid, the inosinic acid dehydrogenase gene, and the guanylic acid synthetase gene.

Examples of the promoter that functions in a coryneform bacterium include such strong promoters as described above usable in coryneform bacteria. As the promoter, a high activity type of an existing promoter may be obtained by using various reporter genes, and used. For example, by making the −35 and −10 regions in a promoter region closer to a consensus sequence, activity of the promoter can be enhanced (International Patent Publication WO00/18935). Examples of the method for evaluating strength of a promoter and strong promoters are described in the paper of Goldstein et al. (Prokaryotic promoters in biotechnology, Biotechnol. Annu. Rev., 1, 105-128 (1995)) and so forth. Furthermore, it is known that substitution, insertion, or deletion of several nucleotides in a spacer region between the ribosome-binding site (RBS) and the start codon, especially in a sequence immediately upstream of the start codon (5'-UTR), significantly affects stability and translation efficiency of mRNA, and these sequences can also be modified.

The signal peptide is not particularly limited so long as a signal peptide that functions in a coryneform bacterium is chosen. The signal peptide may be a signal peptide derived from or native to a coryneform bacterium, such as one derived from the host, or it may be a heterologous signal peptide. The signal peptide may be the native signal peptide of the heterologous protein, or a signal peptide of another gene. The "signal peptide that functions in a coryneform bacterium" refers to a peptide that when it is ligated to the N-terminus of an objective protein, allows the coryneform bacterium to secrete the protein. Whether a signal peptide functions in a coryneform bacterium can be confirmed by, for example, expressing an objective protein in a form of being fused with the signal peptide, and confirming whether the protein is secreted.

Examples of the signal peptide include Tat-dependent signal peptides and Sec-dependent signal peptides.

The term "Tat-dependent signal peptide" refers to a signal peptide recognized by the Tat system. The term "Tat-dependent signal peptide" may specifically refer to a signal peptide that, upon being linked at the N-terminus of an objective protein, results in secretion of the protein by the Tat secretion system.

Examples of the Tat-dependent signal peptide include the signal peptide of the TorA protein (trimethylamine-N-oxidoreductase) of *E. coli*, the signal peptide of SufI protein (suppressor of ftsI) of *E. coli*, the PhoD protein (phosphodiesterase) of *Bacillus subtilis*, the signal peptide of LipA protein (lipoic acid synthase) of *Bacillus subtilis*, and the signal peptide of IMD protein (isomaltodextranase) of *Arthrobacter globiformis*. The amino acid sequences of these signal peptides are as follows.

```
TorA signal peptide:
                                         (SEQ ID NO: 41)
MNNNDLFQASRRRFLAQLGGLTVAGMLGPSLLTPRRATA SufI signal peptide:
                                         (SEQ ID NO: 42)
MSLSRRQFIQASGIALCAGAVPLKASA PhoD signal peptide:
                                         (SEQ ID NO: 43)
MAYDSRFDEWVQKLKEESFQNNTFDRRKFIQGAGKIAGLSLGLTIAQS LipA signal peptide:
                                         (SEQ ID NO: 44)
MKFVKRRTTALVTTLMLSVTSLFALQPSAKAAEH IMD signal peptide:
                                         (SEQ ID NO: 45)
MMNLSRRTLLTTGSAATLAYALGMAGSAQA
```

The Tat-dependent signal peptide has a twin-arginine motif. Examples of the twin-arginine motif include S/T-R-R-X-F-L-K (SEQ ID NO: 46) and R-R-X-#-# (#: hydrophobic residue) (SEQ ID NO: 47).

The term "Sec-dependent signal peptide" refers to a signal peptide recognized by the Sec system. The term "Sec-dependent signal peptide" may specifically refer to a signal peptide that, upon being linked at the N-terminus of an objective protein, results in secretion of the protein by the Sec secretion system.

Examples of the Sec-dependent signal peptide include a signal peptide of a cell surface layer protein of a coryneform bacterium. The cell surface layer protein of coryneform bacteria is as described above. Examples of the cell surface layer protein of coryneform bacteria include PS1 and PS2 (CspB) derived from *C. glutamicum* (Japanese Patent Laid-open (Kohyo) No. 6-502548), and SlpA (CspA) derived from *C. ammoniagenes* (*C. stationis*) (Japanese Patent Laid-open (Kokai) No. 10-108675). The amino acid sequence of the signal peptide of PS1 (PS1 signal peptide) of *C. glutamicum* is shown in SEQ ID NO: 48, the amino acid sequence of the signal peptide of PS2 (CspB) (PS2 signal peptide) of *C. glutamicum* is shown in SEQ ID NO: 49, and the amino acid sequence of the signal peptide of SlpA (CspA) (S1pA signal peptide) of *C. stationis* is shown in SEQ ID NO: 50.

The Tat-dependent signal peptide may be a variant of any of the Tat-dependent signal peptides exemplified above, so long as it contains a twin-arginine motif and the original function thereof is maintained. The Sec-dependent signal peptide may be a variant of any of the Sec-dependent signal peptides exemplified above, so long as the original function thereof is maintained. The above descriptions concerning conservative variants of the HrrSA proteins and the hrrSA genes can be applied similarly to variants of the signal peptide and the gene encoding it. For example, the signal peptide may be a peptide having any of the aforementioned amino acid sequences, but including substitution, deletion, insertion, and/or addition of one or several amino acid residues at one or several positions. The number meant by the term "one or several" used for a variant of the signal peptide is specifically, 1 to 7, 1 to 5, 1 to 3, or 1 to 2. The terms "TorA signal peptide", "SufI signal peptide", "PhoD signal peptide", "LipA signal peptide", "IMD signal peptide", "PS1 signal peptide", "PS2 signal peptide", and "SlpA signal peptide" include not only the peptides of SEQ ID NOS: 41-50, respectively, but also includes conservative variants thereof.

The expression "original function is maintained" used for the Tat-dependent signal peptide means that the peptide is recognized by the Tat system, and specifically, may mean that the peptide has a function of, upon being linked at the N-terminus of an objective protein, resulting in secretion of the protein by the Tat secretion system. Whether a peptide function as the Tat-dependent signal peptide can be confirmed by, for example, confirming an increase in the secretory production amount of a protein linked with the peptide at the N-terminus due to enhancement of the Tat secretion system, or confirming a reduction in the secretory production amount of a protein linked with the peptide at the N-terminus due to deletion of the Tat secretion system.

The expression "original function is maintained" used for the Sec-dependent signal peptide means that the peptide is recognized by the Sec system, and specifically, may mean that the peptide has a function of, upon being linked at the N-terminus of an objective protein, resulting in secretion of the protein by the Sec secretion system. Whether a peptide function as the Sec-dependent signal peptide can be confirmed by, for example, confirming an increase in the secretory production amount of a protein linked with the peptide at the N-terminus due to enhancement of the Sec secretion system, or confirming a reduction in the secretory production amount of a protein linked with the peptide at the N-terminus due to deletion of the Sec secretion system.

The signal peptide is generally cleaved by a signal peptidase, when the translation product is secreted out of the cell. That is, it is acceptable that the eventually-obtained heterologous protein does not possess the signal peptide. As a gene encoding a signal peptide, although a naturally occurring gene may be used as it is, it may be modified so that it has the optimal codons according to codon frequencies in a host to be used.

In the genetic construct, a nucleic acid sequence encoding an amino acid sequence comprising Gln-Glu-Thr may be inserted between the nucleic acid sequence encoding the signal peptide and the nucleic acid sequence encoding the heterologous protein (WO2013/062029). The "amino acid sequence comprising Gln-Glu-Thr" is also referred to as "insertion sequence". Examples of the insertion sequence include amino acid sequences comprising Gln-Glu-Thr described in WO2013/062029. Particularly, the insertion sequence can be used in combination with the Sec-dependent signal peptide.

The insertion sequence can be a sequence consisting of 3 or more amino acid residues from the N-terminus of the mature protein of the cell surface layer protein CspB of a coryneform bacterium (henceforth also referred to as "mature CspB" or "CspB mature protein"). The term "sequence consisting of 3 or more amino acid residues from the N-terminus" refers to an amino acid sequence starting from the amino acid residue at position 1 of the N-terminus to an amino acid residue at position 3 or a more remote position.

The cell surface layer protein CspB of coryneform bacteria is as described above. Specific examples of CspB include, for example, CspB of *C. glutamicum* ATCC 13869, CspB of 28 strains of *C. glutamicum* exemplified above, and variants thereof. In the amino acid sequence of the CspB protein of *C. glutamicum* ATCC 13869 shown in SEQ ID NO: 34, the amino acid residues at positions 1 to 30 correspond to the signal peptide, and the amino acid residues at positions 31 to 499 correspond to the CspB mature protein. The amino acid sequence of the CspB mature protein of *C. glutamicum* ATCC 13869 except for the 30 amino acid residues as the signal peptide moiety is shown in SEQ ID NO: 51. In the mature CspB of *C. glutamicum* ATCC 13869, the amino acid residues at positions 1 to 3 of the N-terminus correspond to Gln-Glu-Thr.

The insertion sequence can be an amino acid sequence starting from the amino acid residue at position 1 to an amino acid residue at any of the positions 3 to 50 of the mature CspB. The insertion sequence can be an amino acid sequence starting from the amino acid residue at position 1 to an amino acid residue at any of the positions 3 to 8, 17, and 50 of the mature CspB. The insertion sequence can be an amino acid sequence starting from the amino acid residue at position 1 to an amino acid residue at any of the positions 4, 6, 17 and 50.

The insertion sequence can be an amino acid sequence such as the following:

```
(A)  Gln-Glu-Thr
                                       (SEQ ID NO: 52)
(B)  Gln-Glu-Thr-Xaa1
                                       (SEQ ID NO: 53)
(C)  Gln-Glu-Thr-Xaa1-Xaa2
                                       (SEQ ID NO: 54)
(D)  Gln-Glu-Thr-Xaa1-Xaa2-Xaa3
```

(E) an amino acid sequence consisting of Gln-Glu-Thr fused with the amino acid residues at positions 4 to 7 of a mature CspB, (F) an amino acid sequence consisting of Gln-Glu-Thr fused with the amino acid residues at positions 4 to 8 of a mature CspB, (G) an amino acid sequence consisting of Gln-Glu-Thr fused with the amino acid residues at positions 4 to 17 of a mature CspB, (H) an amino acid sequence consisting of Gln-Glu-Thr fused with the amino acid residues at positions 4 to 50 of a mature CspB.

In the amino acid sequences (A) to (H), Xaa1 is Asn, Gly, Thr, Pro, or Ala, Xaa2 is Pro, Thr, or Val, and Xaa3 is Thr or Tyr. As for the amino acid sequences (A) to (H), "Gln-Glu-Thr fused with the amino acid residues at positions 4 to X of a mature CspB" means that the amino acid residues at positions 4 to X of the N-terminus of a mature CspB is fused to Thr of Gln-Glu-Thr. The first to third amino acid residues of the N-terminus of a mature CspB are usually Gln-Glu-Thr, and in such a case, "an amino acid sequence consisting of Gln-Glu-Thr fused with the amino acid residues at positions 4 to X of a mature CspB" is synonymous with an amino acid sequence consisting of the amino acid residues at position 1 to X of the mature CspB.

Furthermore, specifically, the insertion sequence can be an amino acid sequence selected from the group consisting of Gln-Glu-Thr-Asn-Pro-Thr (SEQ ID NO: 55), Gln-Glu-Thr-Gly-Thr-Tyr (SEQ ID NO: 56), Gln-Glu-Thr-Thr-Val-Thr (SEQ ID NO: 57), Gln-Glu-Thr-Pro-Val-Thr (SEQ ID NO: 58), and Gln-Glu-Thr-Ala-Val-Thr (SEQ ID NO: 59).

The "amino acid residue at position X of the mature CspB" refers to an amino acid residue corresponding to the amino acid residue at position X in SEQ ID NO: 51. Which amino acid residue is the "amino acid residue corresponding to the amino acid residue at position X in SEQ ID NO: 51" in the amino acid sequence of an arbitrary mature CspB can be determined by alignment between the amino acid sequence of the arbitrary mature CspB and the amino acid sequence of SEQ ID NO: 51.

Examples of the heterologous protein to be produced by secretory production according to the method include, for example, physiologically active proteins, receptor proteins, antigenic proteins to be used as vaccines, enzymes, and any other proteins.

Examples of the enzymes include, for example, transglutaminase, protein glutaminase, isomaltodextranase, protease, endopeptidase, exopeptidase, aminopeptidase, carboxypeptidase, collagenase, chitinase, and so forth. Examples of transglutaminase include, for example, secretory-type transglutaminases of Actinomycetes such as *Streptoverticillium mobaraense* IFO 13819 (WO01/23591), *Streptoverticillium cinnamoneum* IFO 12852, *Streptoverticillium griseocarneum* IFO 12776, and *Streptomyces lydicus* (WO96/06931), and of filamentous fungi such as Oomycetes (WO96/22366). Examples of protein glutaminase include, for example, protein glutaminase of *Chryseobacterium proteolyticum* (WO2005/103278). Examples of isomaltodextranase include, for example, isomaltodextranase of *Arthrobacter globiformis* (WO2005/103278).

Examples of the physiologically active proteins include, for example, growth factors, hormones, cytokines, and antibody-related molecules.

Specific examples of the growth factors include, for example, epidermal growth factor (EGF), insulin-like growth factor-1 (IGF-1), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), and hepatocyte growth factor (HGF).

Specific examples of the hormones include, for example, insulin, glucagon, somatostatin, human growth hormone (hGH), parathyroid hormone (PTH), calcitonin, and exenatide.

Specific examples of the cytokines include, for example, interleukins, interferons, and tumor necrosis factors (TNFs).

The growth factors, hormones, and cytokines may not be strictly distinguished from one another. For example, a physiologically active protein may be a protein belonging to a single group selected from growth factors, hormones, and cytokines, or may be a protein belonging to a plurality of groups selected from those.

Furthermore, a physiologically active protein may be an intact protein, or may be a part of a protein. Examples of a part of a protein include, for example, a part having physiological activity. Specific examples of a part having physiological activity include, for example, Teriparatide, a physiologically active peptide consisting of the N-terminal 34 amino acid residues of parathyroid hormone (PTH).

The term "antibody-related molecule" refers to a protein containing a molecular species consisting of a single domain or a combination of two or more domains selected from the domains constituting a complete antibody. Examples of the domains constituting a complete antibody include heavy chain domains VH, CH1, CH2, and CH3, and light chain domains VL and CL. The antibody-related molecule may be a monomeric protein, or may be a multimeric protein, so long as it contains the above-mentioned molecular species. When the antibody-related molecule is a multimeric protein, it may be a homo-multimer consisting of a single kind of subunit, or may be a hetero-multimer consisting of two or more kinds of subunits. Specific examples of the antibody-related molecules include, for example, complete antibody, Fab, F(ab'), F(ab')2, Fc, dimer consisting of a heavy chain (H chain) and a light chain (L chain), Fc-fusion protein, heavy chain (H chain), light chain (L chain), light chain Fv (scFv), sc(Fv)$_2$, disulfide-bonded Fv (sdFv), diabody, and VHH fragment (Nanobody (registered trademark)). More specific examples of the antibody-related molecules include, for example, Trastuzumab.

The receptor proteins are not particularly limited. A receptor protein may be, for example, a receptor protein for any of physiologically active proteins and other physiologically active substances. Examples of the other physiologically active substances include, for example, neurotransmitters such as dopamine. Furthermore, a receptor protein may be an orphan receptor of which the corresponding ligand is not known.

The antigen proteins to be used as vaccines are not particularly limited, so long as they are proteins that can induce an immune response. An antigen protein can be appropriately selected depending on the intended object of the immune response.

In addition, examples of other proteins include Liver-type fatty acid-binding protein (LFABP), fluorescent protein, immunoglobulin-binding protein, albumin, and extracellular protein. Examples of the fluorescent protein include Green Fluorescent Protein (GFP). Examples of the immunoglobulin-binding protein include Protein A, Protein G, and Protein L. Examples of albumin include human serum albumin.

Examples of the extracellular protein include fibronectin, vitronectin, collagen, osteopontin, laminin, and partial sequences thereof. Laminin is a protein having a heterotrimeric structure consisting of an α chain, a β chain, and a γ chain. Examples of laminin include laminin of mammals. Examples of the mammals include primates such as human, monkey, and chimpanzee; rodents such as mouse, rat, hamster, and guinea pig; and other various mammals such as rabbit, horse, cattle, sheep, goat, pig, dog, and cat. Particular examples of the mammals include human. Examples of the subunit chains of laminin (i.e. α, (β, and γ chains) include 5 kinds of α chains (α1 to α5), 3 kinds of β chains (β1 to β3), and 3 kinds of γ chains (γ1 to γ3). Laminin constitutes various isoforms depending on combinations of these subunits. Specific examples of laminin include, for example, laminin 111, laminin 121, laminin 211, laminin 213, laminin 221, laminin 311, laminin 321, laminin 332, laminin 411, laminin 421, laminin 423, laminin 511, laminin 521, and laminin 523. Examples of the partial sequence of laminin include laminin E8, which is an E8 fragment of laminin. Laminin E8 is a protein having a heterotrimeric structure consisting of an E8 fragment of a chain (α chain E8), an E8 fragment of β chain (β chain E8), and an E8 fragment of γ chain (γ chain E8). The subunit chains of laminin E8 (i.e. α chain E8, (β chain E8, and γ chain E8) are also collectively referred to as "E8 subunit chains". Examples of the E8 subunit chains includes E8 fragments of the laminin subunit chains exemplified above. Laminin E8 constitutes various isoforms depending on combinations of these E8 subunit chains. Specific examples of laminin E8 include, for example, laminin 111E8, laminin 121E8, laminin 211E8, laminin 221E8, laminin 332E8, laminin 421E8, laminin 411E8, laminin 511E8, and laminin 521E8.

A gene encoding the heterologous protein such as these proteins can be used as it is, or after being modified as required. A gene encoding the heterologous protein can be modified, for example, depending on a host to be used and/or for obtaining a desired activity. For example, a gene encoding the heterologous protein may be modified so that the amino acid sequence of the encoded heterologous protein include substitution, deletion, insertion, and/or addition of one or several amino acid residues. The above descriptions concerning variants of the HrrSA proteins and the hrrSA genes can be applied similarly to the heterologous protein to be produced by secretory production by the method as described herein and the gene encoding it. A protein specified with the type of organism from which the protein is derived is not limited to proteins per se found in that organism, and shall also include proteins having any of the amino acid sequences of proteins found in that organism and variants thereof. That is, for example, the term "protein derived from human" is not limited to proteins per se found in human, and shall also include proteins having any of the amino acid sequences of proteins found in human and variants thereof. Furthermore, in the gene encoding the heterologous protein, any codon(s) may be replaced with respective equivalent codon(s) thereof. For example, the gene encoding the heterologous protein may be modified so that it has optimal codons according to codon frequencies in the host to be used.

The genetic construct may further include a nucleic acid sequence encoding an amino acid sequence used for enzymatic digestion between the nucleic acid sequence encoding the amino acid sequence comprising Gln-Glu-Thr and the nucleic acid sequence encoding the heterologous protein. If the amino acid sequence used for enzymatic digestion is inserted in the fusion protein, the expressed fusion protein can be enzymatically digested to obtain the objective heterologous protein.

The amino acid sequence used for enzymatic digestion is not particularly limited so long as it is a sequence that can be recognized and digested by an enzyme that hydrolyzes a peptide bond, and a usable sequence can be appropriately chosen according to the amino acid sequence of the objective heterologous protein. The nucleic acid sequence encoding the amino acid sequence used for enzymatic digestion can be appropriately designed on the basis of that amino acid sequence. For example, the nucleic acid sequence encoding the amino acid sequence used for enzymatic digestion can be designed so that it has optimal codons according to codon frequencies observed in the host.

The amino acid sequence used for enzymatic digestion can be a recognition sequence of a protease showing high substrate specificity. Specific examples of such an amino acid sequence include, for example, a recognition sequence of factor Xa protease and a recognition sequence of proTEV protease. The factor Xa protease and the proTEV protease recognize the amino acid sequence of Ile-Glu-Gly-Arg (=IEGR, SEQ ID NO: 60) and the amino acid sequence of Glu-Asn-Leu-Tyr-Phe-Gln (=ENLYFQ, SEQ ID NO: 61) in a protein, respectively, to specifically digest the protein at the C-terminal side of each recognition sequence.

The N-terminal region of the heterologous protein eventually obtained by the method may be the same as that of the natural protein, or may not be the same as that of the natural protein. For example, the N-terminal region of the eventually obtained heterologous protein may be that of the natural protein including addition or deletion of one or several amino acid residues. Although the number of the "one or several" amino acid residues may differ depending on the full length or structure of the objective heterologous protein, specifically, it is 1 to 20, 1 to 10, 1 to 5, or 1 to 3.

Furthermore, the heterologous protein to be produced by secretory production may be a protein including a pro-structure moiety (proprotein). When the heterologous protein to be produced by secretory production is a proprotein, the heterologous protein to be eventually obtained may be the proprotein or may not be the proprotein. That is, the proprotein may be processed into the mature protein by cleavage of the pro-structure moiety. The cleavage can be attained with, for example, a protease. When a protease is used, generally, the proprotein can be cleaved at a position substantially the same as that of the natural protein, or at exactly the same position as that of the natural protein so that the same mature protein as the natural mature protein is obtained, in view of the activity of the eventually obtained protein. Therefore, generally, a specific protease that cleaves the proprotein at such a position that the same protein as the naturally occurring mature protein is generated is a particular example. However, the N-terminal region of the heterologous protein to be eventually obtained may not be the same as that of the natural protein as described above. For example, depending on type, purpose of use etc. of the heterologous protein to be produced, a protein having an N-terminus longer or shorter by one to several amino acid residues compared with the natural protein may have more appropriate activity. Proteases include, for example, commercially available proteases such as Dispase (produced by Boehringer Mannheim) as well as those obtainable from culture broth of a microorganism such as culture broth of actinomycetes. Such proteases may be used in an un-purified state, or may be used after purification to an appropriate purity as required. When the pro-structure moiety is cleaved to obtain a mature protein, the inserted amino acid sequence comprising Gln-Glu-Thr is removed together with the pro-structure moiety, and therefore the objective protein can be obtained without providing an amino acid sequence used for enzymatic digestion downstream from the amino acid sequence comprising Gln-Glu-Thr.

The method for introducing the genetic construct into the coryneform bacterium is not particularly limited. The term "introduction of the genetic construct" refers to making a host harbor the genetic construct. The term "introduction of the genetic construct" includes not only cases where the genetic construct that has been preliminarily constructed is collectively introduced into a host, but also includes cases where at least the heterologous protein gene is introduced into a host and the genetic construct is constructed in the host. In the bacterium, the genetic construct may be present on a vector that autonomously replicates out of the chromosome such as a plasmid, or may be incorporated into the chromosome. The genetic construct can be introduced, for example, in the same manner as that for introduction of a gene in methods for increasing the expression of a gene described above. In addition, for constructing the bacterium, introduction of the genetic structure, reduction in the activity of HrrSA system, and other modifications can be performed in any order.

The genetic construct can be introduced into a host by using, for example, a vector comprising the genetic construct. For example, the genetic construct can be introduced into a host by ligating the genetic construct with a vector to construct an expression vector of the genetic construct, and transforming the host with the expression vector. Also, when the vector contains a promoter that functions in a coryneform bacterium, an expression vector of the genetic construct can be constructed by ligating the nucleic acid sequence encoding the fusion protein downstream from the promoter. The vector is not particularly limited so long as a vector autonomously replicable in a coryneform bacterium is chosen. The vector usable in a coryneform bacterium is as described above.

Furthermore, the genetic construct can be introduced into the chromosome of a host by using, for example, a transposon such as an artificial transposon. When a transposon is used, the genetic construct is introduced into the chromosome by homologous recombination or translocation ability of the transposon itself. Furthermore, the genetic construct can also be introduced into the chromosome of a host by other introduction methods utilizing homologous recombination. Examples of the introduction methods utilizing homologous recombination include, for example, methods utilizing a linear DNA, a plasmid having a temperature sensitive replication origin, a plasmid capable of conjugative transfer, a suicide vector not having a replication origin that functions in a host, and so forth. In addition, at least the heterologous protein gene may be introduced into the chromosome so that the genetic construct is constituted on the chromosome. In this case, a part or all of the constituents contained in the genetic construct, other than the heterologous protein gene, may be inherently present on the chromosome of the host. Specifically, for example, by using a promoter sequence inherently present on the chromosome of the host and a nucleic acid sequence encoding a signal peptide inherently present on the chromosome of the host and ligated downstream from the promoter sequence as they are, and replacing only the gene ligated downstream from the nucleic acid sequence encoding the signal peptide with an objective heterologous protein gene, the genetic construct can be constituted on the chromosome, and the bacterium can be thereby constructed. A part of the genetic construct, such as the heterologous protein gene, can be introduced into the chromosome in the same manner as that for introduction of the genetic construct into the chromosome.

The genetic construct or a constituent thereof, such as promoter sequence, nucleic acid sequence encoding a signal peptide, or nucleic acid sequence encoding a heterologous protein, can be obtained by, for example, cloning. Specifically, for example, the genetic construct can be obtained by obtaining an objective heterologous protein gene by cloning from an organism having the objective heterologous protein, and then subjecting the gene to modification such as introduction of the nucleic acid sequence encoding the signal peptide and introduction of the promoter sequence. Furthermore, the genetic construct or a constituent thereof can also be obtained by chemical synthesis (Gene, 60(1), 115-127 (1987)). The obtained genetic construct or constituent thereof can be used as it is, or after being modified as required.

Furthermore, when two or more kinds of proteins are expressed, it is sufficient that the genetic constructs for secretory expression of the proteins are harbored by the bacterium so that secretory expression of the objective heterologous proteins can be attained. Specifically, for example, all the genetic constructs for secretory expression of the proteins may be harbored on a single expression vector, or harbored on the chromosome. Alternatively, the genetic constructs for secretory expression of the proteins may be separately harbored on a plurality of expression vectors, or may be separately harbored on one or more expression vectors and the chromosome. The "case where two or more kinds of proteins are expressed" refers to, for example, a case where two or more kinds of heterologous proteins are produced by secretory production, or a case where a hetero-multimeric protein is produced by secretory production.

The method for introducing the genetic construct into the coryneform bacterium is not particularly limited, and a generally used method, for example, the protoplast method (Gene, 39, 281-286 (1985)), the electroporation method (Bio/Technology, 7, 1067-1070 (1989)), the electric pulse method (Japanese Patent Laid-open (Kokai) No. 2-207791), and so forth can be used.

<2> Method for Producing Heterologous Protein

By culturing the bacterium obtained as described above to express a heterologous protein, a large amount of the heterologous protein secreted out of the cells is obtained.

The bacterium can be cultured according to a usually used method and conditions. For example, the bacterium can be cultured in a usual medium containing a carbon source, a nitrogen source, and inorganic ions. In order to obtain still higher proliferation, organic micronutrients such as vitamins and amino acids can also be added as required.

As the carbon source, carbohydrates such as glucose and sucrose, organic acids such as acetic acid, alcohols, and others can be used. As the nitrogen source, ammonia gas, aqueous ammonia, ammonium salts, and others can be used. As the inorganic ions, calcium ions, magnesium ions, phosphate ions, potassium ions, iron ions, and so forth are appropriately used as required. The culture is performed within appropriate ranges of pH 5.0 to 8.5 and 15 to 37° C. under aerobic conditions for 1 to 7 days. Furthermore, the culture conditions for L-amino acid production by coryneform bacteria and other conditions described for the methods for producing a protein using a Sec- or Tat-dependent signal peptide can be used (refer to WO01/23591 and WO2005/103278). Furthermore, when an inducible promoter is used for expression of the heterologous protein, culture may also be performed with adding a promoter-inducing agent to the medium. By culturing the bacterium under such conditions, a large amount of the objective protein is produced in cells and efficiently secreted out of the cells. In addition, according to the method, the produced heterologous protein is secreted out of the cells, and therefore a protein that is generally lethal if it is accumulated in a large amount in cells of microorganisms, such as transglutaminases, can also be continuously produced without lethal effect.

The protein secreted in the medium according to the method can be separated and purified from the medium after the culture by a method well known to those skilled in the art. For example, after the cells are removed by centrifugation or the like, the protein can be separated and purified by a known appropriate method such as salting out, ethanol precipitation, ultrafiltration, gel filtration chromatography, ion exchange column chromatography, affinity chromatography, medium or high pressure liquid chromatography, reverse phase chromatography, and hydrophobic chromatography, or a combination of these. Furthermore, in a certain case, culture or culture supernatant may be used as it is. The protein secreted in the cell surface layer according to the method can also be separated and purified in the same manner as that for the case where the protein is secreted in the medium, after solubilizing it by a method well known to those skilled in the art such as elevation of salt concentration and use of a surfactant. Furthermore, in a certain case, the protein secreted in the cell surface layer may be used as, for example, an immobilized enzyme, without solubilizing it.

Secretory production of the objective heterologous protein can be confirmed by performing SDS-PAGE for the culture supernatant and/or a fraction containing the cell surface layer as a sample, and confirming the molecular weight of the separated protein band. Furthermore, secretory production of the objective heterologous protein can also be confirmed by performing Western blotting using antibodies for the culture supernatant and/or a fraction containing the cell surface layer as a sample (Molecular Cloning, Cold spring Harbor Laboratory Press, Cold Spring Harbor (USA), 2001). Furthermore, secretory production of the objective heterologous protein can also be confirmed by detecting an N-terminal amino acid sequence of the objective protein using a protein sequencer. Furthermore, secretory production of the objective heterologous protein can also be confirmed by determining the mass of the objective protein using a mass spectrometer. Furthermore, when the objective heterologous protein is an enzyme or a protein having a certain measurable physiological activity, secretory production of the objective heterologous protein can be confirmed by measuring enzymatic activity or the physiological activity of the objective protein in the culture supernatant and/or a fraction containing the cell surface layer as a sample.

EXAMPLES

The presently described subject matter will be further specifically explained with reference to the following examples. However, these examples should not be construed to limit the scope of the presently described subject matter.

Reference Example 1

Obtaining PhoS-Mutant Strains Derived from *C. glutamicum* YDK010 Strain (1) Obtaining natural mutant strain having mutation in phoS gene The *C. glutamicum* YDK010 strain disclosed in WO2002/081694 was transformed with pPKK50TEV-Teri disclosed in WO2014/126260, which is a secretory expression plasmid of a physiologically active peptide Teriparatide. Incidentally, pPKK50TEV-Teri is a secretory expression vector of a physiologically active peptide Teriparatide, and a plasmid having a promoter region of cspB gene of the *C. glutamicum* ATCC 13869 strain and a nucleotide sequence expressively linked downstream from the promoter and encoding a fusion protein (hereinafter, referred to as CspB50TEV-Teri) of the CspB signal peptide of the same strain, the N-terminal 50 amino acid residues of mature CspB of the same strain, the ProTEV protease recognition sequence ENLYFQ (SEQ ID NO.: 61), and Teriparatide (WO2014/126260). The *C. glutamicum* YDK010 strain is a cell-surface-layer-protein-CspB-deficient strain of the *C. glutamicum* AJ12036 strain (FERM BP-734) (WO2002/081694). The obtained transformant was cultured on CM-Dex agar medium (5 g of glucose, 0.4 g of $MgSO_4 \cdot 7H_2O$, 0.01 g of $FeSO_4 \cdot 7H_2O$, 0.01 g of $MnSO_4 \cdot 5H_2O$, 1 g of $KH_2PO_4$, 10 µg of biotin, 10 g of Difco™ Select Soytone (Becton Dickinson), 10 g of Bacto™ Yeast Extract (Becton Dickinson), 3 g of urea, 1.2 g (as total nitrogen) of soybean hydrolysate solution obtained with HCl, and 20 g of agar powder, filled up with water to 1 L, and adjusted to pH6.5) containing 25 mg/L of kanamycin at 30° C., to form colonies.

After the culture, a natural mutant strain of which the phoS gene was introduced with a mutation was selected, and designated as strain YDK0107. The nucleotide sequence of the mutant phoS gene of the YDK0107 strain and the amino acid sequence of the mutant PhoS protein of the YDK0107 strain are shown in SEQ ID NOS: 1 and 2, respectively. In the mutant phoS gene of the YDK0107 strain, "G" at position 906 of SEQ ID NO: 3 of the wild-type phoS gene of the YDK010 strain has been mutated to "T". Due to this mutation, in the mutant PhoS protein of the YDK0107 strain, the tryptophan residue at position 302 of SEQ ID NO: 4 of the wild-type PhoS protein of the YDK010 strain has been mutated to a cysteine residue. This mutation was designated as PhoS(W302C) mutation. Incidentally, genomic DNA was prepared with PurElute™ Genomic DNA Kit (EdgeBio), and nucleotide sequencing was carried out with BigDye(R) Terminator v3.1 Cycle Sequencing Kit (Applied Biosystems) and 3130 Genetic Analyzer (Applied Biosystems).

(2) Construction of phoS-gene-substitution vector encoding mutant PhoS(W302C)

PCR was carried out by using primers of SEQ ID NOS: 5 and 6, and genomic DNA of the *C. glutamicum* YDK0107 strain prepared with PurElute™ Genomic DNA Kit (EdgeBio) as the template, to amplify a region of about 1.5 kbp containing a phoS gene encoding the mutant PhoS (W302C) (also referred to as mutant phoS gene or mutant phoS(W302C) gene). PCR was carried out with Pyrobest(R) DNA polymerase (Takara Bio), and the reaction conditions were according to the protocol recommended by the manufacturer.

Then, the amplified DNA fragment of about 1.5 kbp was subject to agarose gel electrophoresis, an objective band was excised, and the DNA fragment was collected from the gel with Wizard(R) SV Gel and PCR Clean-Up System (Promega). The collected DNA fragment was inserted at SmaI site of pBS5T disclosed in WO2006/057450, and the resultant was introduced into competent cells of *E. coli* JM109 (Takara Bio). A Strain harboring a plasmid into which the DNA fragment containing the mutant phoS gene was cloned was obtained, the plasmid was collected from the strain, to obtain pBS5T-phoS(W302C), a plasmid into which the mutant phoS gene was cloned. As a result of nucleotide sequencing of the inserted fragment, it was confirmed that the expected gene was cloned. Nucleotide sequencing was carried out with BigDye(R) Terminator v3.1 Cycle Sequencing Kit (Applied Biosystems) and 3130 Genetic Analyzer (Applied Biosystems).

(3) Construction of PhoS(W302C)-Mutant Strain

The *C. glutamicum* YDK010 strain disclosed in WO2002/081694 was transformed with the plasmid pBS5T-phoS (W302C) constructed in Reference example 1 (2). Strain selection from the obtained transformants was carried out according to the method disclosed in WO2006/057450, to obtain YDK010::phoS(W302C), which is a strain of which the wild-type phoS gene on the chromosome was replaced with the mutant phoS gene. Incidentally, even without using the genome DNA of the YDK0107 strain, the YDK010:: phoS(W302C) strain can be reproducibly constructed by using, for example, the mutant phoS gene obtained by genetic engineering.

Example 1

Construction of *Corynebacterium glutamicum* Deficient In Two-Component Regulatory System Response Regulator Gene hrrA (1) Construction of hrrA-Gene-Deletion Vector pBS5TΔhrrA The genome sequence of the *C. glutamicum* ATCC 13869 strain and the nucleotide sequence of the hrrA gene encoding the response regulator HrrA of the two-component regulatory system HrrSA have already been determined (GenBank Accession No. AP017557, NCBI locus tag CGBL 0128750).

PCR was carried out by using genomic DNA of the *C. glutamicum* ATCC 13869 strain prepared with PurElute' Genomic DNA Kit (EdgeBio) as the template, in combination with primers of SEQ ID NOS: 7 and 8, to amplify a 5'-side upstream region of the hrrA gene of about 1 kbp, and in combination with primers of SEQ ID NOS: 9 and 10 to amplify a 3'-side downstream region of the hrrA gene of about 1 kbp. PCR was carried out with Pyrobest(R) DNA polymerase (Takara Bio), and the reaction conditions were according to the protocol recommended by the manufacturer. Each amplified DNA fragment of about 1 kbp was subject to agarose gel electrophoresis, an objective band was excised, and the DNA fragment was collected from the gel with Wizard(R) SV Gel and PCR Clean-Up System (Promega). The collected 2 DNA fragments were inserted at SmaI site of pBS5T disclosed in WO2006/057450 by infusion reaction, to obtain a hrrA-gene-deletion vector pBS5TΔhrrA. The infusion reaction was carried out with In-Fusion(R) HD Cloning Kit (Takara Bio), and the reaction conditions were according to the protocol recommended by the manufacturer.

(2) Construction of hrrA-Gene-Deletion Strains of YDK010 Strain and YDK010::phoS(W302C) Strain The *C. glutamicum* YDK010 strain disclosed in WO2002/081694 and the YDK010::phoS(W302C) strain constructed in Reference example 1(3) were each transformed with the plasmid pBS5TΔhrrA constructed in Example 1(1). Strain selection from the obtained transformants was carried out according to the method disclosed in WO2006/057450, to obtain strains YDK010ΔhrrA and YDK010::phoS(W302C) ΔhrrA, which are deficient in the hrrA gene.

Example 2

Secretory Production of Protein L Using *Corynebacterium glutamicum* Deficient in Two-Component Regulatory System Response Regulator Gene hrrA (1) Construction of Secretory Expression Plasmid of Protein L The amino acid sequence of Protein L, which is an immunoglobulin-binding protein derived from *Finegoldia magna*, has already been determined (GenBank Accession No. AAA25612). Protein L consists of a signal peptide (1st to 18th residues of N-terminal side) and a mature peptide (19th to 719th residues). The mature peptide contains 5 antibody-binding domains at N-terminal side. The amino acid sequence of the 5 antibody-binding domains in the mature peptide of Protein L (19th to 463th residues) is shown as SEQ ID NO: 11. Considering the codon frequency of *C. glutamicum*, a nucleotide sequence encoding the antibody-binding domains of Protein L was designed. The designed nucleotide sequence is shown as SEQ ID NO: 12.

Then, an expression cassette of a fusion protein of a signal peptide and the antibody-binding domains of Protein L (hereinafter, also simply referred to as Protein L), in which a DNA encoding 25 amino acid residues consisting of a signal peptide of CspA (also referred to as SlpA) derived from the C. ammoniagenes ATCC 6872 strain (GenBank Accession No. BAB62413) and the DNA of SEQ ID NO: 12 were linked downstream of the promoter of cspB gene of the C. glutamicum ATCC 13869 strain, and KpnI site and BamHI site was further added at the 5'-side and 3'-side termini respectively, was totally synthesized. The synthesized DNA fragment was treated with the restriction enzymes KpnI and BamHI and inserted at KpnI-BamHI site of pPK4 disclosed in Japanese Patent Laid-open (Kokai) No. 9-322774, to construct pPK4 CspAss ProteinL, which is a secretory expression plasmid of Protein L. As a result of nucleotide sequencing of the inserted fragment, it was confirmed that the expected gene encoding Protein L was constructed. Nucleotide sequencing was carried out with BigDye(R) Terminator v3.1 Cycle Sequencing Kit (Applied Biosystems) and 3130 Genetic Analyzer (Applied Biosystems).

(2) Secretory Production of Protein L Using a Strain Deficient In Two-Component Regulatory System Response Regulator Gene hrrA The C. glutamicum YDK010 strain disclosed in WO2002/081694 and the YDK010ΔhrrA strain obtained in Example 1(2) were each transformed with pPK4 CspAss ProteinL obtained in Example 2(1), which is a secretory expression plasmid of Protein L, to obtain strains pPK4_CspAss_ProteinL and YDK010ΔhrrA/pPK4_CspAss_Protein L. The obtained transformants were each cultured on MMTG liquid medium (120 g of glucose, 3 g of $MgSO_4 \cdot 7H_2O$, 30 g of $(NH_4)_2SO_4$, 1.5 g of $KH_2PO_4$, 0.03 g of $FeSO_4 \cdot 7H_2O$, 0.03 g of $MnSO_4 \cdot 5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 25 mg/L of kanamycin at 30° C. for 72 hr. After completion of the culture, 3.0 μL of the culture supernatant obtained by centrifuging each culture broth was subjected to reduced SDS-PAGE, and then staining was carried out with SYPRO Ruby (Life Technologies). As a result, the secretion amount of Protein L was significantly improved in the YDK010ΔhrrA strain, as compared with the YDK010 strain (FIG. 1). After the staining, the band intensity of Protein L was digitized with image analysis software Multi Gauge (FUJIFILM), and the average value of the band intensity observed upon expressing Protein L in the YDK010ΔhrrA strain was calculated as a relative value based on the average value of the band intensity observed upon expressing Protein L in the YDK010 strain which was taken as 1. As a result, it was confirmed that the secretion amount of Protein L was improved to about 2.0-fold in the YDK010ΔhrrA strain, as compared with the YDK010 strain (Table 1). From this, it was revealed that the ΔhrrA mutation (deletion of hrrA gene) is an effective mutation that leads to an improvement of the secretion amount in secretory production of Protein L using the CspA secretion signal, which belongs to the Sec system.

TABLE 1

| Strain | Relative intensity |
|---|---|
| YDK010/pPK4_CspAss_ProteinL | 1.00 |
| YDK010ΔhrrA/pPK4_CspAss_ProteinL | 1.95 |

Example 3

Secretory Production of Liver-Type Fatty Acid-Binding Protein (LFABP) Using Corynebacterium glutamicum Deficient in Two-Component Regulatory System Response Regulator Gene hrrA (1) Construction of Secretory Expression Plasmid of Liver-Type Fatty Acid-Binding protein (LFABP) fused with N-terminal 6 amino acid residues of CspB mature protein The amino acid sequence of Liver-type fatty acid-binding protein of human (hereinafter, referred to as LFABP) has already been determined (RefSeq Accession No. NP_001434). This amino acid sequence is shown as SEQ ID NO: 13. Considering the codon frequency of C. glutamicum, a nucleotide sequence encoding LFABP was designed. In addition, a fusion protein (hereinafter, referred to as CspB6Xa-LFABP) of the CspB signal peptide 30 amino acid residues of the C. glutamicum ATCC 13869 strain, the N-terminal 6 amino acid residues of CspB mature protein of the same strain, the Factor Xa protease recognition sequence IEGR, and LFABP, and a nucleotide sequence encoding the fusion protein were designed. The designed nucleotide sequence encoding the fusion protein is shown as SEQ ID NO: 14, and the amino acid sequence of the fusion protein is shown as SEQ ID NO: 15.

Then, an expression cassette of CspB6Xa-LFABP, in which the promoter of cspB gene of the C. glutamicum ATCC 13869 strain was linked upstream of the DNA of SEQ ID NO: 14, and KpnI site was further added at both the 5'-side and 3'-side termini, was totally synthesized. The synthesized DNA fragment was treated with the restriction enzyme KpnI and inserted at KpnI site of pPK4 disclosed in Japanese Patent Laid-open (Kokai) No. 9-322774, to construct pPK4 CspB6Xa-LFABP, which is a secretory expression plasmid of CspB6Xa-LFABP. As a result of nucleotide sequencing of the inserted fragment, it was confirmed that the expected gene encoding CspB6Xa-LFABP was constructed. Nucleotide sequencing was carried out with Big-Dye(R) Terminator v3.1 Cycle Sequencing Kit (Applied Biosystems) and 3130 Genetic Analyzer (Applied Biosystems).

Figure 2:
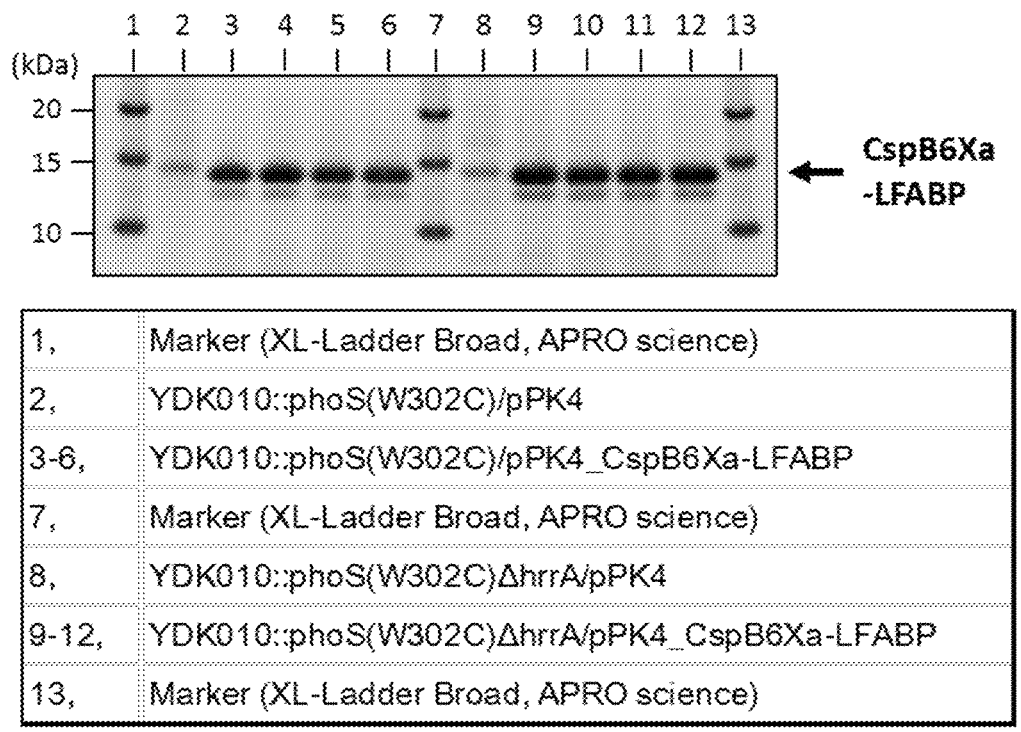
FIG. 2 is a photograph showing the results of SDS-PAGE observed upon expressing CspB6Xa-LFABP (LFABP fused with CspB signal peptide, mature CspB N-terminal sequence, and Factor Xa protease recognition sequence) in the *C. glutamicum* YDK010::phoS(W302C) strain and hrrA-gene-deficient strain thereof.

(2) Secretory Expression Liver-Type Fatty Acid-Binding Protein (LFABP) Using a Strain Deficient In Two-Component Regulatory System Response Regulator Gene hrrA The YDK010::phoS(W302C) strain obtained in Reference example 1(3) and the YDK010::phoS(W302C)ΔhrrA strain obtained in Example 1(2) were each transformed with pPK4 CspB6Xa-LFABP obtained in Example 3(1), which is a secretory expression plasmid of CspB6Xa-LFABP, to obtain strains YDK010::phoS(W302C)/pPK4 CspB6Xa-LFABP and YDK010::phoS(W302C)ΔhrrA/pPK4 CspB6Xa-LFABP. The obtained transformants were each cultured on MMTG liquid medium (120 g of glucose, 3 g of $MgSO_4 \cdot 7H_2O$, 30 g of $(NH_4)_2SO_4$, 1.5 g of $KH_2PO_4$, 0.03 g of $FeSO_4 \cdot 7H_2O$, 0.03 g of $MnSO_4 \cdot 5H_2O$, 0.45 mg of thiamine hydrochloride, 0.45 mg of biotin, 0.15 g of DL-methionine, 0.2 g (as total nitrogen) of soybean hydrolysate solution obtained with HCl, and 50 g of $CaCO_3$, filled up with water to 1 L, and adjusted to pH7.0) containing 25 mg/L of kanamycin at 30° C. for 72 hr. After completion of the culture, 2.0 μL of the culture supernatant obtained by centrifuging each culture broth was subjected to reduced SDS-PAGE, and then staining was carried out with SYPRO Ruby (Life Technologies). As a result, the secretion amount of CspB6Xa-LFABP was significantly improved in the YDK010::phoS(W302C)ΔhrrA strain, as compared with the YDK010::phoS(W302C) strain (FIG. 2). After the staining, the band intensity of CspB6Xa-LFABP was digitized with image analysis software Multi Gauge (FUJIFILM), and the average value of the band intensity observed upon expressing CspB6Xa-LFABP in the YDK010::phoS(W302C)ΔhrrA strain was calculated as a relative value based on the average value of the band intensity observed upon expressing CspB6Xa-LFABP in the YDK010::phoS(W302C) strain which was taken as 1. As a result, it was confirmed that the secretion amount of CspB6Xa-LFABP was improved to about 1.3-fold in the YDK010::phoS(W302C)ΔhrrA strain, as compared with the YDK010::phoS(W302C) strain (Table 2). From this, it was revealed that the ΔhrrA mutation (deletion of hrrA gene) is an effective mutation that leads to an improvement of the secretion amount also in secretory production of CspB6Xa-LFABP in the YDK010::phoS (W302C) strain using the CspA secretion signal, which belongs to the Sec system.

TABLE 2

| Strain | Relative intensity |
| --- | --- |
| YDK010::phoS(W302C)/pPK4_CspB6Xa-LFABP | 1.00 |
| YDK010::phoS(W302C)ΔhrrA/pPK4_CspB6Xa-LFABP | 1.28 |

Example 4

Secretory Production of Green Fluorescent Protein (GFP) Using Corynebacterium glutamicum Deficient in two-Component Regulatory System Response Regulator Gene hrrA (1) Construction of co-expression plasmid of tatABC genes encoding Tat secretion system and gene encoding Green Fluorescent Protein (GFP) added with TorA signal sequence (a) Construction of pPK5, which is a vector corresponding to pPK4 vector of which NaeI recognition sequence was modified In pPK4 disclosed in Japanese Patent Laid-open (Kokai) No. 9-322774, there is the recognition sequence of restriction enzyme NaeI at one site. For modifying this sequence, primers of SEQ ID NOS: 16 and 17, which contain a sequence gcaggc modified from the NaeI recognition sequence gccggc and adjacent sequence thereof in pPK4, were synthesized. Then, PCR was carried out by using primers of SEQ ID NOS: 16 and 17, and pPK4 as the template, to amplify a full length plasmid of about 5.6 kbp. PCR was carried out with Pyrobest(R) DNA polymerase (Takara Bio), and the reaction conditions consisted of 95° C. for 5 min, and 12 cycles of (95° C. for 30 sec. 55° C. for 1 min, and 72° C. for 12 min).

Then, the obtained PCR product was treated with restriction enzyme DpnI, to digest the methylated template DNA. The obtained non-methylated plasmid after the DpnI digestion was introduced into competent cells of E. coli JM109 (Takara Bio), to obtain the plasmid. As a result of nucleotide sequencing, it was confirmed that the expected plasmid in which the NaeI recognition sequence was modified. Nucleotide sequencing was carried out with BigDye(R) Terminator v3.1 Cycle Sequencing Kit (Applied Biosystems) and 3130 Genetic Analyzer (Applied Biosystems). The thus-obtained vector corresponding to the pPK4 vector of which the NaeI recognition sequence was modified was designated as pPK5.

(b) Construction of pPK5-tatABC, which is a vector corresponding to pPK5 vector carrying tatABC genes Then, PCR was carried out by using primers of SEQ ID NOS: 18 and 19, and pVtatABC disclosed in WO2005/103278, which is an amplification plasmid of Tat secretion system, as the template, to amplify a DNA fragment of about 3.7 kbp containing a sequence encoding tatABC genes. The primer of SEQ ID NO: 19 was designed to contain the recognition sequences of restriction enzymes KpnI and ApaI. PCR was carried out with Pyrobest(R) DNA polymerase (Takara Bio), and the reaction conditions were according to the protocol recommended by the manufacturer. This DNA fragment was phosphorylated at the termini with BKL Kit (Takara Bio), treated with KpnI, blunt-ended with BKL Kit (TakaraBio), and inserted into the pPK5 vector that was dephosphorylated at the termini with CIAP (Takara Bio), to construct pPK5-tatABC, which is a vector carrying the tatABC genes. Ligation reaction was carried out with DNA Ligation Kit Ver.2.1 (Takara Bio), and the reaction conditions were according to the protocol recommended by the manufacturer. As a result of nucleotide sequencing of the inserted fragment, it was confirmed that the expected gene was inserted. Nucleotide sequencing was carried out with BigDye(R) Terminator v3.1 Cycle Sequencing Kit (Applied Biosystems) and 3130 Genetic Analyzer (Applied Biosystems).

(c) Construction of pPK6, which is a vector corresponding to pPK5-tatABC vector of which KpnI and XbaI recognition sequences in tatABC genes were modified In the tatABC gene region in the pPK5-tatABC plasmid constructed in (b), there are the recognition sequences of restriction enzymes KpnI and XbaI each at one site. For modifying these sequences, primers of SEQ ID NOS: 20 and 21, which contain a sequence ggaacc modified from the KpnI recognition sequence ggtacc and adjacent sequence thereof in pPK5-tatABC, and primers of SEQ ID NOS: 22 and 23, which contain a sequence tgtaga modified from the XbaI recognition sequence tctaga and adjacent sequence thereof in pPK5-tatABC, were synthesized.

First, for modifying the KpnI recognition sequence in the tatABC gene region, PCR was carried out by using primers of SEQ ID NOS: 20 and 21, and pPK5-tatABC as the template, to amplify a full length plasmid of about 9.4 kbp. PCR was carried out with Pyrobest(R) DNA polymerase (Takara Bio), and the reaction conditions consisted of 95° C. for 5 min, and 12 cycles of (95° C. for 30 sec. 55° C. for 1 min, and 72° C. for 12 min).

Then, the obtained PCR product was treated with restriction enzyme DpnI, to digest the methylated template DNA. The obtained non-methylated plasmid after the DpnI digestion was introduced into competent cells of E. coli JM109 (Takara Bio), to obtain the plasmid. Thus, pPK5-tatAB-CAKpnI, which is a vector of which the KpnI recognition sequences in the tatABC gene region was modified, was constructed.

Then, for modifying the XbaI recognition sequence in the tatABC gene region, PCR was carried out by using primers of SEQ ID NOS: 22 and 23, and pPK5-tatABCAKpnI as the template, to amplify a full length plasmid of about 9.4 kbp. PCR was carried out with Pyrobest(R) DNA polymerase (Takara Bio), and the reaction conditions consisted of 95° C. for 5 min, and 12 cycles of (95° C. for 30 sec. 55° C. for 1 min, and 72° C. for 12 min).

Then, the obtained PCR product was treated with restriction enzyme DpnI, to digest the methylated template DNA. The obtained non-methylated plasmid after the DpnI digestion was introduced into competent cells of E. coli JM109 (Takara Bio), to obtain the plasmid. Thus, pPK5-tatAB-CAKpnIAXbaI, which is a vector of which the XbaI recognition sequences in the tatABC gene region was modified, was constructed. As a result of nucleotide sequencing, it was confirmed that the expected gene was constructed. Nucleotide sequencing was carried out with BigDye(R) Terminator v3.1 Cycle Sequencing Kit (Applied Biosystems) and 3130 Genetic Analyzer (Applied Biosystems).

The thus-obtained vector carrying the tatABC genes based on the pPK4 vector was designated as pPK6.

(d) Construction of secretory expression plasmid of Green Fluorescent Protein (GFP) using pPK6 vector PCR was carried out by using primers of SEQ ID NOS: 24 and 25, and pPTGFP disclosed in Appl. Environ. Microbiol., 72, 7183-7192(2006) as the template, to amplify a DNA fragment of about 1.4 kbp containing a promoter region of cspB gene of the C. glutamicum ATCC 13869 strain, a nucleotide sequence encoding the TorA signal sequence of E. coli, and a nucleotide sequence encoding GFP. PCR was carried out with Pyrobest(R) DNA polymerase (Takara Bio), and the reaction conditions were according to the protocol recommended by the manufacturer. The amplified DNA fragment was subject to agarose gel electrophoresis, an objective band was excised, and the DNA fragment was collected from the gel with Wizard(R) SV Gel and PCR Clean-Up System (Promega). The collected DNA fragment was inserted at KpnI site of pPK6 described in Example 3(1)(c) by infusion reaction, to obtain pPK6_T_GFP, which is a secretory expression plasmid of Green Fluorescent Protein (GFP). The infusion reaction was carried out with In-Fusion(R) HD Cloning Kit (Takara Bio), and the reaction conditions were according to the protocol recommended by the manufacturer. As a result of nucleotide sequencing of the inserted fragment, it was confirmed that the expected gene encoding GFP was constructed. Nucleotide sequencing was carried out with BigDye(R) Terminator v3.1 Cycle Sequencing Kit (Applied Biosystems) and 3130 Genetic Analyzer (Applied Biosystems).

Figure 3:
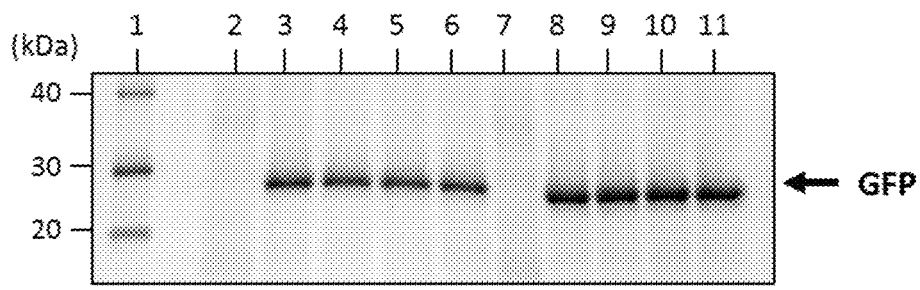
FIG. 3 is a photograph showing the results of SDS-PAGE observed upon expressing GFP (GFP fused with TorA signal peptide) in the *C. glutamicum* YDK010::phoS(W302C) strain and hrrA-gene-deficient strain thereof.

(2) Secretory Expression of Green Fluorescent Protein (GFP) Using a Strain Deficient In two-Component Regulatory System Response Regulator Gene hrrA The YDK010::phoS(W302C) strain obtained in Reference example 1(3) and the YDK010::phoS(W302C)ΔhrrA strain obtained in Example 1(2) were each transformed with pPK6_T_GFP obtained in Example 4(1), which is a secretory expression plasmid of GFP, to obtain strains YDK010::phoS(W302C)/pPK6_T_GFP and YDK010::phoS(W302C)ΔhrrA/pPK6 T GFP. The obtained transformants were each cultured on MMTG liquid medium (120 g of glucose, 3 g of MgSO$_4$.7H$_2$O, 30 g of (NH$_4$)$_2$SO$_4$, 1.5 g of KH$_2$PO$_4$, 0.03 g of FeSO$_4$.7H$_2$O, 0.03 g of MnSO$_4$.5H$_2$O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO$_3$, filled up with water to 1 L, and adjusted to pH7.0) containing 25 mg/L of kanamycin at 30° C. for 72 hr. After completion of the culture, 5.0 μL of the culture supernatant obtained by centrifuging each culture broth was subjected to reduced SDS-PAGE, and then staining was carried out with SYPRO Orange (Life technologies). As a result, the secretion amount of GFP was improved in the YDK010::phoS(W302C)ΔhrrA strain, as compared with the YDK010::phoS(W302C) strain (FIG. 3). After the staining, the band intensity of GFP was digitized with image analysis software Multi Gauge (FUJI-FILM), and the average value of the band intensity observed upon expressing GFP in the YDK010::phoS(W302C)ΔhrrA strain was calculated as a relative value based on the average value of the band intensity observed upon expressing GFP in the YDK010::phoS(W302C) strain which was taken as 1. As a result, it was confirmed that the secretion amount of GFP was improved to about 1.6-fold in the YDK010::phoS (W302C)ΔhrrA strain, as compared with the YDK010::phoS (W302C) strain (Table 3). From this, it was revealed that the ΔhrrA mutation (deletion of hrrA gene) is an effective mutation that leads to an improvement of the secretion amount also in secretory production of GFP in the YDK010::phoS(W302C) strain using the TorA secretion signal, which belongs to the Tat system.

From aforementioned results, it was revealed that the ΔhrrA mutation is a mutation that leads to a significant improvement of the secretion amount a heterologous protein not only when using the Sec secretion system, but also when using the Tat secretion system.

TABLE 3

| Strain | Relative intensity |
|---|---|
| YDK010::phoS(W302C)/pPK6_T_GFP | 1.00 |
| YDK010::phoS(W302C)ΔhrrA/pPK6_T_GFP | 1.60 |

INDUSTRIAL APPLICABILITY

Described herein are heterologous proteins that can be efficiently produced by secretory production.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

EXPLANATION OF SEQUENCE LISTING

SEQ ID NOS:
1: Nucleotide sequence of mutant phoS gene of C. glutamicum YDK0107
2: Amino acid sequence of mutant PhoS protein of C. glutamicum YDK0107
3: Nucleotide sequence of wild-type phoS gene of C. glutamicum YDK010
4: Amino acid sequence of wild-type PhoS protein of C. glutamicum YDK010
5 to 10: Primers
11: Amino acid sequence of the antibody-binding domains of Protein L
12: Nucleotide sequence encoding the antibody-binding domains of Protein L
13: Amino acid sequence of LFABP
14: Nucleotide sequence encoding CspB6Xa-LFABP
15: Amino acid sequence of CspB6Xa-LFABP
16 to 25: Primers
26: Amino acid sequence of PhoS protein of C. glutamicum ATCC 13032

27: Amino acid sequence of PhoS protein of *C. glutamicum* ATCC 14067
28: Amino acid sequence of PhoS protein of *C. callunae*
29: Amino acid sequence of PhoS protein of *C. crenatum*
30: Amino acid sequence of PhoS protein of *C. efficiens*
31: Nucleotide sequence of phoR gene of *C. glutamicum* ATCC 13032
32: Amino acid sequence of PhoR protein of *C. glutamicum* ATCC 13032
33: Nucleotide sequence of cspB gene of *C. glutamicum* ATCC 13869
34: Amino acid sequence of CspB protein of *C. glutamicum* ATCC 13869
35: Nucleotide sequence of tatA gene of *C. glutamicum* ATCC 13032
36: Amino acid sequence of TatA protein of *C. glutamicum* ATCC 13032
37: Nucleotide sequence of tatB gene of *C. glutamicum* ATCC 13032
38: Amino acid sequence of TatB protein of *C. glutamicum* ATCC 13032
39: Nucleotide sequence of tatC gene of *C. glutamicum* ATCC 13032
40: Amino acid sequence of TatC protein of *C. glutamicum* ATCC 13032
41: Amino acid sequence of TorA signal peptide
42: Amino acid sequence of SufI signal peptide
43: Amino acid sequence of PhoD signal peptide
44: Amino acid sequence of LipA signal peptide
45: Amino acid sequence of IMD signal peptide
46 and 47: Amino acid sequence of twin-arginine motif
48: Amino acid sequence of PS1 signal peptide
49: Amino acid sequence of PS2 signal peptide
50: Amino acid sequence of SlpA signal peptide
51: Amino acid sequence of CspB mature protein of *C. glutamicum* ATCC 13869
52 to 59: Amino acid sequences of insertion sequence in one embodiment
60: Recognition sequence of factor Xa protease
61: Recognition sequence of ProTEV protease
62: Nucleotide sequence of hrrS gene of *C. glutamicum* ATCC 13869
63: Amino acid sequence of HrrS protein of *C. glutamicum* ATCC 13869
64: Nucleotide sequence of hrrA gene of *C. glutamicum* ATCC 13869
65: Amino acid sequence of HrrA protein of *C. glutamicum* ATCC 13869

The invention claimed is:

1. A method for producing a heterologous protein comprising:
   culturing a coryneform bacterium having a genetic construct for secretory expression of the heterologous protein; and
   collecting the heterologous protein produced by secretory production,
   wherein the coryneform bacterium has been modified to reduce molecules of an HrrS protein and/or an HrrA protein per cell as compared to a non-modified bacterium,
   wherein the coryneform bacterium is *Corynebacterium glutamicum*,
   wherein the genetic construct comprises, in the direction from 5' to 3', a promoter sequence that functions in the coryneform bacterium, a nucleic acid sequence encoding a signal peptide that functions in the coryneform bacterium, and a nucleic acid sequence encoding the heterologous protein,
   wherein the heterologous protein is expressed as a fusion protein with the signal peptide;
   wherein the molecules of the HrrS protein and/or the HrrA protein per cell is reduced by reducing the expression of a hrrS gene and/or a hrrA gene, or by disrupting a hrrS gene and/or a hrrA,
   wherein the HrrS protein is selected from the group consisting of:
   (a) a protein comprising the amino acid sequence of SEQ ID NO: 63;
   (b) a protein comprising the amino acid sequence of SEQ ID NO: 63, said protein comprising 1 to 10 amino acid residue substitution, deletion, insertion, and/or addition and is a sensor kinase of a HrrSA system; and
   (c) a protein comprising an amino acid sequence that is at least 90% identical to SEQ ID NO: 63, and is a sensor kinase of a HrrSA system, and
   wherein the HrrA protein is selected from the group consisting of:
   (a) a protein comprising the amino acid sequence of SEQ ID NO: 65;
   (b) a protein comprising the amino acid sequence of SEQ ID NO: 65, said protein comprising 1 to 10 amino acid residue substitution, deletion, insertion, and/or addition and is a response regulator of a HrrSA system; and
   (c) a protein comprising an amino acid sequence that is at least 90% identical to SEQ ID NO: 65, and is a response regulator of a HrrSA system.

2. The method of claim 1, wherein the molecules of the HrrA protein per cell is reduced.

3. The method of claim 1, wherein the molecules of the HrrS protein and/or the HrrA protein per cell is reduced by deleting a hrrS gene and/or a hrrA gene.

4. The method of claim 1, wherein the coryneform bacterium has been further modified to harbor a phoS gene encoding a mutant PhoS protein, and wherein the mutant PhoS protein has a mutation of a tryptophan residue corresponding to position 302 in SEP ID NO: 4.

5. The method of claim 4, wherein the mutation is replacing the tryptophan residue corresponding to position 302 in SEQ ID NO: 4 with an amino acid residue other than an aromatic amino acid and a histidine residue.

6. The method of claim 5, wherein the amino acid residue other than the aromatic amino acid and the histidine residue is a lysine residue, alanine residue, valine residue, serine residue, cysteine residue, methionine residue, aspartic acid residue, or asparagine residue.

7. The method of claim 5, wherein the PhoS protein is selected from the group consisting of:
   (a) a protein comprising the amino acid sequence of SEQ ID NO: 4;
   (b) a protein comprising the amino acid sequence of SEQ ID NO: 4, said protein comprising 1 to 10 amino acid residue substitution, deletion, insertion, or addition and is a sensor kinase of a PhoRS system; and
   (c) a protein comprising an amino acid sequence that is at least 90% identical to SEQ ID NO: 4 and is a sensor kinase of a PhoRS system.

8. The method of claim 1, wherein the signal peptide is a Tat-dependent signal peptide.

9. The method of claim 8, wherein the Tat-dependent signal peptide is selected from the group consisting of: a TorA signal peptide, Sufi signal peptide, PhoD signal peptide, LipA signal peptide, and IMD signal peptide.

10. The method of claim 8, wherein the coryneform bacterium has been further modified to express one or more genes encoding a Tat secretion system, and wherein the Tat secretion system is increased as compared with to a non-modified bacterium.

11. The method of claim 10, wherein the one or more genes encoding a Tat secretion system are selected from the group consisting of a tatA gene, tatB gene, tatC gene, and tatE gene.

12. The method of claim 1, wherein the signal peptide is a Sec-dependent signal peptide.

13. The method of claim 12, wherein the Sec-dependent signal peptide is selected from the group consisting of: a PS1 signal peptide, PS2 signal peptide, and SlpA signal peptide.

14. The method of claim 1, wherein the genetic construct further comprises a nucleic acid sequence that encodes an amino acid sequence comprising Gln-Glu-Thr positioned between the nucleic acid sequence encoding the signal peptide and the nucleic acid sequence encoding the heterologous protein.

15. The method of claim 14, wherein the genetic construct further comprises a nucleic acid sequence that encodes a protease recognition sequence used for enzymatic digestion between the nucleic acid sequence encoding the amino acid sequence comprising Gln-Glu-Thr and the nucleic acid sequence encoding the heterologous protein.

16. The method of claim 1, wherein the coryneform bacterium is obtained from *Corynebacterium glutamicum*

AJ12036 (FERM BP-734) or obtained from *Corynebacterium glutamicum* ATCC 13869.

17. The method of claim 1, wherein the coryneform bacterium has been modified to not produce a cell surface layer protein.

* * * * *

SEQUENCE LISTING

```
<160> NUMBER OF SEQ ID NOS: 65

<210> SEQ ID NO 1
<211> LENGTH: 1458
<212> TYPE: DNA
<213> ORGANISM: Corynebacterium glutamicum

<400> SEQUENCE: 1
atggaaaacc cttatgtcgc tgcgctcgat gacgataaaa aagaagtcgg cgcaataaaa        60
gaagcagaaa aagaacctga aataggtccc atcagagctg ccggacgagc cataccgctg       120
cgcacccgca tcattttgat cgtggtgggt atcgccgggc ttggtttgct ggtcaacgcg       180
attgctgttt ccagcctcat gcgtgaagtt tcctataccc gcatggatca agagctagag       240
acctcgatgg ggacgtgggc gcataacgtt gagctgttta atttcgatgg cgtccgccaa       300
gggccaccca gcgattatta tgtggccaag gttttcctg atggatccag cattattttc        360
aacgatgcac aatcggcacc caatctagct gaaaccacca tcggtactgg tccacacact       420
gtggatgctg ctagcggttc tgcctccaac actccgtggc gtgtgatggc ggaaaagaac       480
ggtgacatta tcaccgtggt gggtaaaagc atgggcgtg aaacaaacct gctgtaccga        540
ttggtgatgg tgcagatgat catcggcgcg ctgattctgg ttgctatttt gattacttca       600
ctcttcctag tcagacgctc gttgcggccg ttgagagaag ttgaagagac cgccaccagg       660
attgcgggcg gtgatttgga tcgacgtgtc ccgcagtggc caatgaccac agaagtcgga       720
cagctgtcga atgccctcaa tatcatgttg gagcagctcc aagcctcaat tctgaccgcc       780
cagcaaaaag aagctcagat gcgccgattc gttggcgacg cctcccacga gctccgcaca       840
ccactgacct ctgtgaaggg cttcaccgag ctgtattcat caggtgcaac agatgatgcc       900
aactgtgtca tgtccaagat cggtggcgaa gcccaacgca tgagtgtgct tgtggaagac       960
ctcctgtcac tgacgcgtgc cgaaggccag caaatggaga agcaccgcgt tgacgtgctg      1020
gaactcgcat tggcagtacg cggatccatg cgagcagcct ggccagatcg caccgtcaac      1080
gtgtccaata aagccgagtc cattccagtt gttgaaggcg acccaacccg cctccaccaa      1140
```

-continued

```
gttctcacca acctggttgc caacggactc aaccacggcg gaccggacgc ggaagtcagc    1200
attgagatca acaccgatgg gcaaaacgtg aggattctcg tggcagacaa cggtgtcgga    1260
atgtctgaag aagatgccca gcatatcttc gagcgtttct accgcgccga ttcctcccgc    1320
tcacgcgcat ccggcggatc gggcctcggc cttgcgatca cgaaatccct ggtcgaaggc    1380
cacggcggca cagtcaccgt cgacagcgtg caaggcgaag gcacggtgtt cacgatcacc    1440
ttgccggcgg tttcttaa                                                  1458
```

<210> SEQ ID NO 2
<211> LENGTH: 485
<212> TYPE: PRT
<213> ORGANISM: Corynebacterium glutamicum

<400> SEQUENCE: 2

```
Met Glu Asn Pro Tyr Val Ala Ala Leu Asp Asp Lys Lys Glu Val
1               5                  10                  15

Gly Ala Ile Lys Glu Ala Glu Lys Glu Pro Glu Ile Gly Pro Ile Arg
            20                  25                  30

Ala Ala Gly Arg Ala Ile Pro Leu Arg Thr Arg Ile Ile Leu Ile Val
        35                  40                  45

Val Gly Ile Ala Gly Leu Gly Leu Leu Val Asn Ala Ile Ala Val Ser
    50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
            100                 105                 110

Pro Asp Gly Ser Ser Ile Ile Phe Asn Asp Ala Gln Ser Ala Pro Asn
        115                 120                 125

Leu Ala Glu Thr Thr Ile Gly Thr Gly Pro His Thr Val Asp Ala Ala
    130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Met Val Gln Met Ile Ile Gly Ala Leu Ile
            180                 185                 190

Leu Val Ala Ile Leu Ile Thr Ser Leu Phe Leu Val Arg Arg Ser Leu
        195                 200                 205

Arg Pro Leu Arg Glu Val Glu Glu Thr Ala Thr Arg Ile Ala Gly Gly
    210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Glu Ala Gln Met Arg Arg Phe Val Gly
            260                 265                 270

Asp Ala Ser His Glu Leu Arg Thr Pro Leu Thr Ser Val Lys Gly Phe
        275                 280                 285

Thr Glu Leu Tyr Ser Ser Gly Ala Thr Asp Asp Ala Asn Cys Val Met
    290                 295                 300

Ser Lys Ile Gly Gly Glu Ala Gln Arg Met Ser Val Leu Val Glu Asp
305                 310                 315                 320
```

```
Leu Leu Ser Leu Thr Arg Ala Glu Gly Gln Gln Met Glu Lys His Arg
            325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile
            355                 360                 365

Pro Val Val Glu Gly Asp Pro Thr Arg Leu His Gln Val Leu Thr Asn
            370                 375                 380

Leu Val Ala Asn Gly Leu Asn His Gly Gly Pro Asp Ala Glu Val Ser
385                 390                 395                 400

Ile Glu Ile Asn Thr Asp Gly Gln Asn Val Arg Ile Leu Val Ala Asp
            405                 410                 415

Asn Gly Val Gly Met Ser Glu Glu Asp Ala Gln His Ile Phe Glu Arg
            420                 425                 430

Phe Tyr Arg Ala Asp Ser Ser Arg Ser Arg Ala Ser Gly Gly Ser Gly
            435                 440                 445

Leu Gly Leu Ala Ile Thr Lys Ser Leu Val Glu Gly His Gly Gly Thr
            450                 455                 460

Val Thr Val Asp Ser Val Gln Gly Glu Gly Thr Val Phe Thr Ile Thr
465                 470                 475                 480

Leu Pro Ala Val Ser
            485

<210> SEQ ID NO 3
<211> LENGTH: 1458
<212> TYPE: DNA
<213> ORGANISM: Corynebacterium glutamicum

<400> SEQUENCE: 3
atggaaaacc cttatgtcgc tgcgctcgat gacgataaaa aagaagtcgg cgcaataaaa     60
gaagcagaaa agaacctga aataggtccc atcagagctg ccggacgagc ataccgctg     120 cgcacccgca tcattttgat cgtggtgggt atcgccgggc ttggtttgct ggtcaacgcg    180
attgctgttt ccagcctcat gcgtgaagtt tcctataccc gcatggatca agagctagag    240
acctcgatgg ggacgtgggc gcataacgtt gagctgttta atttcgatgg cgtccgccaa    300
gggccaccca gcgattatta tgtggccaag gttttttcctg atggatccag cattattttc    360
aacgatgcac aatcggcacc caatctagct gaaaccacca tcggtactgg tccacacact    420
gtggatgctg ctagcggttc tgcctccaac actccgtggc gtgtgatggc ggaaaagaac    480
ggtgacatta tcaccgtggt gggtaaaagc atggggcgtg aaacaaacct gctgtaccga    540
ttggtgatgg tgcagatgat catcggcgcg ctgattctgg ttgctatttt gattacttca    600
ctcttcctag tcagacgctc gttgcggccg ttgagagaag ttgaagagac cgccaccagg    660
attgcgggcg gtgatttgga tcgacgtgtc ccgcagtggc aatgaccac agaagtcgga    720 cagctgtcga atgccctcaa tatcatgttg agcagctcc aagcctcaat tctgaccgcc    780
cagcaaaaag aagctcagat gcgccgattc gttggcgacg cctcccacga gctccgcaca    840
ccactgacct ctgtgaaggg cttcaccgag ctgtattcat caggtgcaac agatgatgcc    900
aactgggtca tgtccaagat cggtggcgaa gcccaacgca tgagtgtgct tgtggaagac    960
ctcctgtcac tgacgcgtgc cgaaggccag caaatggaga agcaccgcgt tgacgtgctg    1020
gaactcgcat tggcagtacg cggatccatg cgagcagcct ggccagatcg caccgtcaac    1080
gtgtccaata agccgagtc cattccagtt gttgaaggcg acccaacccg cctccaccaa    1140
```

```
gttctcacca acctggttgc caacggactc aaccacggcg gaccggacgc ggaagtcagc    1200
attgagatca acaccgatgg gcaaaacgtg aggattctcg tggcagacaa cggtgtcgga    1260
atgtctgaag aagatgccca gcatatcttc gagcgtttct accgcgccga ttcctcccgc    1320
tcacgcgcat ccggcggatc gggcctcggc cttgcgatca cgaaatccct ggtcgaaggc    1380
cacggcggca cagtcaccgt cgacagcgtg caaggcgaag gcacggtgtt cacgatcacc    1440
ttgccggcgg tttcttaa                                                  1458
```

<210> SEQ ID NO 4
<211> LENGTH: 485
<212> TYPE: PRT
<213> ORGANISM: Corynebacterium glutamicum

<400> SEQUENCE: 4

```
Met Glu Asn Pro Tyr Val Ala Ala Leu Asp Asp Lys Lys Glu Val
 1               5                  10                  15

Gly Ala Ile Lys Glu Ala Lys Glu Pro Glu Ile Gly Pro Ile Arg
            20                  25                  30

Ala Ala Gly Arg Ala Ile Pro Leu Arg Thr Arg Ile Ile Leu Ile Val
        35                  40                  45

Val Gly Ile Ala Gly Leu Gly Leu Leu Val Asn Ala Ile Ala Val Ser
    50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
            100                 105                 110

Pro Asp Gly Ser Ser Ile Ile Phe Asn Asp Ala Gln Ser Ala Pro Asn
        115                 120                 125

Leu Ala Glu Thr Thr Ile Gly Thr Gly Pro His Thr Val Asp Ala Ala
    130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Met Val Gln Met Ile Ile Gly Ala Leu Ile
            180                 185                 190

Leu Val Ala Ile Leu Ile Thr Ser Leu Phe Leu Val Arg Arg Ser Leu
        195                 200                 205

Arg Pro Leu Arg Glu Val Glu Glu Thr Ala Thr Arg Ile Ala Gly Gly
    210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Glu Ala Gln Met Arg Arg Phe Val Gly
            260                 265                 270

Asp Ala Ser His Glu Leu Arg Thr Pro Leu Thr Ser Val Lys Gly Phe
        275                 280                 285

Thr Glu Leu Tyr Ser Ser Gly Ala Thr Asp Asp Ala Asn Trp Val Met
    290                 295                 300

Ser Lys Ile Gly Gly Glu Ala Gln Arg Met Ser Val Leu Val Glu Asp
```

```
            305                 310                 315                 320
Leu Leu Ser Leu Thr Arg Ala Glu Gly Gln Gln Met Glu Lys His Arg
            325                 330                 335
Val Asp Val Leu Glu Leu Ala Leu Ala Val Arg Gly Ser Met Arg Ala
            340                 345                 350
Ala Trp Pro Asp Arg Thr Val Asn Val Ser Asn Lys Ala Glu Ser Ile
            355                 360                 365
Pro Val Val Glu Gly Asp Pro Thr Arg Leu His Gln Val Leu Thr Asn
            370                 375                 380
Leu Val Ala Asn Gly Leu Asn His Gly Gly Pro Asp Ala Glu Val Ser
385                 390                 395                 400
Ile Glu Ile Asn Thr Asp Gly Gln Asn Val Arg Ile Leu Val Ala Asp
            405                 410                 415
Asn Gly Val Gly Met Ser Glu Glu Asp Ala Gln His Ile Phe Glu Arg
            420                 425                 430
Phe Tyr Arg Ala Asp Ser Ser Arg Ser Arg Ala Ser Gly Gly Ser Gly
            435                 440                 445
Leu Gly Leu Ala Ile Thr Lys Ser Leu Val Glu Gly His Gly Gly Thr
            450                 455                 460
Val Thr Val Asp Ser Val Gln Gly Glu Gly Thr Val Phe Thr Ile Thr
465                 470                 475                 480
Leu Pro Ala Val Ser
            485

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
aggcagcaaa acaccgagga ctcaa                                         25

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
cgggcttggt ttgctggtca acgcg                                         25

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gaattgggca tcgtccacga aa                                            22

<210> SEQ ID NO 8
<211> LENGTH: 23
<212> TYPE: DNA
<213> ORGANISM: Artificial Sequence
<220> FEATURE:
<223> OTHER INFORMATION: primer
```

```
<400> SEQUENCE: 8
caacgatcag gattgtcgtc atg                                      23

<210> SEQ ID NO 9
<211> LENGTH: 45
<212> TYPE: DNA
<213> ORGANISM: Artificial Sequence
<220> FEATURE:
<223> OTHER INFORMATION: primer

<400> SEQUENCE: 9
catgacgaca atcctgatcg ttggcgtgga ttgggctaca aattc              45

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
gctaattatg ggcatccaag gg                                       22

<210> SEQ ID NO 11
<211> LENGTH: 445
<212> TYPE: PRT
<213> ORGANISM: Finegoldia magna

<400> SEQUENCE: 11
```

| Ala | Asp | Glu | Pro | Ile | Asp | Leu | Glu | Lys | Leu | Glu | Glu | Lys | Arg | Asp | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Glu Asn Val Gly Asn Leu Pro Lys Phe Asp Asn Glu Val Lys Asp Gly
           20                  25                  30

Ser Glu Asn Pro Met Ala Lys Tyr Pro Asp Phe Asp Asp Glu Ala Ser
       35                  40                  45

Thr Arg Phe Glu Thr Glu Asn Asn Glu Phe Glu Lys Lys Val Val
   50                  55                  60

Ser Asp Asn Phe Phe Asp Gln Ser Glu His Pro Phe Val Glu Asn Lys
65                  70                  75                  80

Glu Glu Thr Pro Glu Thr Pro Glu Thr Asp Ser Glu Glu Val Thr
               85                  90                  95

Ile Lys Ala Asn Leu Ile Phe Ala Asn Gly Ser Thr Gln Thr Ala Glu
           100                 105                 110

Phe Lys Gly Thr Phe Glu Lys Ala Thr Ser Glu Ala Tyr Ala Tyr Ala
       115                 120                 125

Asp Thr Leu Lys Lys Asp Asn Gly Glu Tyr Thr Val Asp Val Ala Asp
   130                 135                 140

Lys Gly Tyr Thr Leu Asn Ile Lys Phe Ala Gly Lys Glu Lys Thr Pro
145                 150                 155                 160

Glu Glu Pro Lys Glu Glu Val Thr Ile Lys Ala Asn Leu Ile Tyr Ala
               165                 170                 175

Asp Gly Lys Thr Gln Thr Ala Glu Phe Lys Gly Thr Phe Glu Glu Ala
           180                 185                 190

Thr Ala Glu Ala Tyr Arg Tyr Ala Asp Ala Leu Lys Lys Asp Asn Gly
       195                 200                 205

Glu Tyr Thr Val Asp Val Ala Asp Lys Gly Tyr Thr Leu Asn Ile Lys
   210                 215                 220

Phe Ala Gly Lys Glu Lys Thr Pro Glu Glu Pro Lys Glu Glu Val Thr

```
                225                 230                 235                 240
        Ile Lys Ala Asn Leu Ile Tyr Ala Asp Gly Lys Thr Gln Thr Ala Glu
                        245                 250                 255

Phe Lys Gly Thr Phe Glu Glu Ala Thr Ala Glu Ala Tyr Arg Tyr Ala
                        260                 265                 270

Asp Leu Leu Ala Lys Glu Asn Gly Lys Tyr Thr Val Asp Val Ala Asp
                        275                 280                 285

Lys Gly Tyr Thr Leu Asn Ile Lys Phe Ala Gly Lys Glu Lys Thr Pro
                        290                 295                 300

Glu Glu Pro Lys Glu Glu Val Thr Ile Lys Ala Asn Leu Ile Tyr Ala
        305                 310                 315                 320

Asp Gly Lys Thr Gln Thr Ala Glu Phe Lys Gly Thr Phe Ala Glu Ala
                        325                 330                 335

Thr Ala Glu Ala Tyr Arg Tyr Ala Asp Leu Leu Ala Lys Glu Asn Gly
                        340                 345                 350

Lys Tyr Thr Ala Asp Leu Glu Asp Gly Gly Tyr Thr Ile Asn Ile Arg
                        355                 360                 365

Phe Ala Gly Lys Lys Val Asp Glu Lys Pro Glu Glu Lys Glu Gln Val
                        370                 375                 380

Thr Ile Lys Glu Asn Ile Tyr Phe Glu Asp Gly Thr Val Gln Thr Ala
        385                 390                 395                 400

Thr Phe Lys Gly Thr Phe Ala Glu Ala Thr Ala Glu Ala Tyr Arg Tyr
                        405                 410                 415

Ala Asp Leu Leu Ser Lys Glu His Gly Lys Tyr Thr Ala Asp Leu Glu
                        420                 425                 430

Asp Gly Gly Tyr Thr Ile Asn Ile Arg Phe Ala Gly Lys
                        435                 440                 445

<210> SEQ ID NO 12
<211> LENGTH: 1338
<212> TYPE: DNA
<213> ORGANISM: Finegoldia magna

<400> SEQUENCE: 12
gcggacgagc ctattgatct ggagaagttg gaggagaagc gtgataaaga gaacgtgggc         60
aacctgccta agttcgataa cgaggtcaag gatggctccg aaaacccgat ggcgaagtac        120
ccagacttcg atgacgaggc atctacccgc ttcgagaccg aaaacaacga attcgaagag        180
aagaaagtgg tctccgataa cttcttcgac cagtctgagc ccctttcgt cgaaaacaag        240 gaagagaccc cagagacccc tgaaaccgat tccgaagagg aagttaccat caaggcgaac        300
ctgattttcg caaacggctc cacccagacc gctgagttca gggcacctt cgagaaagcc        360 acctctgaag catacgctta cgccgatacc cttaagaaag acaacggcga atacaccgtt        420
gatgtggcgg acaagggcta caccttgaac atcaaattcg caggcaagga gaaaaccccg        480
gaggaaccaa aggaggaagt gaccatcaaa gctaacctca tctacgccga cggcaagacc        540
cagaccgcag agttcaaagg caccttcgag gaagcgaccg cagaagctta ccgctacgcc        600
gatgcgctga gaaagacaa cggtgaatac accgtcgatg ttgctgacaa gggctacacc        660
ctcaacatca gttcgccgg caaggagaaa cccctgagg aaccgaagga ggaagtcacc        720
atcaaagcga accttatcta cgcagatggc aagactcaaa ctgctgagtt caagggcacc        780
tttgaggaag caaccgctga agcctaccgt tacgcggacc tgctcgcaaa ggagaacggc        840
aaatacaccg tggatgtcgc agataagggc tacacccta acatcaagtt cgctggcaag        900
```

| | |
|---|---|
| gaaaagaccc cagaggaacc taaggaggaa gttaccatca aagctaactt gatctacgcc | 960 |
| gatggcaaga cccagaccgc cgagttcaag ggcacctttg cggaggctac cgcagaagcc | 1020 |
| taccgctacg ctgacctttt ggccaaagaa aacggcaaat acaccgccga tctggaagac | 1080 |
| ggcggttaca ccatcaacat ccgcttcgca ggcaagaagg ttgatgagaa gccagaggaa | 1140 |
| aaagaacagg tgaccatcaa ggagaacatc tacttcgaag acggcaccgt ccagaccgct | 1200 |
| accttcaagg gcaccttcgc ggaggctacc gccgaagcct accgttacgc agatctgctc | 1260 |
| tccaaggaac acggcaaata caccgctgac ctggaagacg gcggctacac catcaacatt | 1320 |
| cgtttcgctg gcaagtga | 1338 |

<210> SEQ ID NO 13
<211> LENGTH: 127
<212> TYPE: PRT
<213> ORGANISM: Homo sapiens

<400> SEQUENCE: 13

Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
        115                 120                 125

<210> SEQ ID NO 14
<211> LENGTH: 504
<212> TYPE: DNA
<213> ORGANISM: Homo sapiens

<400> SEQUENCE: 14

| | |
|---|---|
| atgtttaaca accgtatccg cactgcagct ctcgctggtg caatcgcaat ctccaccgca | 60 |
| gcttccggcg tagctatccc agcattcgct caggagacca acccaaccat cgagggccgc | 120 |
| atgtccttct ccggcaagta ccagctgcag tcccaggaaa acttcgaggc attcatgaag | 180 |
| gctatcggtc tgccagaaga gctcatccag aagggcaagg atatcaaggg tgtttccgaa | 240 |
| atcgtgcaga acggcaagca cttcaagttc accatcaccg caggttccaa ggtcatccag | 300 |
| aacgagttca ccgttggcga agagtgcgaa ctcgagacca tgaccggtga aaaggttaag | 360 |
| accgtggtcc agctggaggg cgacaacaag ctcgtgacca cttcaagaa catcaagtcc | 420 |
| gtcaccgaac tgaacggcga tatcatcacc aacaccatga cctcggtga catcgtgttc | 480 |
| aagcgcatct ccaagcgtat ctaa | 504 |

<210> SEQ ID NO 15
<211> LENGTH: 167
<212> TYPE: PRT
<213> ORGANISM: Homo sapiens

<400> SEQUENCE: 15

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Ile Glu Gly Arg Met Ser Phe Ser Gly Lys Tyr Gln
        35                  40                  45

Leu Gln Ser Gln Glu Asn Phe Glu Ala Phe Met Lys Ala Ile Gly Leu
    50                  55                  60

Pro Glu Glu Leu Ile Gln Lys Gly Lys Asp Ile Lys Gly Val Ser Glu
65                  70                  75                  80

Ile Val Gln Asn Gly Lys His Phe Lys Phe Thr Ile Thr Ala Gly Ser
                85                  90                  95

Lys Val Ile Gln Asn Glu Phe Thr Val Gly Glu Cys Glu Leu Glu
            100                 105                 110

Thr Met Thr Gly Glu Lys Val Lys Thr Val Val Gln Leu Glu Gly Asp
        115                 120                 125

Asn Lys Leu Val Thr Thr Phe Lys Asn Ile Lys Ser Val Thr Glu Leu
130                 135                 140

Asn Gly Asp Ile Ile Thr Asn Thr Met Thr Leu Gly Asp Ile Val Phe
145                 150                 155                 160

Lys Arg Ile Ser Lys Arg Ile
                165
```

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
cgagccacca ggcaggcggg aaaatcg                    27

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
cgatttcccc gcctgcctgg tggctcg                    27

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
cccgcttgat cattccttta agg                        23

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
aatgggccct ttggtacccc taaataatat cggtcc                              36

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20
cgtgctctag gggaaccgtg cgttccc                                        27

<210> SEQ ID NO 21
<211> LENGTH: 27
<212> TYPE: DNA
<213> ORGANISM: Artificial Sequence
<220> FEATURE:
<223> OTHER INFORMATION: primer

<400> SEQUENCE: 21
gggaacgcac ggttccccta gagcacg                                        27

<210> SEQ ID NO 22
<211> LENGTH: 27
<212> TYPE: DNA
<213> ORGANISM: Artificial Sequence
<220> FEATURE:
<223> OTHER INFORMATION: primer

<400> SEQUENCE: 22
cgacgctgaa gttgtagaga tcatccg                                        27

<210> SEQ ID NO 23
<211> LENGTH: 27
<212> TYPE: DNA
<213> ORGANISM: Artificial Sequence
<220> FEATURE:
<223> OTHER INFORMATION: primer

<400> SEQUENCE: 23
cggatgatct ctacaacttc agcgtcg                                        27

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
cgatattatt tagggaaatt cctgtgaatt agctga                              36

<210> SEQ ID NO 25
<211> LENGTH: 37
<212> TYPE: DNA
<213> ORGANISM: Artificial Sequence
<220> FEATURE:
<223> OTHER INFORMATION: primer

<400> SEQUENCE: 25
ggaatgggcc ctttgttatt tgtatagttc atccatg                             37

<210> SEQ ID NO 26

```
<211> LENGTH: 485
<212> TYPE: PRT
<213> ORGANISM: Corynebacterium glutamicum

<400> SEQUENCE: 26
```

| | | | | | | | | | | | | | | |
|---|---|---|---|---|---|---|---|---|---|---|---|---|---|---|
| Met | Glu | Asn | Pro | Tyr | Val | Ala | Ala | Leu | Asp | Asp | Glu | Asn | Gln | Glu | Val |
| 1 | | | | 5 | | | | | 10 | | | | | 15 | |
| Gly | Val | Lys | Lys | Glu | Ala | Glu | Lys | Glu | Pro | Glu | Ile | Gly | Pro | Ile | Arg |
| | | | 20 | | | | | 25 | | | | | 30 | | |
| Ala | Ala | Gly | Arg | Ala | Ile | Pro | Leu | Arg | Thr | Arg | Ile | Ile | Leu | Ile | Val |
| | | | 35 | | | | | 40 | | | | | 45 | | |
| Val | Gly | Ile | Ala | Gly | Leu | Gly | Leu | Leu | Val | Asn | Ala | Ile | Ala | Val | Ser |
| | 50 | | | | | 55 | | | | | 60 | | | | |
| Ser | Leu | Met | Arg | Glu | Val | Ser | Tyr | Thr | Arg | Met | Asp | Gln | Glu | Leu | Glu |
| 65 | | | | | 70 | | | | | 75 | | | | | 80 |
| Thr | Ser | Met | Gly | Thr | Trp | Ala | His | Asn | Val | Glu | Leu | Phe | Asn | Phe | Asp |
| | | | | 85 | | | | | 90 | | | | | 95 | |
| Gly | Val | Arg | Gln | Gly | Pro | Ser | Asp | Tyr | Tyr | Val | Ala | Lys | Val | Phe | |
| | | | 100 | | | | | 105 | | | | | 110 | | |
| Pro | Asp | Gly | Ser | Ser | Ile | Ile | Phe | Asn | Asp | Ala | Gln | Ser | Ala | Pro | Asp |
| | | 115 | | | | | 120 | | | | | 125 | | | |
| Leu | Ala | Glu | Thr | Thr | Ile | Gly | Thr | Gly | Pro | His | Thr | Val | Asp | Ala | Ala |
| | 130 | | | | | 135 | | | | | 140 | | | | |
| Ser | Gly | Ser | Ala | Ser | Asn | Thr | Pro | Trp | Arg | Val | Met | Ala | Glu | Lys | Asn |
| 145 | | | | | 150 | | | | | 155 | | | | | 160 |
| Gly | Asp | Ile | Ile | Thr | Val | Val | Gly | Lys | Ser | Met | Gly | Arg | Glu | Thr | Asn |
| | | | | 165 | | | | | 170 | | | | | 175 | |
| Leu | Leu | Tyr | Arg | Leu | Val | Met | Val | Gln | Met | Ile | Ile | Gly | Ala | Leu | Ile |
| | | | 180 | | | | | 185 | | | | | 190 | | |
| Leu | Val | Ala | Ile | Leu | Ile | Thr | Ser | Leu | Phe | Leu | Val | Arg | Arg | Ser | Leu |
| | | 195 | | | | | 200 | | | | | 205 | | | |
| Arg | Pro | Leu | Arg | Glu | Val | Glu | Glu | Thr | Ala | Thr | Arg | Ile | Ala | Gly | Gly |
| | 210 | | | | | 215 | | | | | 220 | | | | |
| Asp | Leu | Asp | Arg | Arg | Val | Pro | Gln | Trp | Pro | Met | Thr | Thr | Glu | Val | Gly |
| 225 | | | | | 230 | | | | | 235 | | | | | 240 |
| Gln | Leu | Ser | Asn | Ala | Leu | Asn | Ile | Met | Leu | Glu | Gln | Leu | Gln | Ala | Ser |
| | | | | 245 | | | | | 250 | | | | | 255 | |
| Ile | Leu | Thr | Ala | Gln | Gln | Lys | Glu | Ala | Gln | Met | Arg | Arg | Phe | Val | Gly |
| | | | 260 | | | | | 265 | | | | | 270 | | |
| Asp | Ala | Ser | His | Glu | Leu | Arg | Thr | Pro | Leu | Thr | Ser | Val | Lys | Gly | Phe |
| | | 275 | | | | | 280 | | | | | 285 | | | |
| Thr | Glu | Leu | Tyr | Ser | Ser | Gly | Ala | Thr | Asp | Asp | Ala | Asn | Trp | Val | Met |
| | 290 | | | | | 295 | | | | | 300 | | | | |
| Ser | Lys | Ile | Gly | Gly | Glu | Ala | Gln | Arg | Met | Ser | Val | Leu | Val | Glu | Asp |
| 305 | | | | | 310 | | | | | 315 | | | | | 320 |
| Leu | Leu | Ser | Leu | Thr | Arg | Ala | Glu | Gly | Gln | Gln | Met | Glu | Lys | His | Arg |
| | | | | 325 | | | | | 330 | | | | | 335 | |
| Val | Asp | Val | Leu | Glu | Leu | Ala | Leu | Ala | Val | Arg | Gly | Ser | Met | Arg | Ala |
| | | | 340 | | | | | 345 | | | | | 350 | | |
| Ala | Trp | Pro | Asp | Arg | Thr | Val | Asn | Val | Ser | Asn | Lys | Ala | Glu | Ser | Ile |
| | | 355 | | | | | 360 | | | | | 365 | | | |
| Pro | Val | Val | Lys | Gly | Asp | Pro | Thr | Arg | Leu | His | Gln | Val | Leu | Thr | Asn |
| | 370 | | | | | 375 | | | | | 380 | | | | |
| Leu | Val | Ala | Asn | Gly | Leu | Asn | His | Gly | Gly | Pro | Asp | Ala | Glu | Val | Ser |

```
            385                 390                 395                 400
Ile Glu Ile Asn Thr Asp Gly Gln Asn Val Arg Ile Leu Val Ala Asp
                    405                 410                 415

Asn Gly Val Gly Met Ser Glu Glu Asp Ala Gln His Ile Phe Glu Arg
            420                 425                 430

Phe Tyr Arg Ala Asp Ser Ser Arg Ser Arg Ala Ser Gly Gly Ser Gly
                    435                 440                 445

Leu Gly Leu Ala Ile Thr Lys Ser Leu Val Glu Gly His Gly Gly Thr
            450                 455                 460

Val Thr Val Asp Ser Val Gln Gly Glu Gly Thr Val Phe Thr Ile Thr
465                 470                 475                 480

Leu Pro Ala Val Ser
            485

<210> SEQ ID NO 27
<211> LENGTH: 485
<212> TYPE: PRT
<213> ORGANISM: Corynebacterium glutamicum

<400> SEQUENCE: 27

Met Glu Asn Pro Tyr Val Ala Ala Leu Asp Asp Glu Asn Gln Glu Val
1               5                   10                  15

Gly Val Lys Lys Glu Ala Glu Lys Glu Pro Glu Ile Gly Pro Ile Arg
            20                  25                  30

Ala Ala Gly Arg Ala Ile Pro Leu Arg Thr Arg Ile Ile Leu Ile Val
                35                  40                  45

Val Gly Ile Ala Gly Leu Leu Leu Val Asn Ala Ile Ala Val Ser
        50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
            100                 105                 110

Pro Asp Gly Ser Ser Ile Ile Phe Asn Asp Ala Gln Ser Ala Pro Asp
        115                 120                 125

Leu Ala Glu Thr Thr Ile Gly Thr Gly Pro His Thr Val Asp Ala Ala
    130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Val Val Gln Met Ile Ile Gly Ala Leu Ile
            180                 185                 190

Leu Val Ala Ile Leu Ile Thr Ser Leu Phe Leu Val Arg Arg Ser Leu
        195                 200                 205

Arg Pro Leu Arg Glu Val Glu Thr Ala Thr Arg Ile Ala Gly Gly
    210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Glu Ala Gln Met Arg Arg Phe Val Gly
            260                 265                 270
```

Asp Ala Ser His Glu Leu Arg Thr Pro Leu Thr Ser Val Lys Gly Phe
            275                 280                 285

Thr Glu Leu Tyr Ser Ser Gly Ala Thr Asp Asp Ala Asn Trp Val Met
        290                 295                 300

Ser Lys Ile Gly Gly Glu Ala Gln Arg Met Ser Val Leu Val Glu Asp
305                 310                 315                 320

Leu Leu Ser Leu Thr Arg Ala Glu Gly Gln Gln Met Glu Lys His Arg
                325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile
        355                 360                 365

Pro Val Val Glu Gly Asp Pro Thr Arg Leu His Gln Val Leu Thr Asn
    370                 375                 380

Leu Val Ala Asn Gly Leu Asn His Gly Gly Pro Asp Ala Glu Val Ser
385                 390                 395                 400

Ile Glu Ile Asn Thr Asp Gly Gln Asn Val Arg Ile Leu Val Ala Asp
                405                 410                 415

Asn Gly Val Gly Met Ser Glu Glu Asp Ala Gln His Ile Phe Glu Arg
            420                 425                 430

Phe Tyr Arg Ala Asp Ser Ser Arg Ser Arg Ala Ser Gly Gly Ser Gly
        435                 440                 445

Leu Gly Leu Ala Ile Thr Lys Ser Leu Val Glu Gly His Gly Gly Thr
    450                 455                 460

Val Thr Val Asp Ser Val Gln Gly Glu Gly Thr Val Phe Thr Ile Thr
465                 470                 475                 480

Leu Pro Ala Val Ser
                485

<210> SEQ ID NO 28
<211> LENGTH: 504
<212> TYPE: PRT
<213> ORGANISM: Corynebacterium callunae

<400> SEQUENCE: 28

Met Glu Asn Pro Tyr Val Ala Ala Leu Asp Lys Asn Ser Asn Phe Gly
1               5                   10                  15

Ala Lys Asp Thr Asp Ser Ala Val Ser Asp Ser Thr Glu Val Ser Gln
            20                  25                  30

Asn Asn Asp Gly Ile Gly Thr Pro Ala Thr Ala Glu Pro Lys Val Gly
        35                  40                  45

Pro Ile Arg Thr Ala Gly Arg Ala Met Pro Leu Arg Thr Arg Ile Ile
    50                  55                  60

Leu Leu Val Val Gly Ile Ala Gly Leu Gly Leu Val Asn Ala Val
65                  70                  75                  80

Ala Val Ser Ser Leu Met Arg Glu Val Ser Tyr Thr Arg Met Asp Gln
                85                  90                  95

Asp Leu Glu Ser Ala Met Gly Thr Trp Val Arg Asn Val Glu Leu Phe
            100                 105                 110

Asn Phe Asp Gly Val Arg Gln Gly Pro Pro Ser Asp Tyr Tyr Val Ala
        115                 120                 125

Lys Val Phe Pro Asp Gly Ser Ser Ile Ile Phe Asn Asp Ala Glu Ser
    130                 135                 140

Ala Pro Asp Leu Gly Gln Thr Thr Ile Gly Thr Gly Pro His Thr Val
145                 150                 155                 160

```
Glu Ala Ala Glu Gly Ser Ala Ser Ser Thr His Trp Arg Val Met Ala
                165                 170                 175

Ala Lys Asn Gly Asp Val Ile Thr Val Val Gly Lys Ser Met Gly Arg
            180                 185                 190

Glu Ser Thr Leu Leu Tyr Arg Leu Val Val Gln Met Val Ile Gly
        195                 200                 205

Val Leu Ile Leu Ile Ala Ile Leu Ile Gly Ser Phe Phe Leu Val Arg
    210                 215                 220

Arg Ser Leu Lys Pro Leu Arg Glu Val Glu Glu Thr Ala Ser Arg Ile
225                 230                 235                 240

Ala Gly Gly Glu Leu Asp Arg Arg Val Pro Gln Trp Pro Met Thr Thr
                245                 250                 255

Glu Val Gly Gln Leu Ala Asn Ala Leu Asn Ile Met Leu Glu Gln Leu
            260                 265                 270

Gln Thr Ser Ile Met Asn Ala Gln Gln Lys Glu Ala Gln Met Arg Arg
        275                 280                 285

Phe Val Gly Asp Ala Ser His Glu Leu Arg Thr Pro Leu Thr Ser Val
    290                 295                 300

Lys Gly Phe Thr Glu Leu Tyr Ser Ser Gly Ala Thr Gln Asp Ala Asp
305                 310                 315                 320

Trp Val Leu Ser Lys Ile Gly Gly Glu Ala Gln Arg Met Ser Val Leu
                325                 330                 335

Val Glu Asp Leu Leu Ser Leu Thr Arg Ala Glu Gly Gln Gln Met Glu
            340                 345                 350

Lys His Arg Val Asp Met Leu Glu Leu Ala Leu Ala Val Arg Gly Ser
        355                 360                 365

Leu Lys Ala Ala Trp Pro Asp Arg Thr Val Asn Val Ala Asn Arg Ser
    370                 375                 380

Glu Asn Ile Pro Val Val Glu Gly Asp Pro Thr Arg Leu His Gln Val
385                 390                 395                 400

Leu Thr Asn Leu Val Ala Asn Gly Leu Asn His Gly Pro Glu Ala
                405                 410                 415

Glu Val Asn Ile Gln Val Glu Thr Ala Asp Lys Val Lys Ile Leu
            420                 425                 430

Val Ile Asp Asn Gly Val Gly Met Ser Lys Glu Asp Ala Glu His Ile
    435                 440                 445

Phe Glu Arg Phe Tyr Arg Ala Asp Thr Ser Arg Ser Arg Ala Ser Gly
450                 455                 460

Gly Ser Gly Leu Gly Leu Ala Ile Thr Lys Ser Leu Val Glu Gly His
465                 470                 475                 480

Gly Gly Thr Ile Thr Val Asp Ser Glu Leu Lys Gly Thr Val Phe
                485                 490                 495

Ser Ile Ile Leu Pro Ala Ala Glu
            500

<210> SEQ ID NO 29
<211> LENGTH: 458
<212> TYPE: PRT
<213> ORGANISM: Corynebacterium crenatum

<400> SEQUENCE: 29

Ile Gly Pro Ile Arg Ala Ala Gly Arg Ala Ile Pro Leu Arg Thr Arg
1               5                   10                  15

Ile Ile Leu Ile Val Val Gly Ile Ala Gly Leu Gly Leu Leu Val Asn
```

```
                20                  25                  30
Ala Ile Ala Val Ser Ser Leu Met Arg Glu Val Ser Tyr Thr Arg Met
             35                  40                  45

Asp Gln Glu Leu Glu Thr Ser Met Gly Thr Trp Ala His Asn Val Glu
 50                  55                  60

Leu Phe Asn Phe Asp Gly Val Arg Gln Gly Pro Pro Ser Asp Tyr Tyr
 65                  70                  75                  80

Val Ala Lys Val Phe Pro Asp Gly Ser Ser Ile Ile Phe Asn Asp Ala
                 85                  90                  95

Gln Ser Ala Pro Asp Leu Ala Glu Thr Thr Ile Gly Thr Gly Pro His
                100                 105                 110

Thr Val Asp Ala Ala Ser Gly Ser Ala Ser Asn Thr Pro Trp Arg Val
            115                 120                 125

Met Ala Glu Lys Asn Gly Asp Ile Ile Thr Val Gly Lys Ser Met
            130                 135                 140

Gly Arg Glu Thr Asn Leu Leu Tyr Arg Leu Val Met Val Gln Met Ile
145                 150                 155                 160

Ile Gly Ala Leu Ile Leu Val Ala Ile Leu Ile Thr Ser Leu Phe Leu
                165                 170                 175

Val Arg Arg Ser Leu Arg Pro Leu Arg Glu Val Glu Thr Ala Thr
            180                 185                 190

Arg Ile Ala Gly Gly Asp Leu Asp Arg Arg Val Pro Gln Trp Pro Met
            195                 200                 205

Thr Thr Glu Val Gly Gln Leu Ser Asn Ala Leu Asn Ile Met Leu Glu
            210                 215                 220

Gln Leu Gln Ala Ser Ile Leu Ser Ala Gln Gln Lys Glu Ala Gln Met
225                 230                 235                 240

Arg Arg Phe Val Gly Asp Ala Ser His Glu Leu Arg Thr Pro Leu Thr
                245                 250                 255

Ser Val Lys Gly Phe Thr Glu Leu Tyr Ser Ser Gly Ala Thr Asp Asp
            260                 265                 270

Ala Asn Trp Val Met Ser Lys Ile Gly Gly Glu Ala Gln Arg Met Ser
            275                 280                 285

Val Leu Val Glu Asp Leu Leu Ser Leu Thr Arg Ala Glu Gly Gln Gln
            290                 295                 300

Met Glu Lys His Arg Val Asp Val Leu Glu Leu Ala Leu Ala Val Arg
305                 310                 315                 320

Gly Ser Met Arg Ala Ala Trp Pro Asp Arg Thr Val Asn Val Ser Asn
                325                 330                 335

Lys Ala Ala Ser Ile Pro Val Val Glu Gly Asp Pro Thr Arg Leu His
            340                 345                 350

Gln Val Leu Thr Asn Leu Val Ala Asn Gly Leu Asn His Gly Gly Pro
            355                 360                 365

Asp Ala Glu Val Ser Ile Glu Ile Asn Thr Asp Gly Gln Asn Val Arg
            370                 375                 380

Ile Leu Val Ala Asp Asn Gly Val Gly Met Ser Glu Glu Asp Ala Gln
385                 390                 395                 400

His Ile Phe Glu Arg Phe Tyr Arg Ala Asp Ser Ser Arg Ser Arg Ala
                405                 410                 415

Ser Gly Gly Ser Gly Leu Gly Leu Ala Ile Thr Lys Ser Leu Val Glu
            420                 425                 430

Gly His Gly Gly Thr Val Thr Val Asp Ser Val Gln Gly Glu Gly Thr
            435                 440                 445
```

Val Phe Thr Ile Thr Leu Pro Ala Val Ser
    450                 455

<210> SEQ ID NO 30
<211> LENGTH: 471
<212> TYPE: PRT
<213> ORGANISM: Corynebacterium efficiens

<400> SEQUENCE: 30

Met Thr Ala Pro Glu Asn Pro His Ala Gln Val Thr Pro Val Gly Arg
1               5                   10                  15

Phe Arg Gln Ala Ala Arg Gly Val Pro Leu Arg Thr Arg Ile Ile Leu
            20                  25                  30

Leu Val Val Gly Ile Ala Gly Leu Gly Leu Leu Val Asn Ala Ile Ala
        35                  40                  45

Val Ser Ser Leu Met Arg Glu Val Ser Tyr Ser Arg Met Asp Gln Glu
    50                  55                  60

Leu Glu Ser Ala Met Asn Ser Trp Ala Gln Thr Ala Glu Leu Phe Gly
65                  70                  75                  80

Ser Ile Thr Leu Gly Pro Pro Ser Asp Tyr Tyr Val Val Arg Ile Phe
                85                  90                  95

Pro Asp Gly Ser His Met Val Phe Asn Gln Ser Asp Ser Ala Pro Asp
            100                 105                 110

Leu Gly Glu Thr Thr Ile Gly Ile Gly Pro His Thr Ala Ser Ala Ala
        115                 120                 125

Pro Gly Ser Ser Ser Val Pro Trp Arg Val Ile Ala Ile Ser Asp
    130                 135                 140

Asn Gly Thr Ile Thr Val Val Gly Lys Ser Leu Ala Pro Glu Ser Met
145                 150                 155                 160

Leu Leu Tyr Arg Leu Val Ile Val Gln Leu Val Ile Gly Met Leu Ile
                165                 170                 175

Val Val Ala Ile Leu Leu Ser Ser Leu Tyr Leu Val Asn Arg Ser Leu
            180                 185                 190

Arg Pro Leu Arg Glu Val Glu Lys Thr Ala Lys Ser Ile Ala Gly Gly
        195                 200                 205

Asp Leu Asp Arg Arg Val Pro Gln Trp Pro Met Thr Thr Glu Val Gly
    210                 215                 220

Gln Leu Ala Asn Ala Leu Asn Ile Met Leu Glu Gln Leu Gln Ala Ser
225                 230                 235                 240

Ile Leu Ser Ala Gln Glu Lys Glu Ser Gln Met Arg Arg Phe Val Gly
                245                 250                 255

Asp Ala Ser His Glu Leu Arg Thr Pro Leu Thr Ser Val Lys Gly Tyr
            260                 265                 270

Ser Glu Leu Tyr His Ser Gly Ala Thr Arg Asp Ala Asp Trp Val Leu
        275                 280                 285

Ser Lys Ile Ser Gly Glu Ala Gln Arg Met Ser Val Leu Val Glu Asp
    290                 295                 300

Leu Leu Ser Leu Thr Arg Ala Glu Gly Gln Gln Met Glu Lys Arg Pro
305                 310                 315                 320

Val Asp Val Leu Glu Leu Ser Leu Ser Val Ala Ser Ser Met Arg Ala
                325                 330                 335

Ala Trp Pro Glu Arg Ser Ile Thr Val Val Asn Lys Thr Gly Ser Leu
            340                 345                 350

Pro Val Val Glu Gly Asp Ala Thr Arg Leu His Gln Val Leu Thr Asn

```
                 355               360                365
Leu Val Asn Asn Gly Leu Asn His Gly Gly Pro Asp Ala Ser Val Glu
    370              375                380

Ile Glu Ile Ser Ala Glu Gly Gly Ser Val Leu Val Arg Val Val Asp
385                  390                395                 400

Asp Gly Val Gly Met Thr Ala Glu Asp Ala Gln His Ile Phe Glu Arg
                405                410                 415

Phe Tyr Arg Thr Asp Thr Ser Arg Ser Arg Ala Ser Gly Gly Ser Gly
            420                425                430

Leu Gly Leu Ala Ile Thr Lys Ser Leu Val Glu Gly His Arg Gly Thr
        435                440                445

Ile Thr Val Asp Ser Glu Val Gly Glu Gly Thr Val Phe Thr Ile Thr
450                 455                460

Leu Pro Ser Arg Met Glu Asp
465                 470

<210> SEQ ID NO 31
<211> LENGTH: 708
<212> TYPE: DNA
<213> ORGANISM: Corynebacterium glutamicum

<400> SEQUENCE: 31
atggacaacc agtctgacgg acaaatccgc gtactcgtcg ttgatgacga gccaaacatc    60
gtcgagctgc tcaccgtaag ccttaaattc aaggcttcg cagtgatgac cgccaacgat    120
ggcaatgaag ccctgaagat tgctcgtgag ttccgtccag acgcatacat cctcgatgtc    180
atgatgccag aatggacgg cttcgagctg ctgaccaagc tgcgcggcga aggccttgac    240
agcccagttc tgtacctcac cgcaaaggat gccgtggagc accgcatcca cggcctgacc    300
atcggcgctg acgactacgt gaccaagcct ttctccctgg aagaagtaat caccccgcctg    360
cgcgtgattc ttcgtcgcgg tggagcagtt gaagaagaca cctcaacttc cctgcagtac    420
gcagacctca ccctcaacga tgaaacccac gaggtcacca aggctggcga actgatcgat    480
ctttccccaa ctgaattcaa cctcctgcgc tacctcatgc tcaacgctga agtggtgctg    540
tccaaggcaa agatcctgga taacgtgtgg cactacgatt tggtggcga cggcaacgtc    600
gtggaatcct acatctccta cctgcgccgc aaggtggaca cccaggatcc gcagctaatt    660
cagactgttc gtggcgttgg atatgttctg cgcaccccac gtagctaa          708

<210> SEQ ID NO 32
<211> LENGTH: 235
<212> TYPE: PRT
<213> ORGANISM: Corynebacterium glutamicum

<400> SEQUENCE: 32

Met Asp Asn Gln Ser Asp Gly Gln Ile Arg Val Leu Val Val Asp Asp
1               5                   10                  15

Glu Pro Asn Ile Val Glu Leu Leu Thr Val Ser Leu Lys Phe Gln Gly
                20                  25                  30

Phe Ala Val Met Thr Ala Asn Asp Gly Asn Glu Ala Leu Lys Ile Ala
            35                  40                  45

Arg Glu Phe Arg Pro Asp Ala Tyr Ile Leu Asp Val Met Met Pro Gly
        50                  55                  60

Met Asp Gly Phe Glu Leu Leu Thr Lys Leu Arg Gly Glu Gly Leu Asp
65                  70                  75                  80

Ser Pro Val Leu Tyr Leu Thr Ala Lys Asp Ala Val Glu His Arg Ile
```

```
                    85                  90                  95
His Gly Leu Thr Ile Gly Ala Asp Asp Tyr Val Thr Lys Pro Phe Ser
                100                 105                 110

Leu Glu Glu Val Ile Thr Arg Leu Arg Val Ile Leu Arg Arg Gly Gly
            115                 120                 125

Ala Val Glu Glu Asp Thr Thr Ser Leu Gln Tyr Ala Asp Leu Thr
        130                 135                 140

Leu Asn Asp Glu Thr His Glu Val Thr Lys Ala Gly Glu Leu Ile Asp
145                 150                 155                 160

Leu Ser Pro Thr Glu Phe Asn Leu Leu Arg Tyr Leu Met Leu Asn Ala
                165                 170                 175

Glu Val Val Leu Ser Lys Ala Lys Ile Leu Asp Asn Val Trp His Tyr
            180                 185                 190

Asp Phe Gly Gly Asp Gly Asn Val Val Glu Ser Tyr Ile Ser Tyr Leu
        195                 200                 205

Arg Arg Lys Val Asp Thr Gln Asp Pro Gln Leu Ile Gln Thr Val Arg
    210                 215                 220

Gly Val Gly Tyr Val Leu Arg Thr Pro Arg Ser
225                 230                 235

<210> SEQ ID NO 33
<211> LENGTH: 1500
<212> TYPE: DNA
<213> ORGANISM: Corynebacterium glutamicum

<400> SEQUENCE: 33
atgtttaaca accgtatccg cactgcagct ctcgctggtg caatcgcaat ctccaccgca      60
gcttccggcg tagctatccc agcattcgct caggagacca acccaacctt caacatcaac     120
aacggcttca cgatgctga tggatccacc atccagccag ttgagccagt taaccacacc     180
gaggaaaccc tccgcgacct gactgactcc accggcgctt acctggaaga gttccagtac     240
ggcaacgttg aggaaatcgt tgaagcatac ctgcaggttc aggcttccgc agacggattc     300
gatccttctg gcaggctgc ttacgaggct ttcgaggctg ctcgcgttcg tgcatcccag     360
gagctcgcgg cttccgctga gaccatcact aagacccgcg agtccgttgc ttacgcactc     420
aaggctgacc gcgaagctac cgcagctttc gaggcttacc tcagcgctct tcgtcaggtt     480
tcagtcatca cgatctgat cgctgatgct aacgccaaga caagactga ctttgcagag     540 atcgagctct acgatgttct ttacaccgac gccgacatct ctggcgatgc tccacttctt     600
gctcctgcat acaaggagct gaaggacctt caggctgagg ttgacgcaga cttcgagtgg     660
ttgggcgagt cgcaattga taacaatgaa gacaactacg tcattcgtac tcacatccct     720
gctgtagagg cactcaaggc agcgatcgat tcactggtcg acaccgttga gccacttcgt     780
gcagacgcta tcgctaagaa catcgaggct cagaagtctg acgttctggt tccccagctc     840
ttcctcgagc gtgcaactgc acagcgcgac ccctgcgtg ttgtagaggc aatcttctct     900
acctctgctc gttacgttga actctacgag aacgtcgaga cgttaacgt tgagaacaag     960 acccttcgcc agcactactc ttccctgatc cctaacctct tcatcgcagc ggttggcaac    1020
atcaacgagc tcaacaatgc agatcaggct gcacgtgagc tcttcctcga ttgggacacc    1080
gacctcacca ccaacgatga ggacgaagct tactaccagg ctaagctcga cttcgctatc    1140
gagacctacg caaagatcct gatcaacggt gaagtttggc aggagccact cgcttacgtc    1200
cagaacctgg atgcaggcgc acgtcaggaa gcagctgacc gcgaagcaga gcgcgcagct    1260
```

```
gacgcagcat accgcgctga gcagctccgc atcgctcagg aagcagctga cgctcagaag    1320
gctctcgctg aggctcttgc taatgcaggc aacaacgaca acggtggcga caactcctcc    1380
gacgacaagg gaaccggttc ttccgacatc ggaacctggg gaccttcgc agcaattgca     1440 gctatcatcg cagcaatcgc agctatcttc ccattcctct ccggtatcgt taagttctaa    1500
```

<210> SEQ ID NO 34
<211> LENGTH: 499
<212> TYPE: PRT
<213> ORGANISM: Corynebacterium glutamicum

<400> SEQUENCE: 34

```
Met Phe Asn Asn Arg Ile Arg Thr Ala Ala Leu Ala Gly Ala Ile Ala
 1               5                  10                  15

Ile Ser Thr Ala Ala Ser Gly Val Ala Ile Pro Ala Phe Ala Gln Glu
                20                  25                  30

Thr Asn Pro Thr Phe Asn Ile Asn Asn Gly Phe Asn Asp Ala Asp Gly
             35                  40                  45

Ser Thr Ile Gln Pro Val Glu Pro Val Asn His Thr Glu Glu Thr Leu
 50                  55                  60

Arg Asp Leu Thr Asp Ser Thr Gly Ala Tyr Leu Glu Glu Phe Gln Tyr
 65                  70                  75                  80

Gly Asn Val Glu Glu Ile Val Glu Ala Tyr Leu Gln Val Gln Ala Ser
                 85                  90                  95

Ala Asp Gly Phe Asp Pro Ser Glu Gln Ala Ala Tyr Glu Ala Phe Glu
            100                 105                 110

Ala Ala Arg Val Arg Ala Ser Gln Glu Leu Ala Ala Ser Ala Glu Thr
        115                 120                 125

Ile Thr Lys Thr Arg Glu Ser Val Ala Tyr Ala Leu Lys Ala Asp Arg
130                 135                 140

Glu Ala Thr Ala Ala Phe Glu Ala Tyr Leu Ser Ala Leu Arg Gln Val
145                 150                 155                 160

Ser Val Ile Asn Asp Leu Ile Ala Asp Ala Asn Ala Lys Asn Lys Thr
                165                 170                 175

Asp Phe Ala Glu Ile Glu Leu Tyr Asp Val Leu Tyr Thr Asp Ala Asp
            180                 185                 190

Ile Ser Gly Asp Ala Pro Leu Leu Ala Pro Ala Tyr Lys Glu Leu Lys
        195                 200                 205

Asp Leu Gln Ala Glu Val Asp Ala Asp Phe Glu Trp Leu Gly Glu Phe
210                 215                 220

Ala Ile Asp Asn Asn Glu Asp Asn Tyr Val Ile Arg Thr His Ile Pro
225                 230                 235                 240

Ala Val Glu Ala Leu Lys Ala Ala Ile Asp Ser Leu Val Asp Thr Val
                245                 250                 255

Glu Pro Leu Arg Ala Asp Ala Ile Ala Lys Asn Ile Glu Ala Gln Lys
            260                 265                 270

Ser Asp Val Leu Val Pro Gln Leu Phe Leu Glu Arg Ala Thr Ala Gln
        275                 280                 285

Arg Asp Thr Leu Arg Val Val Glu Ala Ile Phe Ser Thr Ser Ala Arg
290                 295                 300

Tyr Val Glu Leu Tyr Glu Asn Val Glu Asn Val Glu Asn Lys
305                 310                 315                 320

Thr Leu Arg Gln His Tyr Ser Ser Leu Ile Pro Asn Leu Phe Ile Ala
                325                 330                 335
```

Ala Val Gly Asn Ile Asn Glu Leu Asn Asn Ala Asp Gln Ala Ala Arg
              340                 345                 350

Glu Leu Phe Leu Asp Trp Asp Thr Asp Leu Thr Thr Asn Asp Glu Asp
          355                 360                 365

Glu Ala Tyr Tyr Gln Ala Lys Leu Asp Phe Ala Ile Glu Thr Tyr Ala
      370                 375                 380

Lys Ile Leu Ile Asn Gly Glu Val Trp Gln Glu Pro Leu Ala Tyr Val
385                 390                 395                 400

Gln Asn Leu Asp Ala Gly Ala Arg Gln Glu Ala Ala Asp Arg Glu Ala
              405                 410                 415

Glu Arg Ala Ala Asp Ala Ala Tyr Arg Ala Glu Gln Leu Arg Ile Ala
          420                 425                 430

Gln Glu Ala Ala Asp Ala Gln Lys Ala Leu Glu Ala Leu Ala Asn
      435                 440                 445

Ala Gly Asn Asn Asp Asn Gly Gly Asp Asn Ser Ser Asp Asp Lys Gly
450                 455                 460

Thr Gly Ser Ser Asp Ile Gly Thr Trp Gly Pro Phe Ala Ala Ile Ala
465                 470                 475                 480

Ala Ile Ile Ala Ala Ile Ala Ala Ile Phe Pro Phe Leu Ser Gly Ile
              485                 490                 495

Val Lys Phe

<210> SEQ ID NO 35
<211> LENGTH: 318
<212> TYPE: DNA
<213> ORGANISM: Corynebacterium glutamicum

<400> SEQUENCE: 35
atgtccctcg gaccatggga aattggaatc attgtcctgc tgatcatcgt gctgttcggc    60
gcgaagaagc tgcctgatgc agctcgttcc atcggccgtt ccatgcgcat cttcaagtct   120
gaagtcaaag aaatgaacaa ggacggcgat accccagaac aacagcagca gcctcagcag   180
cagattgcgc ccaaccagat cgaggctcct cagccaaact tgagcagca ctaccaggga    240
cagcaggttc agcagcctca gaaccctcag acccctgact accgtcagaa ctacgaggat   300
ccaaaccgca cctcttaa                                                 318

<210> SEQ ID NO 36
<211> LENGTH: 105
<212> TYPE: PRT
<213> ORGANISM: Corynebacterium glutamicum

<400> SEQUENCE: 36

Met Ser Leu Gly Pro Trp Glu Ile Gly Ile Ile Val Leu Leu Ile Ile
1               5                   10                  15

Val Leu Phe Gly Ala Lys Lys Leu Pro Asp Ala Ala Arg Ser Ile Gly
              20                  25                  30

Arg Ser Met Arg Ile Phe Lys Ser Glu Val Lys Glu Met Asn Lys Asp
          35                  40                  45

Gly Asp Thr Pro Glu Gln Gln Gln Pro Gln Gln Ile Ala Pro
      50                  55                  60

Asn Gln Ile Glu Ala Pro Gln Pro Asn Phe Glu Gln His Tyr Gln Gly
65                  70                  75                  80

Gln Gln Val Gln Gln Pro Gln Asn Pro Gln Thr Pro Asp Tyr Arg Gln
              85                  90                  95

Asn Tyr Glu Asp Pro Asn Arg Thr Ser

<210> SEQ ID NO 37
<211> LENGTH: 471
<212> TYPE: DNA
<213> ORGANISM: Corynebacterium glutamicum

<400> SEQUENCE: 37

```
atgttttcta gcgtgggttg gggagagatc ttcctcttag tcgttgtggg ccttgttgtc      60
atcggcccgg aacggttgcc tcgtttgatc caggacgcac gcgctgcgct gctcgctgca     120
cgtaccgcta tcgacaatgc aaagcagtcg ttggacagtg attttggttc ggaatttgat     180
gaaatccgaa agccactaac ccaggttgca cagtacagcc ggatgagccc caagacggcc     240
atcactaagg cgttatttga taatgattcc tcgttcctgg atgactttga tccaaagaag     300
atcatggccg aaggaacaga aggcgaagct cagcgcaaca agcaggcagc tgacaacaat     360
gcgaatgtgg tggaacgtcc agctgatggt tccaccgcac gcccaacgca aaacgatcca     420
aaagacggcc cgaattactc aggtggcgtc tcttggaccg atattattta g              471
```

<210> SEQ ID NO 38
<211> LENGTH: 156
<212> TYPE: PRT
<213> ORGANISM: Corynebacterium glutamicum

<400> SEQUENCE: 38

```
Met Phe Ser Ser Val Gly Trp Gly Glu Ile Phe Leu Leu Val Val Val
1               5                   10                  15

Gly Leu Val Val Ile Gly Pro Glu Arg Leu Pro Arg Leu Ile Gln Asp
            20                  25                  30

Ala Arg Ala Ala Leu Leu Ala Ala Arg Thr Ala Ile Asp Asn Ala Lys
        35                  40                  45

Gln Ser Leu Asp Ser Asp Phe Gly Ser Glu Phe Asp Glu Ile Arg Lys
    50                  55                  60

Pro Leu Thr Gln Val Ala Gln Tyr Ser Arg Met Ser Pro Lys Thr Ala
65                  70                  75                  80

Ile Thr Lys Ala Leu Phe Asp Asn Asp Ser Ser Phe Leu Asp Asp Phe
                85                  90                  95

Asp Pro Lys Lys Ile Met Ala Glu Gly Thr Glu Gly Glu Ala Gln Arg
            100                 105                 110

Asn Lys Gln Ala Ala Asp Asn Asn Ala Asn Val Val Glu Arg Pro Ala
        115                 120                 125

Asp Gly Ser Thr Ala Arg Pro Thr Gln Asn Asp Pro Lys Asp Gly Pro
    130                 135                 140

Asn Tyr Ser Gly Gly Val Ser Trp Thr Asp Ile Ile
145                 150                 155
```

<210> SEQ ID NO 39
<211> LENGTH: 945
<212> TYPE: DNA
<213> ORGANISM: Corynebacterium glutamicum

<400> SEQUENCE: 39

```
atgtccattg ttgagcacat caaagagttt cgacgccgac ttcttatcgc tctggcgggc      60
atcctcgtgg gcaccattat cggctttatt tggtacgatt tctcattttg gcagatcccc     120
actttgggcg agctgctgag ggatccgtac tgttctctgc ctgctgaatc ccgctgggcc     180
atgagcgact cagaggaatg tcgactgctc gcaaccggcc cgtttgatcc attcatgctt     240
```

```
cgccttaaag tagcggcgtt ggtgggtatg gttcttggct cacccgtgtg gctgagccag    300
ctgtggggct ttatcacccc aggtttgatg aagaatgagc gccgttacac cgcaatcttc    360
gtcacgattg ctgttgtgct gtttgtcggc ggtgctgttc ttgcgtactt cgtcgttgca    420 tatggttttgg agttcctcct taccattggt ggagacaccc aggcagcggc cctgactggt    480
gataagtact tcggattctt gctcgcgttg ttggcgattt tcggcgtgag cttcgaagtt    540
ccactggtga tcggcatgct caacattgtg gtatcttgc cttacgatgc cattaaagat    600
aagcgacgca tgatcatcat gattttgttc gtgttcgctg ctttcatgac acccggccag    660
gatcctttca ccatgttggt gttggcgctt tcactcaccg ttctggtaga gcttgccctg    720
cagttctgtc gtttcaacga caaacgccgg acaagaagc gcccagaatg gcttgatggc    780
gatgacctct ctgcatcacc actggatact tctgctggtg gagaagatgc tccaagccca    840
gtcgaaaccc cagaggcggt ggagccttcg cggatgctga acccaagtgg ggaggcgtcg    900
ataagctata aacccgggcg cgccgacttc ggtgacgtgc tctag                    945
```

<210> SEQ ID NO 40
<211> LENGTH: 314
<212> TYPE: PRT
<213> ORGANISM: Corynebacterium glutamicum

<400> SEQUENCE: 40

```
Met Ser Ile Val Glu His Ile Lys Glu Phe Arg Arg Arg Leu Leu Ile
1               5                   10                  15

Ala Leu Ala Gly Ile Leu Val Gly Thr Ile Gly Phe Ile Trp Tyr
            20                  25                  30

Asp Phe Ser Phe Trp Gln Ile Pro Thr Leu Gly Glu Leu Leu Arg Asp
        35                  40                  45

Pro Tyr Cys Ser Leu Pro Ala Glu Ser Arg Trp Ala Met Ser Asp Ser
    50                  55                  60

Glu Glu Cys Arg Leu Leu Ala Thr Gly Pro Phe Asp Pro Phe Met Leu
65                  70                  75                  80

Arg Leu Lys Val Ala Ala Leu Val Gly Met Val Leu Gly Ser Pro Val
                85                  90                  95

Trp Leu Ser Gln Leu Trp Gly Phe Ile Thr Pro Gly Leu Met Lys Asn
            100                 105                 110

Glu Arg Arg Tyr Thr Ala Ile Phe Val Thr Ile Ala Val Val Leu Phe
        115                 120                 125

Val Gly Gly Ala Val Leu Ala Tyr Phe Val Val Ala Tyr Gly Leu Glu
    130                 135                 140

Phe Leu Leu Thr Ile Gly Gly Asp Thr Gln Ala Ala Ala Leu Thr Gly
145                 150                 155                 160

Asp Lys Tyr Phe Gly Phe Leu Leu Ala Leu Leu Ala Ile Phe Gly Val
                165                 170                 175

Ser Phe Glu Val Pro Leu Val Ile Gly Met Leu Asn Ile Val Gly Ile
            180                 185                 190

Leu Pro Tyr Asp Ala Ile Lys Asp Lys Arg Arg Met Ile Ile Met Ile
        195                 200                 205

Leu Phe Val Phe Ala Ala Phe Met Thr Pro Gly Gln Asp Pro Phe Thr
    210                 215                 220

Met Leu Val Leu Ala Leu Ser Leu Thr Val Leu Val Glu Leu Ala Leu
225                 230                 235                 240

Gln Phe Cys Arg Phe Asn Asp Lys Arg Arg Asp Lys Lys Arg Pro Glu
```

```
                        245                 250                 255
Trp Leu Asp Gly Asp Asp Leu Ser Ala Ser Pro Leu Asp Thr Ser Ala
                260                 265                 270
Gly Gly Glu Asp Ala Pro Ser Pro Val Glu Thr Pro Glu Ala Val Glu
            275                 280                 285
Pro Ser Arg Met Leu Asn Pro Ser Gly Glu Ala Ser Ile Ser Tyr Lys
        290                 295                 300
Pro Gly Arg Ala Asp Phe Gly Asp Val Leu
305                 310
```

<210> SEQ ID NO 41
<211> LENGTH: 39
<212> TYPE: PRT
<213> ORGANISM: Escherichia coli

<400> SEQUENCE: 41

```
Met Asn Asn Asn Asp Leu Phe Gln Ala Ser Arg Arg Phe Leu Ala
1               5                   10                  15
Gln Leu Gly Gly Leu Thr Val Ala Gly Met Leu Gly Pro Ser Leu Leu
            20                  25                  30
Thr Pro Arg Arg Ala Thr Ala
        35
```

<210> SEQ ID NO 42
<211> LENGTH: 27
<212> TYPE: PRT
<213> ORGANISM: Escherichia coli

<400> SEQUENCE: 42

```
Met Ser Leu Ser Arg Arg Gln Phe Ile Gln Ala Ser Gly Ile Ala Leu
1               5                   10                  15
Cys Ala Gly Ala Val Pro Leu Lys Ala Ser Ala
            20                  25
```

<210> SEQ ID NO 43
<211> LENGTH: 48
<212> TYPE: PRT
<213> ORGANISM: Bacillus subtilis

<400> SEQUENCE: 43

```
Met Ala Tyr Asp Ser Arg Phe Asp Glu Trp Val Gln Lys Leu Lys Glu
1               5                   10                  15
Glu Ser Phe Gln Asn Asn Thr Phe Asp Arg Arg Lys Phe Ile Gln Gly
            20                  25                  30
Ala Gly Lys Ile Ala Gly Leu Ser Leu Gly Leu Thr Ile Ala Gln Ser
        35                  40                  45
```

<210> SEQ ID NO 44
<211> LENGTH: 34
<212> TYPE: PRT
<213> ORGANISM: Bacillus subtilis

<400> SEQUENCE: 44

```
Met Lys Phe Val Lys Arg Arg Thr Thr Ala Leu Val Thr Thr Leu Met
1               5                   10                  15
Leu Ser Val Thr Ser Leu Phe Ala Leu Gln Pro Ser Ala Lys Ala Ala
            20                  25                  30
Glu His
```

```
<210> SEQ ID NO 45
<211> LENGTH: 30
<212> TYPE: PRT
<213> ORGANISM: Arthrobacter globiformis

<400> SEQUENCE: 45

Met Met Asn Leu Ser Arg Arg Thr Leu Leu Thr Thr Gly Ser Ala Ala
1               5                   10                  15

Thr Leu Ala Tyr Ala Leu Gly Met Ala Gly Ser Ala Gln Ala
            20                  25                  30

<210> SEQ ID NO 46
<211> LENGTH: 7
<212> TYPE: PRT
<213> ORGANISM: Artificial Sequence
<220> FEATURE:
<223> OTHER INFORMATION: Twin-Arginine Motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 46

Xaa Arg Arg Xaa Phe Leu Lys
1               5

<210> SEQ ID NO 47
<211> LENGTH: 5
<212> TYPE: PRT
<213> ORGANISM: Artificial Sequence
<220> FEATURE:
<223> OTHER INFORMATION: Twin-Arginine Motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa can be any hydrophobic amino acid

<400> SEQUENCE: 47

Arg Arg Xaa Xaa Xaa
1               5

<210> SEQ ID NO 48
<211> LENGTH: 43
<212> TYPE: PRT
<213> ORGANISM: Corynebacterium glutamicum

<400> SEQUENCE: 48

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
        35                  40

<210> SEQ ID NO 49
<211> LENGTH: 30
<212> TYPE: PRT
<213> ORGANISM: Corynebacterium glutamicum

<400> SEQUENCE: 49
```

-continued

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 50
<211> LENGTH: 25
<212> TYPE: PRT
<213> ORGANISM: Corynebacterium stationis

<400> SEQUENCE: 50

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 51
<211> LENGTH: 469
<212> TYPE: PRT
<213> ORGANISM: Corynebacterium glutamicum

<400> SEQUENCE: 51

Gln Glu Thr Asn Pro Thr Phe Asn Ile Asn Asn Gly Phe Asn Asp Ala
1               5                   10                  15

Asp Gly Ser Thr Ile Gln Pro Val Glu Pro Val Asn His Thr Glu Glu
            20                  25                  30

Thr Leu Arg Asp Leu Thr Asp Ser Thr Gly Ala Tyr Leu Glu Glu Phe
        35                  40                  45

Gln Tyr Gly Asn Val Glu Glu Ile Val Glu Ala Tyr Leu Gln Val Gln
    50                  55                  60

Ala Ser Ala Asp Gly Phe Asp Pro Ser Glu Gln Ala Ala Tyr Glu Ala
65                  70                  75                  80

Phe Glu Ala Ala Arg Val Arg Ala Ser Gln Glu Leu Ala Ala Ser Ala
                85                  90                  95

Glu Thr Ile Thr Lys Thr Arg Glu Ser Val Ala Tyr Ala Leu Lys Ala
            100                 105                 110

Asp Arg Glu Ala Thr Ala Ala Phe Glu Ala Tyr Leu Ser Ala Leu Arg
        115                 120                 125

Gln Val Ser Val Ile Asn Asp Leu Ile Ala Asp Ala Asn Ala Lys Asn
    130                 135                 140

Lys Thr Asp Phe Ala Glu Ile Glu Leu Tyr Asp Val Leu Tyr Thr Asp
145                 150                 155                 160

Ala Asp Ile Ser Gly Asp Ala Pro Leu Leu Ala Pro Ala Tyr Lys Glu
                165                 170                 175

Leu Lys Asp Leu Gln Ala Glu Val Asp Ala Asp Phe Glu Trp Leu Gly
            180                 185                 190

Glu Phe Ala Ile Asp Asn Asn Glu Asp Asn Tyr Val Ile Arg Thr His
        195                 200                 205

Ile Pro Ala Val Glu Ala Leu Lys Ala Ala Ile Asp Ser Leu Val Asp
    210                 215                 220

Thr Val Glu Pro Leu Arg Ala Asp Ala Ile Ala Lys Asn Ile Glu Ala
225                 230                 235                 240

Gln Lys Ser Asp Val Leu Val Pro Gln Leu Phe Leu Glu Arg Ala Thr
                245                 250                 255

Ala Gln Arg Asp Thr Leu Arg Val Val Glu Ala Ile Phe Ser Thr Ser
            260                 265                 270

-continued

```
Ala Arg Tyr Val Glu Leu Tyr Glu Asn Val Glu Asn Val Asn Val Glu
        275                 280                 285

Asn Lys Thr Leu Arg Gln His Tyr Ser Ser Leu Ile Pro Asn Leu Phe
290                 295                 300

Ile Ala Ala Val Gly Asn Ile Asn Glu Leu Asn Asn Ala Asp Gln Ala
305                 310                 315                 320

Ala Arg Glu Leu Phe Leu Asp Trp Asp Thr Asp Leu Thr Thr Asn Asp
            325                 330                 335

Glu Asp Glu Ala Tyr Tyr Gln Ala Lys Leu Asp Phe Ala Ile Glu Thr
            340                 345                 350

Tyr Ala Lys Ile Leu Ile Asn Gly Glu Val Trp Gln Glu Pro Leu Ala
        355                 360                 365

Tyr Val Gln Asn Leu Asp Ala Gly Ala Arg Gln Glu Ala Ala Asp Arg
370                 375                 380

Glu Ala Glu Arg Ala Ala Asp Ala Ala Tyr Arg Ala Glu Gln Leu Arg
385                 390                 395                 400

Ile Ala Gln Glu Ala Ala Asp Ala Gln Lys Ala Leu Ala Glu Ala Leu
            405                 410                 415

Ala Asn Ala Gly Asn Asn Asp Asn Gly Gly Asp Asn Ser Ser Asp Asp
        420                 425                 430

Lys Gly Thr Gly Ser Ser Asp Ile Gly Thr Trp Gly Pro Phe Ala Ala
            435                 440                 445

Ile Ala Ala Ile Ile Ala Ala Ile Ala Ala Ile Phe Pro Phe Leu Ser
        450                 455                 460

Gly Ile Val Lys Phe
465

<210> SEQ ID NO 52
<211> LENGTH: 4
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala

<400> SEQUENCE: 52

Gln Glu Thr Xaa
1

<210> SEQ ID NO 53
<211> LENGTH: 5
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val

<400> SEQUENCE: 53

Gln Glu Thr Xaa Xaa
1               5

<210> SEQ ID NO 54
<211> LENGTH: 6
<212> TYPE: PRT
<213> ORGANISM: Corynebacterium glutamicum
```

```
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val
<220> FEATURE:
<221> NAME/KEY: MISC_FEATURE
<222> LOCATION: (6)..(6)
<223> OTHER INFORMATION: Xaa is Thr or Tyr

<400> SEQUENCE: 54

Gln Glu Thr Xaa Xaa Xaa
1               5

<210> SEQ ID NO 55
<211> LENGTH: 6
<212> TYPE: PRT
<213> ORGANISM: Corynebacterium glutamicum

<400> SEQUENCE: 55

Gln Glu Thr Asn Pro Thr
1               5

<210> SEQ ID NO 56
<211> LENGTH: 6
<212> TYPE: PRT
<213> ORGANISM: Corynebacterium glutamicum

<400> SEQUENCE: 56

Gln Glu Thr Gly Thr Tyr
1               5

<210> SEQ ID NO 57
<211> LENGTH: 6
<212> TYPE: PRT
<213> ORGANISM: Corynebacterium glutamicum

<400> SEQUENCE: 57

Gln Glu Thr Thr Val Thr
1               5

<210> SEQ ID NO 58
<211> LENGTH: 6
<212> TYPE: PRT
<213> ORGANISM: Corynebacterium glutamicum

<400> SEQUENCE: 58

Gln Glu Thr Pro Val Thr
1               5

<210> SEQ ID NO 59
<211> LENGTH: 6
<212> TYPE: PRT
<213> ORGANISM: Corynebacterium glutamicum

<400> SEQUENCE: 59

Gln Glu Thr Ala Val Thr
1               5

<210> SEQ ID NO 60
<211> LENGTH: 4
<212> TYPE: PRT
<213> ORGANISM: Artificial Sequence
<220> FEATURE:
```

<223> OTHER INFORMATION: Factor Xa

<400> SEQUENCE: 60

Ile Glu Gly Arg
1

<210> SEQ ID NO 61
<211> LENGTH: 6
<212> TYPE: PRT
<213> ORGANISM: Artificial Sequence
<220> FEATURE:
<223> OTHER INFORMATION: ProTEV

<400> SEQUENCE: 61

Glu Asn Leu Tyr Phe Gln
1               5

<210> SEQ ID NO 62
<211> LENGTH: 1335
<212> TYPE: DNA
<213> ORGANISM: Corynebacterium glutamicum

<400> SEQUENCE: 62

```
atgcagtcaa gcctagatcg tgtgtcggaa accggacgca atgagctcga tgttgaaacc      60
cttgtgaaga aggggaatca accgggcgcg atgagctatc gcaacagtat ccacattttg     120
acagcctcgc tgctggtcgt gggggttggga gcttccgccc gctgacgct gccgatgttt     180 gcgctgtcgt gcgtgctgtt gtttgtgtgg ggttttctgt acttctatgg atcaaccaaa    240
cgcgtagatt tgagccacgg catgcagctg gctggctgt ttgtgctgac gctggtgtgg     300
atttttatgg tgccgatcgt gcccgtgtcc atttatctgc tgttcccgct gttttttcctc   360 tatctacagg tgatgcctga cgtgagaggc attattgcga ttttgggtgc gacagcgatt   420
gcgattgcca gccagtattc cgtggggttg acctttggtg gtgtgatggg tccggtggtc   480
tctgcgatcg tgaccgtggc tattgattac gcgttccgca cgttgtggcg ggtgaataat   540
gaaaagcagg aattgattga tcagttgatt gaaactcgct cccagctggc ggtgacggaa    600
cgaaatgcgg gtatcgctgc ggaacgtcaa cgtattgcgc atgaaattca cgacacggtc   660
gcccagggac tctcctccat tcaaatgctg ctgcatgtct ctgaacagga gattctcgtt   720
gctgagatgg aagagaagcc aaaggaggcg atcgtgaaga agatgcgcct tgcccgacaa    780
acagcctccg acaatctcag tgaggctcgc gcgatgattg cggcgttgca accagcagcg   840
ctgtctaaaa cctccttgga agcagcactt caccgcgtca gaaccgttg ttgggtatt     900 aattttgtga tttctgtcga cggtgatgtt cgccaactgc ccatgaaaac tgaagccacc    960
cttctgcgaa ttgctcaagg tgcgatcgga aatgtggcga acattcaga ggcgaaaaac    1020 tgccacgtga cactaaccta cgaagacaca gaagtacgcc ttgatgtggt tgatgacggt   1080
gtgggttttg agccttcgga agtgtccagt accccgctg gccttggcca tatcggctta    1140
accgcattgc agcagcgcgc gatggaattg cacggcgaag ttatagtgga atctgcatat   1200
gggcagggta ctgcggtatc tgcagcattg ccggtggagc caccagaggg gtttgtcggg   1260
gcgccggttt tggcagattc ggactcaagt gctacaggcg aggttgaact aagttctcca   1320
actgacgatg agtaa                                                   1335
```

<210> SEQ ID NO 63
<211> LENGTH: 444
<212> TYPE: PRT
<213> ORGANISM: Corynebacterium glutamicum

<400> SEQUENCE: 63

Met Gln Ser Ser Leu Asp Arg Val Ser Glu Thr Gly Arg Asn Glu Leu
1               5                   10                  15

Asp Val Glu Thr Leu Val Lys Lys Gly Asn Gln Pro Gly Ala Met Ser
            20                  25                  30

Tyr Arg Asn Ser Ile His Ile Leu Thr Ala Ser Leu Leu Val Val Gly
        35                  40                  45

Leu Gly Ala Ser Ala Arg Leu Thr Leu Pro Met Phe Ala Leu Ser Cys
    50                  55                  60

Val Leu Leu Phe Val Trp Gly Phe Leu Tyr Phe Tyr Gly Ser Thr Lys
65                  70                  75                  80

Arg Val Asp Leu Ser His Gly Met Gln Leu Gly Trp Leu Phe Val Leu
                85                  90                  95

Thr Leu Val Trp Ile Phe Met Val Pro Ile Val Pro Val Ser Ile Tyr
            100                 105                 110

Leu Leu Phe Pro Leu Phe Phe Leu Tyr Leu Gln Val Met Pro Asp Val
        115                 120                 125

Arg Gly Ile Ile Ala Ile Leu Gly Ala Thr Ala Ile Ala Ile Ala Ser
130                 135                 140

Gln Tyr Ser Val Gly Leu Thr Phe Gly Gly Val Met Gly Pro Val Val
145                 150                 155                 160

Ser Ala Ile Val Thr Val Ala Ile Asp Tyr Ala Phe Arg Thr Leu Trp
                165                 170                 175

Arg Val Asn Asn Glu Lys Gln Glu Leu Ile Asp Gln Leu Ile Glu Thr
            180                 185                 190

Arg Ser Gln Leu Ala Val Thr Glu Arg Asn Ala Gly Ile Ala Ala Glu
        195                 200                 205

Arg Gln Arg Ile Ala His Glu Ile His Asp Thr Val Ala Gln Gly Leu
210                 215                 220

Ser Ser Ile Gln Met Leu Leu His Val Ser Gln Glu Ile Leu Val
225                 230                 235                 240

Ala Glu Met Glu Glu Lys Pro Lys Glu Ala Ile Val Lys Lys Met Arg
                245                 250                 255

Leu Ala Arg Gln Thr Ala Ser Asp Asn Leu Ser Glu Ala Arg Ala Met
            260                 265                 270

Ile Ala Ala Leu Gln Pro Ala Ala Leu Ser Lys Thr Ser Leu Glu Ala
        275                 280                 285

Ala Leu His Arg Val Thr Glu Pro Leu Leu Gly Ile Asn Phe Val Ile
    290                 295                 300

Ser Val Asp Gly Asp Val Arg Gln Leu Pro Met Lys Thr Glu Ala Thr
305                 310                 315                 320

Leu Leu Arg Ile Ala Gln Gly Ala Ile Gly Asn Val Ala Lys His Ser
                325                 330                 335

Glu Ala Lys Asn Cys His Val Thr Leu Thr Tyr Glu Asp Thr Glu Val
            340                 345                 350

Arg Leu Asp Val Val Asp Asp Gly Val Gly Phe Glu Pro Ser Glu Val
        355                 360                 365

Ser Ser Thr Pro Ala Gly Leu Gly His Ile Gly Leu Thr Ala Leu Gln
    370                 375                 380

Gln Arg Ala Met Glu Leu His Gly Glu Val Ile Val Glu Ser Ala Tyr
385                 390                 395                 400

Gly Gln Gly Thr Ala Val Ser Ala Ala Leu Pro Val Glu Pro Pro Glu

```
                    405                 410                 415
Gly Phe Val Gly Ala Pro Val Leu Ala Asp Ser Asp Ser Ser Ala Thr
            420                 425                 430
Gly Glu Val Glu Leu Ser Ser Pro Thr Asp Asp Glu
            435                 440
```

<210> SEQ ID NO 64
<211> LENGTH: 639
<212> TYPE: DNA
<213> ORGANISM: Corynebacterium glutamicum

<400> SEQUENCE: 64

```
atgattcgcg tgctgcttgc tgatgaccac gaaatcgtga ggctcggact ccgggctgtg      60
ctggaaagcg ccgaggacat tgaagtggtg ggcgaagtct ccaccgccga aggtgcggtg     120
caggcagccc gagaaggcgg aatcgacgtc atcttgatgg acctccgatt cggccccggc     180
gtccaaggaa cccaggtatc caccggcgca gacgccaccg cagccatcaa gcgaaacatc     240
gataaccccgc caaaagtcct ggttgtgacc aactacgaca ccgacacaga catcctcggc     300
gcaatcgaag ccggcgcact gggctacctg ctcaaagacg ccccaccgag cgaactcctg     360
gcagcagtac gatccgcagc agaaggtgac tccacactgt cacccatggt tgctaaccgc     420
ctgatgactc gcgtgcgaac ccccaaaacc tcactcaccc cacgcgagct ggaggttctc     480
aaactggtcg ccggcggttc ctccaaccgc gacattggcc gtatcctctt cctctcagaa     540
gccacggtga atcccacct cgtgcacatc tacgacaagc tcggcgtgcg gtcacgtacc     600
tccgctgtcg cagccgcacg tgagcagggg ctgctgtag                            639
```

<210> SEQ ID NO 65
<211> LENGTH: 212
<212> TYPE: PRT
<213> ORGANISM: Corynebacterium glutamicum

<400> SEQUENCE: 65

```
Met Ile Arg Val Leu Leu Ala Asp Asp His Glu Ile Val Arg Leu Gly
1               5                  10                  15
Leu Arg Ala Val Leu Glu Ser Ala Glu Asp Ile Glu Val Val Gly Glu
            20                  25                  30
Val Ser Thr Ala Glu Gly Ala Val Gln Ala Ala Arg Glu Gly Gly Ile
        35                  40                  45
Asp Val Ile Leu Met Asp Leu Arg Phe Gly Pro Gly Val Gln Gly Thr
    50                  55                  60
Gln Val Ser Thr Gly Ala Asp Ala Thr Ala Ala Ile Lys Arg Asn Ile
65                  70                  75                  80
Asp Asn Pro Pro Lys Val Leu Val Val Thr Asn Tyr Asp Thr Asp Thr
                85                  90                  95
Asp Ile Leu Gly Ala Ile Glu Ala Gly Ala Leu Gly Tyr Leu Leu Lys
            100                 105                 110
Asp Ala Pro Pro Ser Glu Leu Leu Ala Ala Val Arg Ser Ala Ala Glu
        115                 120                 125
Gly Asp Ser Thr Leu Ser Pro Met Val Ala Asn Arg Leu Met Thr Arg
    130                 135                 140
Val Arg Thr Pro Lys Thr Ser Leu Thr Pro Arg Glu Leu Glu Val Leu
145                 150                 155                 160
Lys Leu Val Ala Gly Gly Ser Ser Asn Arg Asp Ile Gly Arg Ile Leu
                165                 170                 175
```

```
Phe Leu Ser Glu Ala Thr Val Lys Ser His Leu Val His Ile Tyr Asp
            180                 185                 190

Lys Leu Gly Val Arg Ser Arg Thr Ser Ala Val Ala Ala Ala Arg Glu
        195                 200                 205

Gln Gly Leu Leu
    210
```